(12) United States Patent
Horsager et al.

(10) Patent No.: US 12,097,268 B2
(45) Date of Patent: Sep. 24, 2024

(54) MODULATION OF NEURAL PATHWAYS

(71) Applicant: EOS Neuroscience, Inc., San Francisco, CA (US)

(72) Inventors: Alan Horsager, Los Angeles, CA (US); Andrew Smith, Santa Monica, CA (US); Benjamin C. Matteo, San Francisco, CA (US)

(73) Assignee: EOS Neuroscience, Inc., San Francisco, CA (US)

( * ) Notice: Subject to any disclaimer, the term of this patent is extended or adjusted under 35 U.S.C. 154(b) by 884 days.

(21) Appl. No.: 16/823,905

(22) Filed: Mar. 19, 2020

(65) Prior Publication Data

US 2021/0128750 A1  May 6, 2021

Related U.S. Application Data

(63) Continuation of application No. 13/879,004, filed as application No. PCT/US2011/056475 on Oct. 14, 2011, now abandoned.

(60) Provisional application No. 61/393,787, filed on Oct. 15, 2010, provisional application No. 61/393,779, filed on Oct. 15, 2010.

(51) Int. Cl.
*A61K 48/00* (2006.01)
*C07K 14/47* (2006.01)

(52) U.S. Cl.
CPC ...... *A61K 48/0058* (2013.01); *C07K 14/4702* (2013.01); *C12N 2750/14043* (2013.01); *C12N 2830/007* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,912,122 A | 6/1999 | Daggett et al. | |
| 6,204,251 B1 | 3/2001 | Cuthbertson | |
| 6,362,316 B1 | 3/2002 | Daggett et al. | |
| 7,094,604 B2 | 8/2006 | Snyder et al. | |
| 7,144,733 B2 | 12/2006 | Miesenböck et al. | |
| 7,342,111 B2 | 3/2008 | Lewin et al. | |
| 7,824,869 B2 | 11/2010 | Hegemann et al. | |
| 10,307,594 B2 * | 6/2019 | Pepin | A61N 1/36125 |
| 2002/0064870 A1 | 5/2002 | Briand et al. | |
| 2004/0022766 A1 | 2/2004 | Acland et al. | |
| 2005/0202398 A1 | 9/2005 | Hegemann et al. | |
| 2005/0208022 A1 | 9/2005 | Masland | |
| 2006/0088599 A1 | 4/2006 | Prasad et al. | |
| 2007/0053996 A1 | 3/2007 | Boyden et al. | |
| 2007/0054319 A1 | 3/2007 | Boyden et al. | |
| 2007/0259420 A1 | 11/2007 | Greenbaum et al. | |
| 2007/0261127 A1 | 11/2007 | Boyden et al. | |
| 2007/0276024 A1 | 11/2007 | Bond | |
| 2008/0085265 A1 | 4/2008 | Schneider et al. | |
| 2008/0125832 A1 | 5/2008 | Horsager et al. | |
| 2009/0074723 A1 | 3/2009 | Acland et al. | |
| 2009/0088399 A1 | 4/2009 | Balya et al. | |
| 2009/0088680 A1 | 4/2009 | Aravanis et al. | |
| 2009/0099038 A1 | 4/2009 | Deisseroth et al. | |
| 2009/0281163 A1 | 11/2009 | Cepko et al. | |
| 2009/0312818 A1 | 12/2009 | Horsager et al. | |
| 2010/0006049 A1 | 1/2010 | Jung et al. | |
| 2010/0015095 A1 | 1/2010 | Pan et al. | |
| 2010/0016783 A1 | 1/2010 | Bourke et al. | |
| 2010/0190229 A1 | 7/2010 | Zhang et al. | |
| 2010/0234273 A1 | 9/2010 | Boyden et al. | |
| 2011/0021970 A1 | 1/2011 | Vo-Dinh et al. | |
| 2011/0086421 A1 | 4/2011 | Hegemann et al. | |
| 2012/0093772 A1 | 4/2012 | Horsager et al. | |
| 2013/0225664 A1 | 8/2013 | Horsager et al. | |
| 2014/0099284 A1 | 4/2014 | Horsager | |

FOREIGN PATENT DOCUMENTS

| | | |
|---|---|---|
| EP | 1891976 A1 | 2/2008 |
| EP | 1492881 B1 | 10/2008 |
| WO | WO 92/08796 A1 | 5/1992 |
| WO | WO 94/28143 A1 | 12/1994 |
| WO | WO 96/29404 A1 | 9/1996 |
| WO | WO 1998/48027 A2 | 10/1998 |
| WO | WO 1998/48027 A3 | 3/1999 |
| WO | WO 02/00871 A2 | 1/2002 |
| WO | WO 02/086129 A1 | 10/2002 |
| WO | WO 02/086134 A2 | 10/2002 |
| WO | WO 2003/047525 A2 | 6/2003 |
| WO | WO 2003/047525 A3 | 9/2003 |
| WO | WO 2004/009022 A2 | 1/2004 |
| WO | WO 2004/009022 A3 | 7/2004 |
| WO | WO 2004/084951 A2 | 10/2004 |
| WO | WO 2004/084951 A3 | 11/2004 |
| WO | WO 2005/080573 A1 | 9/2005 |

(Continued)

OTHER PUBLICATIONS

Stormo et al., Nature Reviews Genetics vol. 11 (2010), pp. 751-760.
U.S. Appl. No. 60/701,799, filed Jul. 22, 2005, Deisseroth et al.
3rd party observation dated Oct. 2, 2012 against EP Application No. 9800733.9.
Acland et al. Gene therapy restores vision in a canine model of childhood blindness. Nat Genet. 2001;28:92-95.
Acland et al. Long-term restoration of rod and cone vision by single dose rAAV-mediated gene transfer to the retina in a canine model of childhood blindness. Molecular Therapy: the Journal of the American Society of Gene Therapy. 2005;12:1072-1082.

(Continued)

*Primary Examiner* — Robert M Kelly
(74) *Attorney, Agent, or Firm* — Heslin Rothenberg Farley & Mesiti P.C.

(57) ABSTRACT

Provided herein are compositions and methods for the design of synthetic regulatory sequences and for subsequent modulation of neural pathways.

20 Claims, 10 Drawing Sheets

Specification includes a Sequence Listing.

(56) References Cited

FOREIGN PATENT DOCUMENTS

| WO | WO 2006/079217 A1 | 8/2006 |
|---|---|---|
| WO | WO 2007/131180 A2 | 11/2007 |
| WO | WO 2008/022772 A1 | 2/2008 |
| WO | WO 2007/131180 A3 | 7/2008 |
| WO | WO 2008/086470 A1 | 7/2008 |
| WO | WO 2008/089003 A2 | 7/2008 |
| WO | WO 2008/089003 A3 | 9/2008 |
| WO | WO 2008/124724 A1 | 10/2008 |
| WO | WO 2009/124189 A1 | 10/2009 |
| WO | WO 2009/127705 A1 | 10/2009 |
| WO | WO 2010/006049 A1 | 1/2010 |
| WO | WO 2010/009141 A1 | 1/2010 |
| WO | WO 2010/011404 A2 | 1/2010 |
| WO | WO 2010/123993 A1 | 10/2010 |
| WO | WO 2010/011404 A3 | 2/2011 |

OTHER PUBLICATIONS

Aguirre et al. Canine and human visual cortex intact and responsive despite early retinal blindness from RPE65 mutation. PLoS Medicine. 2007;4:e230.

Allocca, et al. Novel adeno-associated virus serotypes efficiently transduce murine photoreceptors. J Virol. Oct. 2007;81(20):11372-80. Epub Aug. 15, 2007.

Aronoff et al. Controlled and localized genetic manipulation in the brain. Journal of Cellular and Molecular Medicine. 2006;10:333-352.

Arrenberg, et al. Optical control of zebrafish behavior with halorhodopsin. PNAS. 2009; 106(42):17968-17973.

Baccus et al. Timing and computation in inner retinal circuitry. Annu Rev Physiol. 2007;69:271-290.

Baron. Mechanisms of disease: neuropathic pain—a clinical perspective. Nat Clin Pract Neurol. Feb. 2006;2(2):95-106.

Batten et al. Pharmacological and rAAV gene therapy rescue of visual functions in a blind mouse model of Leber congenital amaurosis.[see comment]. PLoS Medicine. 2005;2:e333.

Berndt et al. Bi-stable neural state switches. Nat Neurosci. Feb. 2009;12(2):229-34.

Beutler, et al. Intrathecal gene transfer by adeno-associated virus for pain. Curr Opin Mol Ther. Oct. 2005;7(5):431-9.

Beutler, et al. Retrovirus-mediated expression of an artificial beta-endorphin precursor in primary fibroblasts. J Neurochem. Feb. 1995;64(2):475-81.

Bi, et al. Ectopic Expression of a Microbial-Type Rhodopsin Restores Visual Responses in Mice with Photoreceptor Degeneration. Nueron. 2006;50(1):23-33.

Borrás. Recent developments in ocular gene therapy. Experimental Eye Research. 2003;76(6):643-652.

Bowie, et al. Deciphering the message in protein sequences: tolerance to amino acid substitutions. Science. Mar. 16, 1990;247(4948):1306-10.

Boyden, et al. Millisecond-timescale, genetically targeted optical control of neural activity. Nat Neurosci. Sep. 2005;8(9):1263-8. Epub Aug. 14, 2005.

Carlton, et al. Behavioral manifestations of an experimental model for peripheral neuropathy produced by spinal nerve ligation in the primate. Pain. Feb. 1994;56(2):155-66.

Casini et al. Developmental expression of neurokinin-1 and neurokinin-3 receptors in the rat retina. The Journal of Comparative Neurology. 2000;421(2):275-287.

Cemazar et al. Electrically-assisted nucleic acids delivery to tissues in vivo: where do we stand? Current Pharmaceutical Design. 2006;12:3817-3825.

Chader. Animal models in research on retinal degenerations: past progress and future hope. Vision Research. 2002;42:393-399.

Chow, et al. High-performance genetically targetable optical neural silencing by light-driven proton pumps. Nature. Jan. 7, 2010;463(7277):98-102.

Christensen, et al. Spinal neurons specifically excited by noxious or thermal stimuli: marginal zone of the dorsal horn. J Neurophysiol. Mar. 1970;33(2):293-307.

Chung, et al. Segmental spinal nerve ligation model of neuropathic pain. Methods Mol Med. 2004;99:35-45.

Congdon et al. Causes and prevalence of visual impairment among adults in the United States. Archives of Ophthalmology. 2004;122:477-485.

De Koning, et al. Methods for producing a reproducible crush in the sciatic and tibial nerve of the rat and rapid and precise testing of return of sensory function. Beneficial effects of melanocortins. J Neurol Sci. Jul. 1986;74(2-3):237-46.

Dhingra et al. Light response of retinal ON bipolar cells requires a specific splice variant of Galpha(o). Journal of Neuroscience. 2002;22:4878-4884.

Dhingra et al. The light response of ON bipolar neurons requires G[alpha]o. Journal of Neuroscience. 2000;20:9053-9058.

Dhingra, et al. Probing neurochemical structure and function of retinal ON bipolar cells with a transgenic mouse. J Comp Neurol. Oct. 10, 2008;510(5):484-96.

Dinculescu, et al. Adeno-associated virus-vectored gene therapy for retinal disease. Hum Gene Ther. Jun. 2005;16(6):649-63.

Doroudchi, et al. Virally delivered channelrhodopsin-2 safely and effectively restores visual function in multiple mouse models of blindness. Mol Ther. Jul. 2011;19(7):1220-9. doi: 10.1038/mt.2011.69. Epub Apr. 19, 2011.

Duvoisin, et al. A novel metabotropic glutamate receptor expressed in the retina and olfactory bulb. J Neurosci. Apr. 1995;15(4):3075-83.

European search report and search opinion dated Dec. 6, 2011 for Application No. 9800733.9.

Finegold, et al. A paracrine paradigm for in vivo gene therapy in the central nervous system: treatment of chronic pain. Hum Gene Ther. May 1, 1999;10(7):1251-7.

Flannery. Looking within for Vision. Neuron. 2006;50(1):1-3.

Fong, et al. The use and development of retroviral vectors to deliver cytokine genes for cancer therapy. Crit Rev Ther Drug Carrier Syst. 2000;17(1):1-60.

Gao et al. New recombinant serotypes of AAV vectors. Current Gene Therapy. 2005;5:285-297.

Gargini et al. Retinal organization in the retinal degeneration 10 (rd10) mutant mouse: a morphological and ERG study. Journal of Comparative Neurology. 2007;500:222-238.

Gracely, et al. New methods of pain measurement and their application to pain control. Int Dent J. Mar. 1978;28(1):52-65.

Greenberg et al. In vivo Transgene Expression in ON-Type Retinal Ganglion Cells: Applications to Retinal Disease. Association of Research in Vision and Ophthalmology; 2007.

Greener, et al. An efficient random mutagenesis technique using an E. coli mutator strain. Methods Mol Biol. 1996;57:375-85.

Hakki Onen, et al. Effects of rapid eye movement (REM) sleep deprivation on pain sensitivity in the rat. Brain Res. May 11, 2001;900(2):261-7.

Han, et al. Millisecond-timescale optical control of neural dynamics in the nonhuman primate brain. Neuron. Apr. 30, 2009;62(2):191-8.

Han, et al. Multiple-color optical activation, silencing, and desynchronization of neural activity, with single-spike temporal resolution. PLoS One. Mar. 21, 2007;2(3):e299.

Harrison, et al. Neuronal-specific and nerve growth factor-inducible expression directed by the preprotachykinin-A promoter delivered by an adeno-associated virus vector. Neuroscience. 1999;94(3):997-1003.

Harvey, et al. Intravitreal injection of adeno-associated viral vectors results in the transduction of different types of retinal neurons in neonatal and adult rats: a comparison with lentiviral vectors. Mol Cell Neurosci. Sep. 2002;21(1):141-57.

Hashimoto, et al. The whole nucleotide sequence and chromosomal localization of the gene for human metabotropic glutamate receptor subtype 6. Eur J Neurosci. Jun. 1997;9(6):1226-35.

Hu, et al. Design of retroviral vectors and helper cells for gene therapy. Pharmacol Rev. Dec. 2000;52(4):493-511.

Humayun et al. Pattern electrical stimulation of the human retina. Vision Research. 1999;39:2569-2576.

(56) References Cited

OTHER PUBLICATIONS

Hungund, et al. Are anandamide and cannabinoid receptors involved in ethanol tolerance? A review of the evidence. Alcohol Alcohol. Mar.-Apr. 2000;35(2):126-33.
International search report and written opinion dated Jan. 3, 2010 for PCT Application No. US2009/04453.
International search report and written opinion dated Jun. 26, 2012 for PCT Application No. US2011/056475.
International search report and written opinion dated Nov. 25, 2011 for PCT Application No. 2011/031297.
Kayser, et al. Differential anti-neuropathic pain effects of tetrodotoxin in sciatic nerve-versus infraorbital nerve-ligated rats-behavioral, pharmacological and immunohistochemical investigations. Neuropharmacology. Feb. 2010;58(2):474-87. Epub Sep. 9, 2009.
Kiasalari, et al. Identification of perineal sensory neurons activated by innocuous heat. J Comp Neurol. Jan. 10, 2010;518(2):137-62.
Kim, et al. A Core Paired-Type and POU Homeodomain-Containing Transcription Factor Program Drives Retinal Bipolar Cell Gene Expression. The Journal of Neuroscience. 2008;28(31):7748-64.
Krebs, et al. Gene replacement in Halobacterium halobium and expression of bacteriorhodopsin mutants. Proc Natl Acad Sci U S A. Mar. 1, 1993;90(5):1987-91.
Krebs, et al. Intramembrane substitutions in helix D of bacteriorhodopsin disrupt the purple membrane. J Mol Biol. Mar. 21, 1997;267(1):172-83.
Lagali et al. Targeted Reporter Gene Expression for Morphological and Functional Assessment of Inner Retinal Neurons in Wild-Type and Retinal Degeneration Mice. Fort Lauderdale, Florida: Association for Research in Vision and Ophthalmology; 2007.
Lagali, et al. Light-activated channels targeted to On bipolar cells restore visual function in retinal degeneration. Nat Neurosci. Jun. 2008;11(6):667-75.
Le Bars, et al. Animal models of nociception. Pharmacol Rev. Dec. 2001;53(4):597-652.
Li et al. Electroporation gene therapy: new developments in vivo and in vitro. Current Gene Therapy. 2004;4:309-316.
Lieber, et al. Integrating adenovirus-adeno-associated virus hybrid vectors devoid of all viral genes. J Virol. Nov. 1999;73(11):9314-24.
Lin, et al. Characterization of engineered channelrhodopsin variants with improved properties and kinetics. Biophys J. Mar. 4, 2009;96(5):1803-14.
Linden, et al. TASK-3 knockout mice exhibit exaggerated nocturnal activity, impairments in cognitive functions, and reduced sensitivity to inhalation anesthetics. J Pharmacol Exp Ther. Dec. 2007;323(3):924-34. Epub Sep. 17, 2007.
Lundstrom. Alphavirus vectors: applications for DNA vaccine production and gene expression. Intervirology. 2000;43(4-6):247-57.
Lungwitz, et al. Polyethylenimine-based non-viral gene delivery systems. Eur J Pharm Biopharm. Jul. 2005;60(2):247-66.
MacLaren et al. Retinal repair by transplantation of photoreceptor precursors. Nature. 2006;444:203-207.
Marc, et al. Neural reprogramming in retinal degeneration. J Neurosci. Apr. 1995;15(4):3075-83.
Masland. The many roles of starburst amacrine cells. Trends in Neurosciences. 2005;28(8)395-396.
Maston, et al. Transcriptional regulatory elements in the human genome. Annu Rev Genomics Hum Genet. 2006;7:29-59.
Medeiros et al. Preservation of ganglion cell layer neurons in age-related macular degeneration. Investigative Ophthalmology & Vision Science. 2001;42(3):795-803.
Melzack, et al. Skin sensory afterglows. Science. Jan. 26, 1968;159(3813):445-7.
Mendell. Physiological properties of unmyelinated fiber projection to the spinal cord. Exp Neurol. Nov. 1966;16(3):316-32.
Mills et al. All amacrine cells limit scotopic acuity in central macaque retina: A confocal analysis of calretinin labeling. J Comp Neurol. 1999;411:19-34.
Miyoshi, et al. Development of a self-inactivating lentivirus vector. J Virol. Oct. 1998;72(10):8150-7.
Moore, et al. peripheral nerve injury promotes a selective loss of GABAergic inhibition in the superficial dorsal born of the spinal cord. J Neurosci. Aug. 1, 2002;22(15):6724-31.
Morrison, et al. An activator element within the preprotachykinin-A promoter. Mol Cell Neurosci. Apr. 1994;5(2):165-75.
Nagel et al. Channelrhodopsin-1: a light-gated proton channel in green algae. Science. 2002;296:2395-2398.
Nagel et al. Channelrhodopsin-2, a directly light-gated cation-selective membrane channel. Proc Natl Acad Sci USA. 2003;100:13940-13945.
Nagel et al. Channelrhodopsins: directly light-gated cation channels. Biochemical Society Transactions. 2005;33:863-866.
Natkunarajah, et al. Assessment of ocular transduction using single-stranded and self-complementary recombinant adeno-associated virus serotype 2/8. Gene Ther. Mar. 2008;15(6):463-7. Epub Nov. 15, 2007.
Nawy, S. The metabotropic receptor mGluR6 may signal through G(o), but not phosphodiesterase, in retinal bipolar cells. J Neurosci. Apr. 15, 1999;19(8):2938-44.
Nichols, et al. Enhancement of the antiallodynic and antinociceptive efficacy of spinal morphine by antisera to dynorphin A (1-13) or MK-801 in a nerve-ligation model of peripheral neuropathy. Pain. Feb. 1997;69(3):317-22.
Office action dated Jan. 14, 2014 for U.S. Appl. No. 12/993,092.
Office action dated Feb. 13, 2013 for U.S. Appl. No. 12/993,092.
Palecek, et al. Responses of spinothalamic tract neurons to mechanical and thermal stimuli in an experimental model of peripheral neuropathy in primates. J Neurophysiol. Dec. 1992;68(6):1951-66.
Pawlyk et al. Gene replacement therapy rescues photoreceptor degeneration in a murine model of Leber congenital amaurosis lacking RPGRIP. Investigative Ophthalmology & Visual Science. 2005;46:3039-3045.
Perri, et al. Replicon vectors derived from Sindbis virus and Semliki forest virus that establish persistent replication in host cells. J Virol. Oct. 2000;74(20):9802-7.
Petrs-Silva et al. High-efficiency Transduction of the Mouse Retina by Tyrosine-mutant AAV Serotype Vectors. Molecular Therapy. 2009;17(3):463-71.
Puhl, et al. Identification of the sensory neuron specific regulatory region for the mouse gene encoding the voltage-gated sodium channel NaV1.8. J Neurochem. Aug. 2008;106(3):1209-24. Epub May 7, 2008.
Punzo et al. Cellular responses to photoreceptor death in the rdl mouse model of retinal degeneration. Investigative Ophthalmology & Visual Science. 2007;48:849-857.
Rakoczy, et al. Mouse models of age-related macular degeneration. Exp Eye Res. May 2006;82(5):741-52. Epub Dec. 1, 2005.
Reutsky, et al. Patterned optical activation of Channelrhodopsin II expressing retinal ganglion cells. Proceedings of the 3rd International IEEE/EMBS Conference on Neural Engineering. Kohala Coast, Hawaii, USA, May 2-5, 2007; pp. 50-52.
Rex, et al. The distribution, concentration, and toxicity of enhanced green fluorescent protein in retinal cells after genomic or somatic (virus-mediated) gene transfer. Mol Vis. Dec. 30, 2005;11:1236-45.
Rizzo et al. Perceptual Efficacy of Electrical Stimulation of Human Retina with a Microelectrode Array during Short-Term Surgical Trials. Invest. Ophthalmol. Vis. Sci. 2003;44:5362-5369.
Roska et al. Vertical interactions across ten parallel, stacked representations in the mammalian retina. Nature. 2001;410:583-587.
Scholz, et al. Blocking caspase activity prevents transsynaptic neuronal apoptosis and the loss of inhibition in lamina II of the dorsal horn after peripheral nerve injury. J Neurosci. Aug. 10, 2005;25(32):7317-23.
Schones, et al. Statistical significance of cis-regulatory modules. BMC Bioinformatics. Jan. 22, 2007;8:19.
Shoda, et al. Increased phosphorylation of extracellular signal-regulated kinase in trigeminal nociceptive neurons following propofol administration in rats. J Pain. Jun. 2009;10(6):573-85. Epub Apr. 23, 2009.
Sineshchekov et al. Two rhodopsins mediate phototaxis to low- and high-intensity light in Chlamydomonas reinhardtii. Proc Natl Acad Sci USA. 2002;99:8689-8694.

(56) References Cited

OTHER PUBLICATIONS

Smith, et al. DNA motifs in human and mouse proximal promoters predict tissue-specific expression. Proc Natl Acad Sci U S A. Apr. 18, 2006;103(16):6275-80. Epub Apr. 10, 2006.
Smith, et al. Identifying tissue-selective transcription factor binding sites in vertebrate promoters. Proc Natl Acad Sci U S A. Feb. 1, 2005;102(5):1560-5. Epub Jan. 24, 2005.
Smith, et al. Tissue-specific regulatory elements in mammalian promoters. Mol Syst Biol. 2007;3:73.
St. Pierre, et al. Differential effects of TRPV channel block on polymodal activation of rat cutaneous nociceptors in vitro. Exp Brain Res. Jun. 2009;196(1):31-44. Epub Apr. 30, 2009.
Stone, et al. Spinal analgesic actions of the new endogenous opioid peptides endomorphin-1 and -2. Neuroreport. Sep. 29, 1997;8(14):3131-5.
Strettoi et al. Modifications of retinal neurons in a mouse model of retinitis pigmentosa, PNAS. 2000;97(20):11020-11025.
Taylor et al. New directions in retinal research. Trends in Neurosciences. 2003;26(7):379-385.
Tian et al. G protein coupling profile of mGluR6 and expression of G alpha proteins in retinal ON bipolar cells. Vis Neurosci. 2006;23:909-916.
Tomita et al. Restoration of visual response in aged dystrophic RCS rats using AAV-mediated channelopsin-2 gene transfer. Investigative Ophthalmology & Visual Science. 2007;48:3821-3826.
Trompeter, et al. Rapid and highly efficient gene transfer into natural killer cells by nucleofection. J Immunol Methods. Mar. 1, 2003;274(1-2):245-56.
Ueda, et al. The mGluR6 5' Upstream Transgene Sequence Directs a Cell-Specific and Developmentally Regulated Expression in Retinal Rod and On-Type Cone Bipolar Cells. The Journal of Neuroscience. 1997;17(9):3014-23.
Vandaele, et al. Purkinje cell protein-2 regulatory regions and transgene expression in cerebellar compartments. Genes Dev. Jul. 1991;5(7):1136-48.
Veraart et al. Vision rehabilitation in the case of blindness. Expert Review of Medical Devices. 2004;1(1):139-153.
Vigna, et al. Lentiviral vectors: excellent tools for experimental gene transfer and promising candidates for gene therapy. J Gene Med. Sep.-Oct. 2000;2(5):308-16.
Wan, et al. In vitro evolution of horse heart myoglobin to increase peroxidase activity. Proc Natl Acad Sci U S A. Oct. 27, 1998;95(22):12825-31.
Wang, et al. Molecular determinants differentiating photocurrent properties of two channelrhodopsins from chlamydomonas. J Biol Chem. Feb. 27, 2009;284(9):5685-96.
Warrington et al. Treatment of human disease by adeno-associated viral gene transfer. Human genetics. 2006;119:571-603.
Wassle et al. Parallel processing in the mammalian retina. Nature Reviews Neuroscience. 2004; 5:747-757.
Weiland et al. Visual task performance in Blind Humans with Retinal Prosthetic Implants. Proceedings of the 26th Annual International Conference of the IEEE EMBS; 2004.
Wen, et al. Exploring the allowed sequence space of a membrane protein. Nat Struct Biol. Feb. 1996;3(2):141-8.
Whaley, et al. Selection of peptides with semiconductor binding specificity for directed nanocrystal assembly. Nature. Jun. 8, 2000;405(6787):665-8.
Winter et al. 3rd. Retinal prostheses: current challenges and future outlook. Journal of Biomaterials Science. 2007;18:1031-1055.
Wu et al. Adeno-associated virus serotypes: vector toolkit for human gene therapy. Molecular Therapy. 2006;14:316-327.
Wu, et al. Self-complementary recombinant adeno-associated viral vectors: packaging capacity and the role of rep proteins in vector purity. Hum Gene Ther. Feb. 2007;18(2):171-82.
Yanai et al. Visual performance using a retinal prosthesis in three subjects with retinitis pigmentosa. American Journal of Ophthalmology. 2007;143:820-827.
Zhang et al. Multimodal fast optical interrogation of neural circuitry. Nature. 2007;446:633-639.
Zhang et al. Red-shifted optogenetic excitation: a tool for fast neural control derived from Volvox carteri. Nature Neuroscience. 2008;11:631-633.
Zhang, et al. Neurokinin-1 receptor enhances TRPVI activity in primary sensory neurons via PKCepsilon: a novel pathway for heat hyperalgesia. J Neurosci. Oct. 31, 2007;27(44):12067-77.
Zheng, et al. Genomic integration and gene expression by a modified adenoviral vector. Nature Biotechnology. 2000; 18:176-180. doi:10.1038/72628.
Zhong et al. A dual role of EGFR protein tyrosine kinase signaling in ubiquitination of AAV2 capsids and viral second-strand DNA synthesis. Molecular Therapy. 2007;15:1323-1330.
Zhong et al. Next generation of adeno-associated virus 2 vectors: point mutations in tyrosines lead to high-efficiency transduction at lower doses. Proc Natl Acad Sci USA. 2008;105:7827-7832.

\* cited by examiner

Expression of eGFP & PKCα in the retina of *rd10* mice 6 weeks after subretinal injection of AAV vector AAV8Y733F-hGRM6-ChR2-eGFP

GFP  PKCα  DAPI

Expression of eGFP & PKCα in the retina of *rd10* mice 6 weeks after subretinal injection of AAV vector

SEQUENCE LISTING

<160> NUMBER OF SEQ ID NOS: 31

<210> SEQ ID NO 1
<211> LENGTH: 221
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
ccgggtacca tccttagatt atgaaacatt tacaattatg aatgaatatt agatgttatc    60
aaatgctttt tctgcatcca tttagataat catgttttc ctttaatctg ttaatgcggt    120
gaattacatt aatagatttc ctaagtcatt aatctgctaa agtgcatttc tgggacaaac   180
agacttggtt atgacattgt atgtataagc ttaccggtgc c                221

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tctggtttgt cccag                                              15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttagcagatt aatga                                              15

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agcagattaa tga                                                13

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgacttagga aatctatt                                           18

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 cattaacag                                                     9

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
attaacagat                                                          10

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaaaacatga ttat                                                     14

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acatgattat cta                                                      13

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aatattcatt cataattgta                                               20

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atattcattc ataattg                                                  17

<210> SEQ ID NO 12
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gatctccaga tggctaaaact tttaaatcat gaatgaagta gatattacca aattgctttt   60
tcagcatcca tttagataat catgtttttt gcctttaatc tgttaatgta gtgaattaca  120
gaaatacatt tcctaaatca ttacatcccc caaatcgtta atctgctaaa gtacatctct  180
ggctcaaaca agactggttg                                              200

<210> SEQ ID NO 13
<211> LENGTH: 198
<212> TYPE: DNA
<213> ORGANISM: Artificial Sequence
<220> FEATURE:

<223> OTHER INFORMATION: Description of Artificial Sequence: Synthetic
      consensus polynucleotide
<220> FEATURE:
<223> OTHER INFORMATION: Sequence derived from human and nonhuman
      primates

<400> SEQUENCE: 13
atacatamaa tgtcataacc aagtctggtt tgtcccagaa atgcacttta gcagattaat    60
gacttaggaa atctattaat gtaattcacy gcattaacag attaaaggaa aaacatgatt   120
atctaaatgg atgcagaaaa agcatttgat aacatctaat attcattcat aattktaaat   180
gtttcataat ctaaggat                                                 198

<210> SEQ ID NO 14
<211> LENGTH: 98
<212> TYPE: DNA
<213> ORGANISM: Homo sapiens

<400> SEQUENCE: 14
atacatacaa tgtcataacc aagtctggtt tgtcccagaa atgcacttta gcagattaat    60
gacttaggaa atctattaat gtaattcacc gcattaac                            98

<210> SEQ ID NO 15
<211> LENGTH: 99
<212> TYPE: DNA
<213> ORGANISM: Tarsius syrichta

<400> SEQUENCE: 15
atatgttaaa aaggcataac caagtctggt ttgtcccaga aatgcacttt agcagattaa    60
tgacttagga aacctattaa tgtaattcat tgcattaac                           99

<210> SEQ ID NO 16
<211> LENGTH: 97
<212> TYPE: DNA
<213> ORGANISM: Callithrix jacchus

<400> SEQUENCE: 16
atacataaat gtcataacca agtctggttt gtcccagaaa tgcactttag cagattaatg    60
acttaggaaa tctattaatg taattcactg cattaac                             97

<210> SEQ ID NO 17
<211> LENGTH: 98
<212> TYPE: DNA
<213> ORGANISM: Macaca mulatta

<400> SEQUENCE: 17
atacataaaa tgtcatcacc aagtctggtt tgtcccagaa atgcacttta gcagattaat    60
gacttaggaa atctattaat gtaattcact gcattaac                            98

<210> SEQ ID NO 18
<211> LENGTH: 98
<212> TYPE: DNA
<213> ORGANISM: Pongo abelii

<400> SEQUENCE: 18
atatataaaa tgtcataacc aagtctggtt tgtcccagaa atgcacttta gcagattaat    60
gacttaggaa atctattaat gtaattcact gcattaac                            98

<210> SEQ ID NO 19
<211> LENGTH: 98

```
<212> TYPE: DNA
<213> ORGANISM: Gorilla gorilla
<220> FEATURE:
<221> NAME/KEY: modified_base
<222> LOCATION: (91)..(91)
<223> OTHER INFORMATION: a, c, t, g, unknown or other

<400> SEQUENCE: 19
atacatacaa tgtcataacc aagtctggtt tgtcccagaa attcacttta gcagattaat      60
gacttaggaa atctattaat gtaattcact ncattaac                              98

<210> SEQ ID NO 20
<211> LENGTH: 90
<212> TYPE: DNA
<213> ORGANISM: Pan troglodytes

<400> SEQUENCE: 20
atacatacaa tgtcataacc aagtctggtt tgtcccagaa atgcacttta gcagattaat      60
gacttaggaa atctaattca ccgcattaac                                       90

<210> SEQ ID NO 21
<211> LENGTH: 100
<212> TYPE: DNA
<213> ORGANISM: Homo sapiens

<400> SEQUENCE: 21
agattaaagg aaaaacatga ttatctaaat ggatgcagaa aaagcatttg ataacatcta      60
atattcattc ataattgtaa atgtttcata atctaaggat                           100

<210> SEQ ID NO 22
<211> LENGTH: 99
<212> TYPE: DNA
<213> ORGANISM: Tarsius syrichta

<400> SEQUENCE: 22
agattaaagg aaaaaacatg attatctaaa tggatgcccc agaagcattt gataatacct      60
aatatttatt catgatttta agttttgcaa cctaagaat                             99

<210> SEQ ID NO 23
<211> LENGTH: 100
<212> TYPE: DNA
<213> ORGANISM: Callithrix jacchus

<400> SEQUENCE: 23
agattaaagg aaaaacatga tcatctaaat ggatgcagaa aaagcatttg ataacatcta      60
atattcattc ataatttaa gtgtttcata atctaaggat                            100

<210> SEQ ID NO 24
<211> LENGTH: 100
<212> TYPE: DNA
<213> ORGANISM: Macaca mulatta

<400> SEQUENCE: 24
agattaaagg aaaaacatga tcatctaaat ggatgcagaa aaagcatttg ataacatcta      60
atattcattc ataattttaa gtgtttcata atctaaggat                           100

<210> SEQ ID NO 25
<211> LENGTH: 100
<212> TYPE: DNA
<213> ORGANISM: Pongo abelii
```

```
<400> SEQUENCE: 25
agattaaagg aaaaacatga ttatctaaat ggatgcagaa aaagcatttg ataacatcta      60
atattcattc ataattttaa atgtttcata atctaaggat                           100

<210> SEQ ID NO 26
<211> LENGTH: 100
<212> TYPE: DNA
<213> ORGANISM: Gorilla gorilla
<220> FEATURE:
<221> NAME/KEY: modified_base
<222> LOCATION: (2)..(2)
<223> OTHER INFORMATION: a, c, t, g, unknown or other

<400> SEQUENCE: 26
anattaaagg aaaaacatga ttatctaaat ggatgcagaa aaagcatttg ataacatcta      60
atatttattc ataattttaa atgtttcata atctaaggat                           100

<210> SEQ ID NO 27
<211> LENGTH: 100
<212> TYPE: DNA
<213> ORGANISM: Pan troglodytes

<400> SEQUENCE: 27
agattaaagg aaaaacatga ttatctaaat ggatgcagaa aaagcatttg ataacatcta      60
atattcattc ataattttaa atgtttcata atctaaggat                           100

<210> SEQ ID NO 28
<211> LENGTH: 200
<212> TYPE: DNA
<213> ORGANISM: Mus sp.

<400> SEQUENCE: 28
caaccagtct tgtttgagcc agagatgtac tttagcagat taacgatttg ggggatgtaa      60
tgatttagga aatgtatttc tgtaattcac tacattaaca gattaaaggc aaaaacatg     120 attatctaaa tggatgctga aaaagcaatt tggtaatatc tacttcattc atgatttaaa    180
agtttagcca tctggagatc                                                 200

<210> SEQ ID NO 29
<211> LENGTH: 194
<212> TYPE: DNA
<213> ORGANISM: Rattus sp.

<400> SEQUENCE: 29
aaccagtctt gtttgaccca gagatgttct ttagcggatt aacgatttgg ggaatgtaat      60
gatttaggaa atgtatttct gtaattcact gcattaacag attaaaggca aaaacatgat    120
tatctaaatg gatgctggaa aagcaatttg gtaaatatct acttcattca tgatttaaaa    180
gtttagccac ctgg                                                       194

<210> SEQ ID NO 30
<211> LENGTH: 168
<212> TYPE: DNA
<213> ORGANISM: Homo sapiens

<400> SEQUENCE: 30
aaccagtctc ggtttgtccc agaaatgcac tttagcagat taatgactta ggaaatctat      60
taatgtaatt caccgcatta acagattaaa ggaaaaacat gattatctaa atggatgcag    120
aaaaagcatt tgataacatc taatattcat tcataattgt aaatgttt                  168
```

```
<210> SEQ ID NO 31
<211> LENGTH: 158
<212> TYPE: DNA
<213> ORGANISM: Macaca sp.

<400> SEQUENCE: 31
agtctggttt gtcccagaaa tgcactttag cagattaatg acttaggaaa tctattaatg      60
taattcactg cattaacaga ttaaaggaaa aacatgatta tctaaatgga tgcagaaaaa     120
gcatttgata atatctaata ttcattcata attttaaa                             158
```

MODULATION OF NEURAL PATHWAYS

CROSS REFERENCE

This application is a continuation of U.S. non-provisional patent application Ser. No. 13/879,004, which was file Nov. 22, 2013, a national stage entrant of international patent application PCT/US2011/056475 under 37 U.S.C. § 371, which was filed Oct. 14, 2011, and which claimed the benefit of U.S. provisional patent application 61/393,779, which was filed Oct. 15, 2010, and U.S. provisional patent application 61/393,787, which was filed Oct. 15, 2020, all of which applications are herein incorporated by reference in their entireties for all purposes.

The instant application contains a Sequence Listing which has been submitted electronically in ASCII format and is hereby incorporated by reference in its entirety. Said ASCII copy, created on Mar. 19, 2020, is named H1707675.txt and is 8.7 kilobytes in size.

STATEMENT AS TO FEDERALLY SPONSORED RESEARCH

This invention was made with the support of the United States government by the National Eye Institute (Grant No. 1R43EY019201, SBIR Grant).

BACKGROUND OF THE INVENTION

One method of controlling the specificity of gene expression is by using particular regulatory sequences, such as promoter sequences from a target tissue of interest. Many available promoters are ubiquitous in their expression control, resulting in high expression intensities. However, such ubiquitous promoters lack cell-type specificity. Regulatory sequence analysis and development for cell-specific promoters can be a long, arduous, and expensive process.

There is a need in the field for efficacious and specific gene therapeutic vectors capable of delivering gene therapies for human diseases or disorder.

INCORPORATION BY REFERENCE

All publications, patents, and patent applications mentioned in this specification are herein incorporated by reference for all purposes and to the same extent as if each individual publication, patent, or patent application was specifically and individually indicated to be incorporated by reference. The following applications are among the references herein incorporated by reference in their entirety: International Application No. PCT/US09/44753; U.S. Provisional Application No. 61/251,406; U.S. Provisional Application No. 61/200,430; U.S. Provisional Application No. 61/199,241; U.S. Provisional Application No. 61/105,685; U.S. Provisional Application No. 61/267,374, and U.S. Provisional Application No. 61/054,571.

SUMMARY OF THE INVENTION

Provided herein are methods and compositions for a high-throughput approach to design and use synthetic regulatory sequences that allow for targeted expression to specific cells of the central and peripheral nervous system, including neural cells and non-neural cells. Also provided herein are methods and compositions for controlling gene expression in cells of a variety of neural pathways, in particular the visual pathway, using synthetic gene regulatory sequences, for example regulatory promoters.

In some aspects, this disclosure provides a recombinant nucleic acid comprising a nucleic acid encoding a light-sensitive protein operatively linked to a GRM6 regulatory sequence, wherein said GRM6 regulatory sequence is at least 70% identical to SEQ ID NO:1. In some other aspects, this disclosure provides a recombinant nucleic acid comprising a nucleic acid encoding a light-sensitive protein operatively linked to a GRM6 regulatory sequence, wherein said GRM6 regulatory sequence promotes gene expression in retinal cone bipolar cells. In still further aspects, this disclosure provides a recombinant nucleic acid comprising a nucleic acid encoding a light-sensitive protein operatively linked to a GRM6 regulatory sequence, wherein said GRM6 regulatory sequence comprises a sequence that is at least 95% identical to at least one of the sequences in SEQ ID NOs:2-11.

In some embodiments, when the recombinant nucleic acid is introduced into the retina of a subject, greater than 80% of cells that express said light-sensitive protein are retinal ON bipolar cells. In other embodiments, when the recombinant nucleic acid is introduced into the retina of a subject, greater than 80% of cells that express said light-sensitive protein are retinal ON cone bipolar cells. In still further embodiments, when the recombinant nucleic acid is introduced into the retina of a subject, less than 20% of cells that express said light-sensitive protein are retinal OFF rod bipolar cells. In still other embodiments, said GRM6 regulatory sequence is human GRM6 regulatory sequence. In some embodiments, said light-sensitive protein is selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, Cheta, ChR65, C1V1, melanopsin, and variants thereof. In some cases, said light-sensitive protein is ChR2 or a light-sensitive protein that is at least 70% identical to ChR2. In some cases, said GRM6 regulatory sequence comprises less than 500 base pairs.

In some cases, the recombinant nucleic acid further comprises a green fluorescent protein. In some cases, the nucleic acid is encapsidated within a recombinant adeno-associated virus (AAV). In some cases, the recombinant adeno-associated virus is of a serotype selected from the group consisting of AAV1, AAV2, AAV3, AAV4, AAV5, AAV6, AAV7, AAV8, AAV9, AAV10, AAV11, AAV12, and hybrids thereof. In some embodiments, the recombinant adeno-associated virus is of a serotype selected from the group consisting of AAV2, AAV5, AAV7, AAV8, and hybrids thereof. In some embodiments, said recombinant AAV virus comprises a mutated capsid protein (e.g., mutated tyrosine residue).

In some aspects, the composition comprises a vector comprising a recombinant nucleic acid described herein. In some embodiments, said vector comprises at least two identical copies, or near-identical copies, of a recombinant nucleic acid described herein.

In some aspects, the method comprises a method of treating a subject having a disease or disorder of the eye comprising introducing into an affected eye a recombinant adeno-associated virus (AAV) comprising a recombinant nucleic acid described herein. In some cases, the method comprises a method of specifically expressing a light-sensitive protein in retinal bipolar cone cells in a subject comprising introducing into an affected eye a recombinant adeno-associated virus (AAV) comprising a recombinant nucleic acid described herein.

In some aspects, this disclosure provides a method of manufacturing a synthetic regulatory element that targets a specific cell type comprising: a. profiling the expression of a plurality of genes in at least one positive target cell (PTC) and at least one negative target cell (NTC), thereby obtaining a set of expression data; b. analyzing said set of expression data of step (a) in order to identify at least one regulatory motif in said at least one positive target cell that activate gene expression; c. analyzing said set of expression data of step (a) in order to identify at least one regulatory motif in said at least one negative target cell that inhibits gene expression; and d. constructing a polynucleotide that comprises said at least one regulatory motif of step (b) or said at least one regulatory motif of step (c).

In some embodiments, said at least one negative target cell is a cell that neighbors said at least one positive target cell. In some embodiments, said at least one negative target cell is a cell type that is different than said at least one positive target cell. In some embodiments, said at least one negative target cell is derived from the same tissue type as said at least one positive target cell. In some embodiments, said at least one negative target cell is derived from the same organ type as said at least one positive target cell. In some embodiments, said at least one negative target cell and said at least one positive target cell are derived from eye tissue. In some embodiments, said at least one negative target cell and said at least one positive target cell are derived from retinal tissue. In some embodiments, said at least one negative target cell or said at least one positive target cell is selected from the group consisting of: retinal bipolar cell, retinal OFF bipolar cell, retinal ON bipolar cell, retinal rod bipolar cell, retinal cone bipolar cell, retinal amacrine cell, photoreceptor cell, ganglion cell, cone cell, rod cell, horizontal cell, or retinal pigment epithelium (RPE) cell.

In some embodiments, said at least one positive target cell is a retinal ON bipolar cell and said negative target cell is selected from the group consisting of: retinal OFF bipolar cell, retinal rod bipolar cell, retinal cone bipolar cell, retinal amacrine cell, photoreceptor cell, ganglion cell, horizontal cell, cone cell, rod cell, or retinal pigment epithelium. In some embodiments, said at least one negative target cell is at least three (or at least 2, 4, 5, 6, 7, 8, 9, or 10) negative target cells, each of a different cell type. In some embodiments, said at least one positive target cell is at least three (or at least 2, 4, 5, 6, 7, 8, 9, or 10) positive target cells, each of a different cell type. In some embodiments, said at least one positive cell and said at least one negative cell are derived from healthy tissue.

In some embodiments, said at least one positive cell and said at least one negative cell are derived from tissue that has a disease or disorder. In some embodiments, said disease or disorder is a disorder of the eye that causes visual impairment. In some embodiments, said disease or disorder is macular degeneration or retinitis pigmentosa (or other disease or disorder, including a disease or disorder described herein).

In some embodiments, said at least one regulatory motif of step (b) is at least two regulatory motifs (or at least 3, 4, 5, 6, 7, 8, 9, or 10 regulatory motifs). In some embodiments, said at least one regulatory motif of step (c) is at least two regulatory motifs (or at least 3, 4, 5, 6, 7, 8, 9, or 10 regulatory motifs).

In some embodiments, said at least one regulatory motif of step (b) is associated with at least a two-fold increase in gene expression. In some embodiments, said at least one regulatory motif of step (c) is associated with at least a two-fold decrease in gene expression. In some embodiments, said at least one regulatory motif of step (b) is associated with at least a two-fold decrease in gene expression. In some embodiments, said at least one regulatory motif of step (c) is associated with at least a two-fold increase in gene expression. In some embodiments, said at least two-fold increase in gene expression is an at least two-fold increase when compared to average gene expression of said gene over multiple cell types. In some embodiments, said at least two-fold decrease in gene expression is an at least two-fold decrease when compared to average gene expression of said gene over multiple cell types. In some embodiments, said set of expression data is normalized against a set of data from a control gene (or from more than one control gene). Examples of control genes include, but are not limited to: beta actin, GAPDH, housekeeping genes, etc.

In some embodiments, said at least one positive target cell and said at least one negative target cell are derived from the same species of organism. In some embodiments, said at least one positive target cell and said at least one negative target cell are derived from different species of organism. In some embodiments, said polynucleotide of step (d) comprises multiple identical or near-identical copies of said regulatory motif of step (b) or said regulatory motif of step (c). In some embodiments, said polynucleotide of step (d) comprises at least one activating regulatory motif and at least one inhibitory regulatory motif. In some embodiments, said polynucleotide of step (d) comprises at least 1, 2, 3, 4, 5, 6, 7, 8, or 9 activating regulatory motifs and at least ol, 2, 3, 4, 5, 6, 7, 8, or 9 inhibitory regulatory motifs.

In some embodiments, said polynucleotide of step (d) comprises said at least one regulatory motif of step (b) and said at least one regulatory motif of step (c). In some embodiments, the method further comprises adding at least one regulatory motif of step (c) to the polynucleotide of step (d), if said polynucleotide of step (d) activates gene expression in said NTC.

In some aspects, this disclosure provides a method of manufacturing a synthetic regulatory element targeted to a cell type comprising: a. obtaining a first set of gene expression data of a gene in a first cell type;

b. obtaining a second set of gene expression data of said gene in a second cell type; c. analyzing said gene expression data of steps (a) and (b) to determine if said gene is differentially expressed in said first cell type in comparison to said second cell type; and d. constructing a polynucleotide that comprises a regulatory sequence of said gene if the analysis in step (c) indicates that said gene is differentially expressed in said first cell type in comparison to said second cell type. In some embodiments, said first cell type is different from said second cell type. In some embodiments, said first and second cell types are neural cells. In some embodiments, first and second cell types are cells of the eye. In some embodiments, said first cell type is a retinal bipolar ON cell. In some embodiments, said second cell type is a retinal bipolar OFF cell. In some embodiments, the method further comprises quantifying the differential expression in said first cell type compared to said second cell type. In some embodiments, said gene is expressed in said first cell type at a level that is at least three-fold higher (or at least 2, 3, 4, 5, 6, 7, 8, 9, 10, 50, 100, 500, 1000, 5000, 10000-fold higher) than the level of its expression in said second cell type. In some embodiments, said first cell type is a positive target cell. In some embodiments, said second cell type is a negative target cell.

In some embodiments, provided herein is a method of expression profiling of the transcription start sites (TSS) and their associated promoters in different retinal cell types using cap analysis of gene expression (CAGE), combined with second generation sequencing.

In another embodiment, provided herein is a computational tool to optimize a synthetic regulatory sequence for targeted expression in different populations of neural cells, for example retinal cells, for example in retinal ON or OFF bipolar cells.

In yet another embodiment, provided herein are compositions and methods to determine expression efficacy and specificity using a high-throughput organotypic slice culture methodology, for example specifically a retinal slice culture methodology.

In a related embodiment, provided herein are compositions and methods to design synthetic regulatory sequences to allow selective ChR2 or NpHR transgene expression to 5 different populations of retinal cells. In one aspect the transgene is selected from ChR1, ChR2, ChIEF, ChETA (ChR2 with a double point mutation, C123T/E134R), Arch, ArchT, Mac, NpHR, enhanced NpHR, VChR1, halorhodopsin (halo), and melanopsin (Opn4). In one specific aspect, the synthetic regulatory sequence allows selective expression in three different populations of OFF bipolar cells, and three different populations of OFF retinal bipolar cells.

In a related embodiment a light-sensitive protein is specifically expressed in a subject in ON bipolar cells. In one aspect the light-sensitive protein is specifically expressed in ON bipolar cells using a cell-type specific regulatory sequence. In a related aspect, the cell-type specific regulatory sequence is derived from or is related to GRM6 promoter sequence. In another aspect, the cell-type specific regulatory sequence is synthetic. In one aspect, the light-sensitive protein is chosen from ChR1, ChR2, ChIEF, ChETA (ChR2 with a double point mutation, C123T/E134R), Arch, ArchT, Mac, NpHR, enhanced NpHR, VChR1, halorhodopsin (halo), and melanopsin (Opn4). In a preferred embodiment, the light-sensitive protein is the photosensitive cation channel channelrhodopsin-2 (ChR2). In one aspect the subject is blind. In a related aspect, there is at least about 50%-70% transduction efficiency of ON bipolar cells using the specific regulatory sequence. In a related embodiment, the light-sensitive protein is delivered using a gene therapeutic vector. In one aspect the therapeutic vector is an adeno-associated viral (AAV) vector.

In another related embodiment a light-sensitive protein is specifically expressed in a subject in one of three types OFF bipolar cells: 1) Type 1 and 2 OFF bipolar, 2) Type 3 OFF bipolar, and/or 3) the entire population of OFF bipolar cells, including Type 4. In one aspect the light-sensitive protein is specifically expressed in OFF bipolar cells using a cell-type specific regulatory sequence. In another aspect, the cell-type specific regulatory sequence is synthetic. In one aspect, the light-sensitive protein is chosen from ChR1, ChR2, ChIEF, ChETA (ChR2 with a double point mutation, C123T/E134R), Arch, ArchT, Mac, NpHR, enhanced NpHR, VChR1, halorhodopsin (halo), and melanopsin (Opn4). In a preferred embodiment, the light-sensitive protein is the photosensitive ArchT). In one aspect the subject is blind. In a related aspect, there is at least about 50%-70% transduction efficiency of OFF bipolar cells using the specific regulatory sequence. In a related embodiment, the light-sensitive protein is delivered using a gene therapeutic vector. In one aspect the therapeutic vector is an AAV vector.

In yet another related embodiment, ChR2 and NpHR are dually but selectively targeted to ON bipolar cells, and OFF bipolar cells, respectively, using synthetic regulatory regions. In a specific embodiment, the therapeutic transgenes ChR2 and NpHR are delivered using AAV recombinant viral vectors. In a related embodiment, this dual transgene targeted delivery is provided to a subject suffering from a visual impairment, for example blindness, and such treatment restores visual light sensitivity in the subject.

In yet another related embodiment, ChIEF and ArchT are dually but selectively targeted to ON bipolar cells, and OFF bipolar cells, respectively, using synthetic regulatory regions. In a specific embodiment, the therapeutic transgenes ChIEF and ArchT are delivered using AAV recombinant viral vectors. In a related embodiment, this dual transgene targeted delivery is provided to subject suffering from a visual impairment, for example blindness, and such treatment restores visual light sensitivity in the subject.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4(A) discloses SEQ ID NOs 28-31, respectively, in order of appearance. (B) shows an evolutionarily conserved region (ECR) map between rat, mouse, macaque, and human and shows the high conservation of the 200 bp GRM6 enhancer upstream of GRM6 exon 1.

DETAILED DESCRIPTION OF THE INVENTION

Overview

Figure 1:
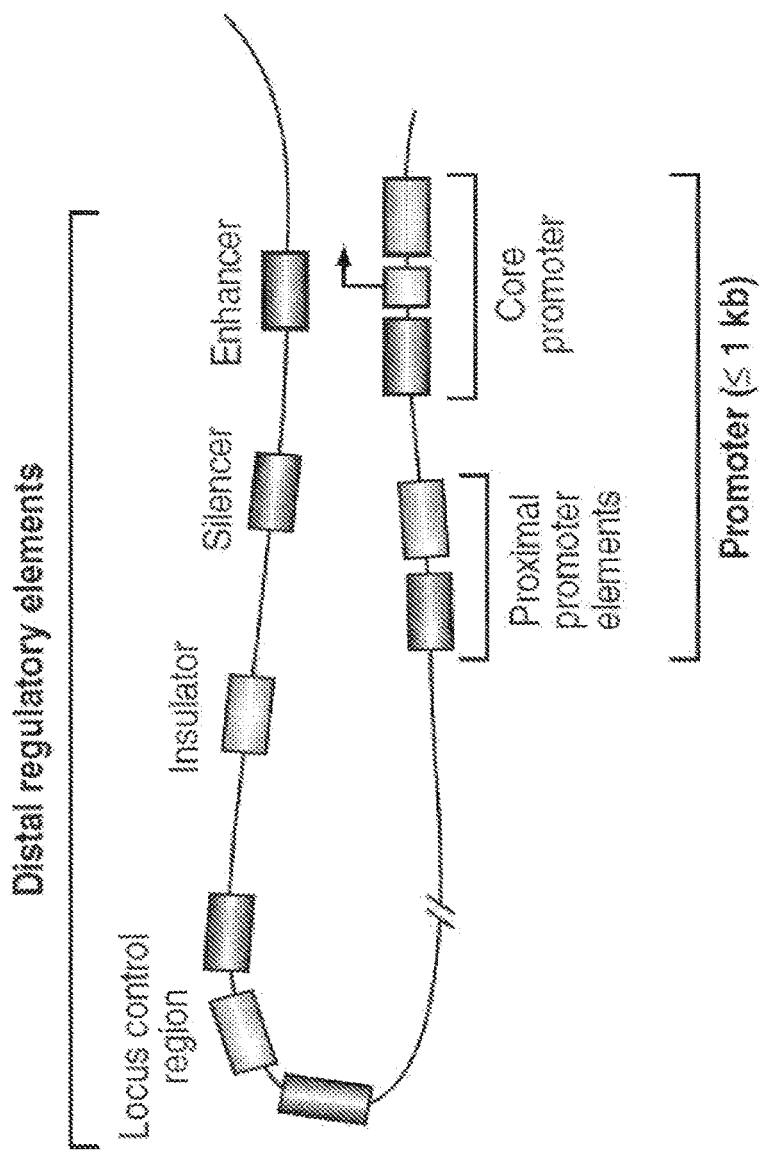
FIG. 1 shows a schematic of a gene regulatory region (5' of the gene). The promoter including the core and proximal promoter elements, is a region that spans 200 bp to 2 kb. Upstream regulatory elements (i.e., locus control regions, insulators, silencers, and enhancers) can be located up to 1 Mb from the promoter region. These distal elements, however, may come in contact with the promoter region through a mechanism that involves looping out the intervening DNA (adapted from Maston, G A, Evans, S K, and Green, M R (2006). *Annu Rev Genomics Hum Genet* 7: 29-59.).

This disclosure provides methods and compositions that enable the regulation of expression of polynucleotides (e.g., RNA, mRNA, miRNA, etc.) and/or polypeptides in a cell-type specific manner. The cell types can be any cell type, but in some embodiments the cell type is a neural cell, a neuron or a cell that is involved in vision (e.g., eye cell, retinal cell, bipolar cell, retinal ON bipolar cell, retinal OFF bipolar cell, photoreceptor cell, cone cell, rod cell, horizontal cell, amacrine cell, retinal rod bipolar cell, retinal cone bipolar cell, retinal pigment epithelium (RPE) cell, etc.).

In some cases, this disclosure provides methods of generating synthetic promoters that cause negative or positive regulation of a gene of interest in a specific cell type. The regulatory regions may be identified by analyzing gene expression, protein expression, transcriptomes, or proteomes (or subsets thereof) in a cell-type specific manner. In some cases, a gene of interest is identified to be upregulated in a particular cell-type (e.g., an ON bipolar cell) and is flagged to be of continued interest if it is observed to be down-regulated in a particular cell-type (e.g., an OFF bipolar cell). In some cases, a gene of interest is identified to be upregulated in a particular cell-type (e.g., an ON bipolar cell) and is flagged to be of continued interest if it is observed to be also up-regulated in a different cell-type or species of cell. In some cases, a gene of interest is identified to be downregulated in a particular cell-type (e.g., an ON bipolar cell) and is flagged to be of continued interest if it is observed to be upregulated in a different cell-type. In some cases, a gene of interest is identified to be downregulated in a particular cell-type and is flagged to be of continued interest if it is observed to be down-regulated in a different cell-type. The data regarding the up- or down-regulation of the gene of interest may also take into account other variables, such as the degree of up- or down-regulation, the consistency of the up- or down-regulation across different experimental models, whether the up- or down-regulation occurs in other cell-types (such as related cell types, or cell types likely to be in close physical proximity to the targeted cell type).

In some cases, a set of cell-types or tissue types is subjected to gene expression profiling and the data is analyzed in order to obtain regulatory motifs that activate or inhibit (or have no effect on) gene expression in a cell type of interest (or a cell that has been subjected to a condition, as described further herein). A synthetic regulatory element (SRE)(as described further herein) may be generated that comprises an activating regulatory motif and/or an inhibitory regulatory motif, or combinations of activating and inhibitory regulatory motifs.

A synthetic promoter may be generated that incorporates the regulatory sequence of a gene of interest, or of a set of genes of interest. In some cases, the synthetic promoter is incorporated into a vector, and/or is operably linked to a polynucleotide encoding a light-sensitive protein, or other protein involved in visual processes. In some cases, the synthetic promoter is developed after applying an algorithm that compares gene expression (e.g., RNA, mRNA, protein, etc.) levels across multiple different cell types. In some cases, the algorithm also incorporates data from different organisms (e.g., organisms such as humans, mammals, primates, non-human primates, apes, monkeys, macaques, rodents, mice, rabbits, rats, reptiles, alligators, lizards, microbes, etc.). In some cases, the algorithm compares data across different species, while in other cases, the algorithm performs intra-species comparisons.

This disclosure also provides sequences of synthetic regulatory elements. For example, this disclosure provides the sequence of regulatory elements for the human hGRM6 gene (which encodes the mGluR6 protein), as well as vectors that comprise combinations of such regulatory elements. This disclosure further provides methods of controlling gene expression in specific cell types, particularly a method of specifically targeting gene expression to a specific cell type (e.g., a cone bipolar cell as opposed to a rod bipolar cell).

This disclosure also provides methods of targeting multiple cell types in the eye. For example, in some cases, a method may comprise introducing a particular light-sensitive protein (e.g., ChR2) to an ON bipolar cell and a second light sensitive protein (e.g., NpHR2) to an OFF bipolar cell at the same time, or nearly the same time.

Synthetic Regulatory Elements

Provided herein are methods and compositions to generate synthetic regulatory elements (SREs) that can be used to regulate gene expression in a cell-type specific manner. Often, an SRE described herein is generated after the use of an algorithm to identify cell-type specific regulatory elements. The methods and compositions herein can be used to identify regulatory motifs for specific cell types of the nervous system (e.g., neural cells, central or peripheral nervous system cells, neurons) or of the visual system (e.g., eye cell, retinal cell, retinal ganglion cell, ganglion cell, photoreceptor cell, amacrine cell, bipolar cell, retinal ON bipolar cell, retinal OFF bipolar cell, retinal rod bipolar cell, retinal cone bipolar cell, rod cell, cone cell, horizontal cell, retinal pigment epithelium (RPE) cell etc.). In some cases, the methods and compositions provided herein are used to identify regulatory motifs in neuronal cells or non-neuronal cells. In some cases, the methods and compositions provided herein are used to identify regulatory motifs in sets of different tissues, organs, or sets of different cell types. In some cases, the methods and compositions provided herein are used to identify regulatory motifs (activating or inhibiting) that are active in healthy tissue (e.g., eye, retina, heart, lung, skin, blood, pancreas, liver, spleen, brain, nervous system, central nervous system, peripheral nervous system, thymus, thyroid, reproductive system, uterus, breast, prostate, etc.); while in other cases, the methods and compositions provided herein are used to identify regulatory motifs (activating or inhibiting) that are active in tissue that has a disease or disorder (e.g., disease of the eye, macular degeneration, retinitis pigmentosa, or disease of any other organ or organ system, e.g., heart, lung, skin, blood, pancreas, liver, spleen, brain, nervous system, central nervous system, peripheral nervous system, thymus, thyroid, reproductive system, uterus, breast, prostate, etc.)

In some embodiments, a SRE activates gene expression in a certain cell type (or set of cell types). In some embodiments, a SRE inhibits gene expression in a certain cell type (or set of cell types). In some embodiments, a SRE has no effect, or a negligible effect, on gene expression in a certain cell type (or set of cell types). In some cases, a SRE activates gene expression in a certain cell type (or set of cell types) and inhibits gene expression in a different cell type (or set of cell types). In some cases, a SRE activates gene expression in a certain cell type and inhibits gene expression in cells that neighbor that certain cell type (or a mixture of different cell types that neighbor that certain cell type). In some cases, a SRE activates gene expression in a certain cell type and has no effect on, or only a negligible effect on, gene expression in cells that neighbor that certain cell type. In some cases, a SRE activates gene expression in a positive cell type (e.g., retinal ON bipolar cell). In other cases, a SRE inhibits gene expression, or has only a negligible effect on gene expression, in a positive cell type. In some cases, a SRE activates gene expression in a negative cell type (e.g., retinal OFF bipolar cell). In other cases, a SRE inhibits gene expression, or has only a negligible effect on gene expression, in a negative cell type.

In some cases, a SRE activates, inhibits, or has no effect (or little effect) on gene expression in a set of cell types that are a subpopulation of cells. For example, the set of cell types may include different retinal cells (e.g., OFF bipolar cells, ON bipolar cells, bipolar cells, photoreceptor cells, amacrine cells, horizontal cells, rod cells, cone cells, retinal pigment epithelium (RPE) cells, etc., or any combination thereof), or different cells of the visual system, or sets of unrelated cell types. In some cases, the synthetic regulatory element activates gene expression in a certain cell type and inhibits gene expression in a different cell type.

A SRE may activate or inhibit gene expression at a certain level. For example, an SRE may activate gene expression of a specific gene such that the level of gene expression is increased by greater than 2-fold, 3-fold, 4-fold, 5-fold, 10-fold, 15-fold, 20-fold, 30-fold, 50-fold, 100-fold, 500-fold, 1000-fold, 5000-fold, or 10,000-fold the basal level of gene expression for the gene in a specific cell type (or the average level of gene expression of the gene across several cell types). In other cases, an SRE may inhibit gene expression of a specific gene such that the level of gene expression is decreased by greater than 2-fold, 3-fold, 4-fold, 5-fold, 10-fold, 15-fold, 20-fold, 30-fold, 50-fold, 100-fold, 500-fold, 1000-fold, 5000-fold, or 10,000-fold compared to the basal level of gene expression for the gene in a specific cell type (or the average level of gene expression of the gene across several cell types).

In some embodiments, the SRE comprises at least 2, 3, 4, 5, 6, 7, 8, 9, 10, 11, 12, 13, 14, 15, or 20 regulatory elements. In some cases, the SRE comprises one or more regulatory motifs that activate gene expression in a Positive Target Cell (PTC). In some cases, SRE comprises one or more regulatory motifs that inhibit gene expression in a Negative Target Cell (NTC). In some cases, the SRE comprises at least 2, 3, 4, 5, 6, 7, 8, 9, 10, 11, 12, 13, 14, 15, or 20 regulatory motifs that activate gene expression in a Positive Target Cell (PTC). In some cases, SRE comprises at least 2, 3, 4, 5, 6, 7, 8, 9, 10, 11, 12, 13, 14, 15, or 20 regulatory motifs that activate gene expression in a Negative Target Cell (NTC). In some cases, the SRE comprises at least 1, 2, 3, 4, 5, 6, 7, 8, 9, 10, 11, 12, 13, 14, 15, or 20 regulatory elements that inhibit gene expression in a PTC. In some cases, the SRE comprises at least 1, 2, 3, 4, 5, 6, 7, 8, 9, 10, 11, 12, 13, 14, 15, or 20 regulatory elements that activate gene expression in a NTC.

Generally, SREs comprise regulatory elements that can activate gene expression in PTCs and inhibit (or have no effect) on gene expression in NTCs. However, in some cases, an SRE may comprise regulatory elements that inhibit (or have little to no effect on) gene expression in PTCs and activate gene expression in NTCs.

PTCs are generally target cells of interest, and usually are of a specific cell type, or have been subjected to a specific condition. NTCs are generally cells that are not being targeted. In some cases, NTC is a cell type or collection of cell types that neighbor a PTC. In some cases, NTCs and PTCs are of the same cell type, or are different cell types that are derived from the same tissue type, organ, organ system, location in the body, or species of organism. In other cases, NTCs and PTCs are derived from different tissues, different organs, different organ systems, different locations in the body, or from different species.

In some cases, the PTC is derived from a tissue (e.g., retinal tissue), and the NTC is derived from a different tissue (e.g., brain tissue). In some cases, the PTC is derived from retinal tissue (e.g., retinal ON bipolar cells) while the NTC includes a cell or cells from a different cell type (or types) within retinal tissue (e.g., retinal bipolar cell, retinal OFF bipolar cell, retinal rod bipolar cell, retinal cone bipolar cell, retinal amacrine cell, photoreceptor cell, ganglion cell, cone cell, rod cell, horizontal cell, or retinal pigment epithelium (RPE) cell.). In some cases, the PTC or NTC is derived from retinal tissue selected from: retinal bipolar cell, retinal OFF bipolar cell, retinal ON bipolar cell, retinal rod bipolar cell, retinal cone bipolar cell, retinal amacrine cell, photoreceptor cell, ganglion cell, cone cell, rod cell, horizontal cell, or retinal pigment epithelium (RPE) cell.

In some cases, the NTCs are at least 1, 2, 3, 4, 5, or 6 different cell types selected from: retinal bipolar cell, retinal OFF bipolar cell, retinal ON bipolar cell, retinal rod bipolar cell, retinal cone bipolar cell, retinal amacrine cell, photoreceptor cell, ganglion cell, cone cell, rod cell, horizontal cell, or retinal pigment epithelium (RPE) cell.

In some cases, the PTCs are at least 1, 2, 3, 4, 5, or 6 different cell types selected from: retinal bipolar cell, retinal OFF bipolar cell, retinal ON bipolar cell, retinal rod bipolar cell, retinal cone bipolar cell, retinal amacrine cell, photoreceptor cell, ganglion cell, cone cell, rod cell, horizontal cell, or retinal pigment epithelium (RPE) cell.

In some cases, the PTC and the NTC are both derived from healthy tissue. In other cases, one or both the PTC and the NTC are derived from tissue with a disease or disorder (as described further herein, e.g., retinal tissue from an animal with a visual impairment). In some cases, the PTC and NTC are made up of a combination of healthy cells and cells with a disease or disorder. In some cases, the PTC and/or NTC is exposed to a condition (e.g., light adaptation, dark adaption, etc.). In some cases, the PTC is exposed to a condition (e.g., light adapted), and the NTC is exposed to a different condition (e.g., dark adapted).

In some embodiments, the SRE comprises a combination of regulatory motifs, at least one of which activates gene expression in a PTC and at least one of which inhibits gene expression in a NTC. In some embodiments, the SRE comprises a combination of regulatory motifs, at least one of which inhibits gene expression in a PTC and at least one of which activates gene expression in a NTC. In some cases, the SRE may comprise at least 2, 3, 4, 5, 6, 7, 8, 9, 10, 11, 12, 13, 14, 15, or 20 regulatory motifs that activate gene expression in a PTC and at least 2, 3, 4, 5, 6, 7, 8, 9, 10, 11, 12, 13, 14, 15, or 20 regulatory motifs that inhibit gene expression in a NTC.

A SRE described herein may also be used in combination with other regulatory elements. For example, a vector may comprise an SRE and other regulatory elements, such as a regulatory element that works synergistically with the SRE, or antagonistically with the SRE. In some cases, the vector (or the SRE) comprises additional regulatory elements including but not limited to: enhancer, silencer, locus control region, proximal promoter, or core promoter. (See FIG. 1). A core promoter can be any promoter known in the art (e.g., cmv promoter, sv40 promoter). In some cases, the core promoter comprises enhancer or silencer binding site motifs, and/or transcription start site(s) (TSS). Often, the core promoter drives transcription, while an upstream regulatory element, such as an SRE described herein, controls cell-type specificity.

In general, a SRE is a polynucleotide such as DNA, RNA, cDNA, mRNA, miRNA, cRNA, etc. However, in some embodiments, regulatory elements that are not polynucleotides are provided. For example, the compositions and methods provided herein also include polypeptides, macromolecule, chemicals, polymers, etc., especially polypeptides, macromolecules, chemicals, polymers, etc., capable of binding to a regulatory motif described herein. Such polypeptides, macromolecules, etc., may activate or inhibit gene expression in a specific cell type, and may also be incorporated into a vector and introduced into a subject, e.g., a subject with impaired vision.

In some embodiments, a SRE comprises a human GRM6 regulatory element (e.g., a hGRM6 element described herein). In some cases, a SRE comprises at least one human GRM6 regulatory element. In some cases, a SRE comprises at least 2, 3, 4, 5, 6, 7, 8, 9, or 10 different human GRM6 regulatory element. In some cases, a SRE comprises at least 2, 3, 4, 5, 6, 7, 8, 9, or 10 identical copies (or near-identical copies) of human GRM6 regulatory element.

Often, a SRE described herein is prepared and then refined through a series of steps. For example, an SRE is generated to include a regulatory motif that activates gene expression in a positive target cell (PTC) but, after experimentation, is found to also highly or minimally activate gene expression in a negative target cell (NTC). The SRE may then be further engineered to include a negative regulatory element that inhibits gene expression in the NTC. The negative regulatory element may also cause a small or large amount of inhibition of gene expression in the PTC. The SRE then may be further engineered to include an additional activating regulatory motif, either a copy of the original activating regulatory motif, or a new one. Variations of such steps may also be used in the methods and compositions provided herein.

This disclosure provides methods of manufacturing a synthetic regulatory element that targets a specific cell type. In some cases, the method comprises: a. profiling the expression of a plurality of genes in at least one positive target cell (PTC) and at least one negative target cell (NTC), thereby obtaining a set of expression data; b. analyzing said set of expression data of step (a) in order to identify at least one regulatory motif in said at least one positive target cell that activate gene expression; c. analyzing said set of expression data of step (a) in order to identify at least one regulatory motif in said at least one negative target cell that inhibits gene expression; and d. constructing a polynucleotide that comprises said at least one regulatory motif of step (b) or said at least one regulatory motif of step (c).

Regulation of Transcription

Much of the phenotypic diversity observed between adult mammalian cells is created by a program of transcriptional regulation that is encoded in the genome and executed in a precisely timed and regulated manner through development. The developmental path of each cell type culminates in a terminal cell type-specific pattern of gene expression that remains stable and robust by continual regulation. Though post-transcriptional and post-translational regulatory mechanisms do exist, the specific functions and behaviors that define each terminally differentiated cell type can largely be attributed to their unique transcriptomes.

Transcription is regulated through the interaction of transcription factor proteins (TFs) with specific binding sites (called TFBS or regulatory elements) that generally reside near the 5' end of the gene where transcription begins. TFBS are generally 8-10 bases in length, but can be shorter (e.g. members of the bHLH family) or much longer (e.g. multidomain ZNF proteins). The DNA binding domain (DBD) of each TF usually determines the sites to which the TF functionally binds; variation in these sites can change binding affinity, which can result in distinct requirements on nuclear TF concentration for regulating different genes. The set of transcription factors present in a cell nucleus largely determines which genes will be expressed and the intensity of expression.

Promoters are genomic regulatory sequences at the 5' end of a transcript that are dense in regulatory elements. Promoters both contain and define the transcription start sites (TSS) of genes. The sequence immediately surrounding the TSS is called the core promoter (~100 bp), and is recognized by the RNA polymerase II (PolII) complex, which performs the mechanical function of transcribing a gene as a first step in gene expression. Extending up and downstream from the core promoter is the proximal promoter region, which varies in size between genes (~200-2000 bp). Both the core and proximal promoter regions are dense in TFBS, but the proximal promoter generally contains a higher proportion of elements that provide cell specificity. The work of TFs may be summarized as assisting the PolII complex to form stably and start transcribing at exactly the appropriate promoters. The set of binding sites present in regulatory regions of each gene may be viewed as encoding their individual regulatory programs.

Enhancers are another kind of genomic regulatory sequence. Enhancers contain regulatory elements, but differ from promoters in two ways. First, enhancers are not contiguous with the promoter, but instead may function from a distance (potentially a very large distance) and be separated from the TSS by much non-regulatory sequence. The original defining property of an enhancer is that experimental manipulation to relocate or reorient the enhancer relative to the promoter generally does not affect the function of the enhancer. Second, a single enhancer may function on more than one gene.

Silencers are sequence-specific elements that confer a silencing or repressive effect on the transcriptional process. They typically function independently of the orientation of position of the promoter. As with enhancers, silencers can be located several kb upstream of the promoter. Insulators (also known as boundary elements) function to block genes from being affected by the transcriptional activity of neighboring genes. They thus limit the action of transcriptional regulatory elements to defined domains, and partition the genome into discrete realms of expression. Insulators have two main properties: (a) they can block enhancer-promoter communication (i.e., enhancer-blocking activity), and (b) they can prevent the spread of repressive chromatin.

In higher eukaryotes, transcription factors can work synergistically or antagonistically to achieve the proper regulatory function. Many transcription factors form dimers (homo-dimers or hetero-dimers), and additionally many transcription factors work together as larger complexes. This results in organizational requirements on the corresponding binding sites: steric constraints imposed by the TFs may stipulate that functional sites have particular distances, order and orientation relative to each other. The term cis-regulatory module is frequently used in reference to sets of functionally interacting TFBS. However, some systems of interacting transcription factors appear to function regardless of site order or orientation. The organizational requirements of interacting sites therefore appear to be system-specific. In some embodiments, this disclosure provides methods of obtaining sets of transcription factors that work synergistically or antagonistically; this disclosure also provides for generating synthetic regulatory elements that contain binding motifs for such sets of transcription factors.

Regulatory Motifs

The binding specificities of transcription factors (TFs) can be characterized using motifs, which, among other known methods in the art, can be represented as position-weight matrices (PWMs). Each column in a PWM provides the frequency of each base (A,C,G and T) appearing at the corresponding position in a binding site for the associated TF.

Given a set of sequences, each believed to contain a binding site for the same TF, a motif discovery task can be used to determine the identity of PWM that best characterizes binding specificity of the particular TF. One measure focuses on identifying motifs that are highly overrepresented in a set of sequences, based on some statistical measure. Another measure is relative overrepresentation, where desired motifs are overrepresented in one set of sequences (the foreground) when compared with another set (the background). The foreground set may be a set of promoters for over-expressed transcripts in some condition; the background set could be promoters of under-expressed transcripts in the same conditions. For example, in some cases, the foreground set is a set of promoters for over-expressed transcripts in normal or healthy tissue. In some cases, the background set is a set of promoters of under-expressed transcripts in normal or healthy tissue. The foreground may also be a set of promoters for over-expressed transcripts in positive target cells (PTCs), while the background is a set of promoters for under-expressed transcripts in negative target cells (NT Cs). In some cases, the foreground is a set of promoters for under-expressed transcripts in positive target cells (PTCs), while the background is a set of promoters for over-expressed transcripts in negative target cells (NTCs).

In some cases, the foreground set is a set of promoters for over-expressed transcripts in tissue that is diseased or has a disorder (e.g., a disease or disorder of the eye, macular degeneration, retinitis pigmentosa, neural disease, neurodegenerative disease, etc.). In some cases, the background set is a set of promoters of under-expressed transcripts in tissue that is diseased or has a disorder (e.g., a disease or disorder of the eye, macular degeneration, retinitis pigmentosa, etc.). In still other examples, the foreground set is derived from a specific species of organism (e.g., mice), while the background is derived from a different species of organism (e.g., rats). In still other examples, the foreground set may be derived from an organism, or tissue, that has been subjected to a specific condition (e.g., light adaption), while the background set is derived from the opposite condition (e.g., dark adaption). Other examples of conditions include but are not limited to: changes to diet (e.g., starvation, sugar-rich diet, fat-rich diet), stress, exercise, exposure to an infectious agent, etc.

Specifically, a discriminating matrix enumerator (DME) algorithm can be used to discover PWM-based motifs in large sets of regulatory sequences, with the property of relative overrepresentation. A motif with relative overrepresentation may be overrepresented in the foreground, underrepresented in the background, or both. If a motif is only slightly overrepresented in the foreground, but also slightly underrepresented in the background, then the relative overrepresentation can still be large Exemplary regulatory motifs that can be identified are those associated with neurons of the visual pathway, for example retinal cell types, specifically ganglion cells, ON bipolar cells, or OFF bipolar cells (and other cell types including those described herein). A DME algorithm can further be used to discover motifs for the cell types of interest. In a further embodiment, such identified motifs can be used to construct synthetic regulatory sequences, for example synthetic promoters, to achieve cell type specific, cell subtype specific, and tissue-specific differential expression of a transgene of interest. By way of example, a NpHR transgene, under the control of a synthetic regulatory promoter especially designed for specific expression in OFF but not ON bipolar cells, may drive expression in retinal OFF bipolar cells, but not in ON bipolar cells.

Methods of identifying regulatory elements (and corresponding transcription factors, or other types of regulatory molecules) are known in the art, see, e.g. Smith et al., (2006) *PNAS* 103(16):6275-6280; Smith et al., (2005) *PNAS* 102 (5):1560-1565; Schones et al., (2007) *BI\IC Bioinformatics* 8(19):1-11.

Expression Profiling

In some embodiments, the gene expression profiles of samples prepared from target cells of interest (e.g., positive target cells (PTCs), negative target cells (NTCs), retinal bipolar cells (including ON and/or OFF), neural cells, etc.), as well as the cells that neighbor the target cell, is an initial step in developing a functional synthetic promoter or other type of SRE. In general, when an SRE is introduced into a PTC, it activates expression of a gene to which it is operatively linked. Conversely, when an SRE is introduced into a NTC, it fails to activate (or minimally activates) expression of a gene to which it is operatively linked. However, in some cases, an SRE may inhibit gene expression in a PTC and activate gene expression in a NTC. In some embodiments, expression profiling is performed on sets of genes in PTC tissue and/or NTC tissue, or on greater than 10%, 20%, 30%, 40%, 50%, 60%, 70%, 80%, 90%, 95%, 97%, 99%, of expressed genes of a transcriptome, or on the entire transcriptome.

In some embodiments, microarrays are used for profiling gene expression in target cells of interest.

In another embodiment, RNA-seq or whole transcriptome shotgun sequencing (WTSS) using second-generation sequencing technology is used for profiling gene expression of a sample. A cap analysis of gene expression (CAGE) technique can determine the transcription start sites (TSSs) on a genome-wide scale by isolating and sequencing short sequence tags starting at the 5' end of RNA transcripts. When combined with second-generation sequencing, this technique is referred to as "deep CAGE", and can simultaneously identify TSSs used in a sample, and expression levels. CAGE relies on a cap-trapper system to capture full length RNA strands while avoiding rRNA and tRNA transcripts. First, an oligoT primer is used to reverse-transcribe poly(A)-terminated RNAs. RNA/DNA double-stranded hybrids that contain mature mRNA are selected by biotinylating their 5' cap structure, allowing for capture by streptavidin-coated magnetic beads. The linker sequences containing a MmeI recognition sites to the 5' end of the full-length cDNA are ligated to create a restriction site about 20 nucleotides downstream, producing a short CAGE tag starting at the 5' end of mRNAs{Kodzius, 2006 #3999}. These tags can map to 1) known genes that can be derived from the full-length mRNA and 2) currently unknown TSSs or genes. These short-sequence tags are generally more efficient at detecting TSSs than full-length sequenced mRNA. Using second generation sequencers, it is possible of generating many millions of tags from a single experimental condition. Specific tag counts allow for an accurate estimate of the cellular concentration of that specific mRNA. Deep CAGE can detect both the TSSs as well as the total expression level, making it a tool for evaluating transcriptional regulatory networks.

In one embodiment, provided herein are methods to evaluate the gene expression of different neural subpopulations. In a related embodiment, microarrays, CAGE or deep CAGE methods are utilized for such evaluation. In a specific embodiment, gene profiles of different subpopulations of cells of the visual pathway, for example of retinal cells are characterized using the deep CAGE method.

The methods and compositions provided herein can be used to analyze the transcriptional regulatory network of different cell subpopulations. The cell subpopulations can be different cell subpopulations of retinal cells, including but not limited to: retinal ganglion cells, retinal OFF bipolar cells, retinal ON bipolar cells, retinal rod bipolar cells, retinal ON cone bipolar cells, retinal OFF cone bipolar cells, Type 1 OFF bipolar cells, Type 2 OFF bipolar cells, Type 3 OFF bipolar cells, or Type 4 OFF bipolar cells, amacrine cells, photoreceptor cells, rod cells, cone cells, horizontal cells, retinal pigment epithelium (RPE) cells, or any combination thereof. In some embodiments, such methods are used to evaluate the transcriptional regulatory network subpopulations of retinal cells including, but not limited to: (i) retinal ganglion cells, (ii) rod and ON bipolar cells, (iii) Types 1 and 2 OFF bipolar cells, (iv) Type 3 bipolar cells, and (v) Type 4 bipolar cells. In some cases, all five of these subpopulations are evaluated; in other cases, a subset of these subpopulations is evaluated. In some embodiments, the methods and compositions described herein are used to expression profile three different subpopulations of retinal OFF bipolar cells (or any combination thereof): 1) Type 1 and 2 OFF bipolar, 2) Type 3 OFF bipolar, and 3) the entire population of OFF bipolar cells, including Type 4. In some embodiments, the methods and compositions described herein are used to expression profile different subpopulations of retinal ON bipolar cells (e.g., retinal rod bipolar cells; retinal cone ON bipolar cells; retinal ON bipolar cells, or any combination thereof). In some embodiments, the methods and compositions described herein are used to expression profile different subpopulations of retinal OFF bipolar cells (e.g., Type 1, Type 2, Type 3, Type, OFF cone bipolar cells, etc.)

In some embodiments, such expression profiling of retinal cells is carried out in an animal model of visual impairment, for example in a rd10 mouse model. Other exemplary animal models include mammals, non-human mammals, primates, non-human primates, apes, monkeys, macaques, rodents, mice, rabbits, rats, reptiles, alligators, lizards, microbes, etc. In some cases, human tissue may also be used. In some cases, the expression profiling involves a comparison of gene expression in cells from a visually-impaired animal with gene expression in cells from an animal with normal vision. In some cases, the animal has a genetic disease. In some cases, the animal has a photoreceptor disease. In some cases, the animal has glaucoma, macular degeneration, retinitis pigmentosa (or other disease of the eye, as described herein or known in the art).

Promoter Design

In some cases, an integrated experimental and/or computational method for designing synthetic promoters with regulatory specificity for a selected set of cell types (e.g., neural cells, retinal cells, bipolar cells) is developed. In a related embodiment, this method is applied to retinal cell types, for the purpose of expressing a therapeutic transgene, such as a light-sensitive transmembrane protein, in various retinal cells, including ON and/or OFF bipolar cells. Multiple strategies can be used for promoter design, including but not limited to, rational modifications to template promoters, designed regulation by specific TFs, and algorithmic promoter design.

Rational modifications to template promoters: The strategy of rational modifications to template promoters is based on a template natural promoter with some positive properties of specificity for positive target cells (PTCs) and intensity of regulated expression. The strategy involves modifying the template promoter in a way that improves both specificity and intensity, through rationally determined incremental changes. Information to guide the set of changes can come from comparison with homologous sequences. This approach depends on the availability of individual template promoters with the desired properties. The template promoters are taken from regulatory sequences associated with the marker genes of interest for a specific cell type. The regulatory sequence can include the promoter (for example 2000 bp, overlapping the TSS) and enhancer regions, identified computationally, proximal to the relevant genes. Often the regulatory sequences are present in cis relative to the gene of interest. Evaluating promoters designed using this strategy can indicate how to use information from cross-species comparisons, and to what degree this information is important.

Promoter templates for use in expression profiling and the rational modification method include, but are not limited to the exact template, a conserved template, a putative regulatory template, a non-reference species template, and modifications to any of these templates. These are described in more detail herein.

An exact template can provide a baseline level of expression, both in terms of specificity and intensity. For a conserved template, some or all non-conserved bases of a template are replaced at random with bases that appear at low frequency in the corresponding position of the alignment (and that do not appear in the reference species). For a putative regulatory template, TFs with specific binding sites (TFBS) identification is performed within the promoter, and all sites not included within a putative TFBS can be modified (as for the conserved template). For a non-reference species template a homologous primate and a homologous non-primate, non-rodent mammal are selected, with some minimum level of conservation (e.g. at least 33% identity) is present. This can provide information about translating from the model organism.

The modified template can be one of the templates described directly preceding, for example the exact template further modified with additional elements or replaced by particular elements, or appended elements.

Cross-species conservation is a method for identifying functional non-coding genomic elements and can be used for the described analyses.

In one embodiment, rational modification of a template is carried out on promoters known to express in retinal ganglion cells, retinal ON bipolar cells, and/or in retinal OFF bipolar cells. In a related embodiment, once the rational modification is carried out and the synthetic regulatory region is designed, a therapeutic protein of interest can be expressed under the control of the synthetic regulatory region to achieve specificity of expression in a desired cell type. The desired cell type can be neural or a non-neural cell. The therapeutic transgene can be ChR1, ChR2, ChIEF, ChETA (ChR2 with a double point mutation, C123T/E134R), Chr65, C1V1, Arch, ArchT, Mac, NpHR, enhanced NpHR, VChR1, halorhodopsin (halo), or melanopsin (Opn4), etc.

Design of promoters using known regulation by specific TFs: The strategy of promoter design using known regulation by specific transcription factors is based on designing a sequence that contains elements selected to bind a specific set of TFs. First an appropriate set of TFs for a given tissue or cell type of interest is identified. In some instances, this strategy involves understanding which genes are upregulated in expression, and which genes are downregulated for a given set of PTC and NTC tissue. Evaluating the regulatory sequences of highly upregulated genes, it may be possible to find reoccurring transcription factor binding site motifs that are generally associated with upregulation. These motifs may be synthetically combined in such a way as to boost the expression of a given transgene in the PTC. To direct cell specific targeting, transcription factor binding sites that are generally associated with downregulation in the NTCs will be synthetically combined with the PTC upregulating motifs to create a cell specific, highly expressing regulatory synthetic promoter. Promoters are then constructed by arranging the corresponding elements in random or strategic order immediately adjacent to a basal promoter. Both positive regulators specific to PTCs and negative regulators absent in NTCs are considered. Evaluating promoters designed using this strategy can indicate how best to use information about expression profiles of TFs, including both positive and negative regulators. A useful set of TFs, information about positive versus negative regulation, a priori information of binding affinities of TFs, knowledge about known homologs (with respect to binding domain and similar binding specificity) can aid in this strategy.

In some embodiments, knowledge about regulation by specific TFs in cells of the visual pathway, for example knowledge about TFs in retinal ganglion cells, retinal ON bipolar cells, and/or in retinal OFF bipolar cells, is used to design a synthetic regulatory sequence. In a related embodiment, once the synthetic regulatory region is designed, a therapeutic protein of interest can be expressed under the control of the synthetic regulatory region to achieve specificity of expression in a desired cell type. The desired cell type can be neural or a non-neural cell. The therapeutic transgene can be ChR1, ChR2, ChIEF, NpHR, eNpHR, VChR1, or melanopsin.

Algorithmic Design Strategy: The algorithmic design strategy can leverage information from sequence analysis to identify the appropriate elements for inclusion in the synthetic promoter, and, importantly, organization of those elements (i.e. relative order, spacing and orientation).

This strategy can generate promoters once initial expression data has been obtained. For example, once expression data and TSS locations have been obtained for a target cell type, sets of training promoters can be constructed. An exemplary set of training promoters for each target cell type can include four sets of genes and corresponding promoters: (1) up-regulated positive target promoters (up-PTPs); (2) down-regulated positive target promoters (down-PTPs); (3) up-regulated negative target promoters (up-NTPs); and (4) down-regulated negative target promoters (down-NTPs). Regulatory elements enriched in the up-PTPs relative to (a) down-PTPs and (b) promoters of genes expressed in NTCs (represented by up-NTPs) could be candidate activation elements. Conversely, regulatory elements enriched in down-NTPs relative to (a) up-NTPs and (b) down-PTPs could be candidate repressive elements. The strategy can incorporate test activating and repressing elements both separately and together.

In this strategy, synthetic promoters can be constructed by concatenating candidate regulatory elements, and the algorithmic tasks may involve identifying appropriate elements and the order in which they should be positioned.

Regulatory elements can exist as cis-regulatory modules, placing organizational restrictions that sets of elements need to likely satisfy if they are to have proper regulatory function. Organization generally refers to relative order, orientation (i.e. strand) and spacing of elements. In some embodiments algorithms for elucidating organizational features of regulatory elements by analyzing how the elements appear in natural promoters are generated and statistical measures of consistency for these organizational features are designed.

In this strategy, changes to the order of elements can occur so that varying degrees of order preservation can be modeled, for example, to allow broken order between two modules. Alignments can reflect inversions of consecutive sets of promoter elements, with penalties for sizes and numbers of inversions included in the alignment objective functions. Existing algorithmic techniques can be further incorporate to model non-intersecting inversions into the TF-map alignment.

Organizational constraints of elements in sets of promoters can also measured by, for example two exemplary approaches. One exemplary approach is the progressive alignment approach which is based on the current paradigm for global multiple sequence alignment. Progressive alignment begins with pair-wise alignment and then merges pairs of alignments (or aligns) following a guide tree until only a single alignment remains. In one embodiment, an algorithm for progressive alignment of TF-maps is designed, including inversions. Another exemplary approach is based on combinatorial interactions, a concept referred to as multidimensional matching, which identifies optimal associations of objects from multiple categories. The categories are usually natural promoters and the objects are the elements in TF-maps. Matching can be done hierarchically, and higher levels of the hierarchy can aggregate elements of lower levels; the structure of associations across promoters can then account for proximity of elements within TF-maps.

In some cases, algorithmic design strategy is used to design a synthetic regulatory sequence. In a related embodiment, once the synthetic regulatory region is designed, a therapeutic protein of interest can be expressed under the control of the synthetic regulatory region to achieve specificity of expression in a desired cell type. The desired cell type can be neural or a non-neural cell. The therapeutic transgene can be ChR1, ChR2, ChIEF, NpHR, eNpHR, VChR1, or melanopsin.

In one embodiment a combination of a rational template design, design using known regulation by TFs and an algorithmic design strategy is used to design a synthetic regulatory sequence. In a related embodiment, once the synthetic regulatory region is designed, a therapeutic protein of interest is expressed under the control of the synthetic regulatory region to achieve specificity of expression in a desired cell type. The desired cell type can be neural or a non-neural cell. The therapeutic transgene can be ChR1, ChR2, ChIEF, NpHR, eNpHR, VChR1, or melanopsin.

Targeted Delivery of a Transgene for Therapeutics

The ability to target transgene expression to specific cell types is important for gene therapeutics. For example, the retina is a highly complex system that filters, amplifies, and modulates the visual signal before it is sent to higher visual centers. The vast majority of these processes happen within the inner plexiform layer (IPL) where a system of bipolar and amacrine cells refines the visual signal into its primary components (e.g., motion, contrast, resolution). The majority of retinal cells are either ON-center (increased firing rate as a result of a step increase in contrast within the center of the receptive field) or OFF center type (increased firing rate as a result of a step decrease in contrast in the center of the receptive field), working in a push-pull inhibitory fashion. In one embodiment, to maintain this relationship between the two pathways, the two pathways can be controlled independently. ON and OFF channels of information, traveling from bipolar to ganglion cells, are at least partially modulated through a network of inhibitory amacrine cells within the inner nuclear layer.

In one embodiment, methods and compositions are provided herein to specifically establish light-sensitivity in the retina in the absence of photoreceptors to maintain the natural processing of these intricate circuits (i.e., gain of function), by genetically targeting transgene expression to specific subtypes of retinal cells. In one embodiment synthetic promoters are used to target expression of a therapeutic gene of interest, using a viral vector of a specific serotype, for example a specific AAV serotype. This can lead to reversal or improvement of the impairment. In a specific embodiment, the therapeutic gene of interest is a light sensitive protein, as further discussed herein.

hGRM6 Regulatory Elements

This disclosure also provides compositions comprising hGRM6 regulatory elements, and methods of using and generating such compositions. In some embodiments the hGRM6 regulatory element is the polynucleotide with the sequence of SEQ ID NO:1.

(SEQ. ID NO: 1)
5'-CCGGGTACCATCCTTAGATTATGAAACATTTACAATTATGAATGAA

TATTAGATGTTATCAAATGCTTTTTCTGCATCCATTTAGATAATCATGT

TTTTCCTTTAATCTGTTAATGCGGTGAATTACATTAATAGATTTCCTAA

GTCATTAATCTGCTAAAGTGCATTTCTGGGACAAACAGACTTGGTTATG

ACATTGTATGTATAAGCTTACCGGTGCC-3'

In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:1, or is identical to SEQ ID NO:1. The hGRM6 regulatory element may comprise a sequence that is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:1, or is identical to SEQ ID NO:1. The hGRM6 regulatory element may comprise (or consist of a sequence identical to) a truncated version of SEQ ID NO: 1. In some cases, such truncated version of SEQ ID NO:1 does not comprise the first 1, 2, 3, 4, 5, 6, 7, 8, 9, or 10 nucleotides of the sequence of SEQ ID NO:1. In some cases, such truncated version of SEQ ID NO:1 does not comprise the last 1, 2, 3, 4, 5, 6, 7, 8, 9, or 10 nucleotides of the sequence of SEQ ID NO:1.

I In some cases, the hGRM6 regulatory element is a polynucleotide that has a sequence that is one or more of the sequences represented in SEQ ID NOs: 2-11. The hGRM6 regulatory element may have (or may comprise) a sequence selected from the following: SEQ ID NOs:2-11. In some cases, the hGRM6 comprises at least 1, 2, 3, 4, 5, 6, 7, 8, or 9 of the sequences in SEQ ID NOs: 2-11. In some cases, the hGRM6 regulatory element comprises a sequence that is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:2, or is identical to SEQ ID NO:2.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:3, or is identical to SEQ ID NO:3.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:4 or is identical to SEQ ID NO:4.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:5 or is identical to SEQ ID NO:5.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:6 or is identical to SEQ ID NO:6.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:7 or is identical to SEQ ID NO:7.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:8 or is identical to SEQ ID NO:8.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:9, or is identical to SEQ ID NO:9.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:10, or is identical to SEQ ID NO:10.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:11 or is identical to SEQ ID NO:11.
In some cases, the hGRM6 regulatory element is at least 50%, 60%, 70%, 75%, 80%, 85%, 87%, 88%, 89%, 90%, 91%, 92%, 93%, 94%, 95%, 96%, 97%, 98%, or 99% identical to SEQ ID NO:12 or is identical to SEQ ID NO:12.

Figure 4A:
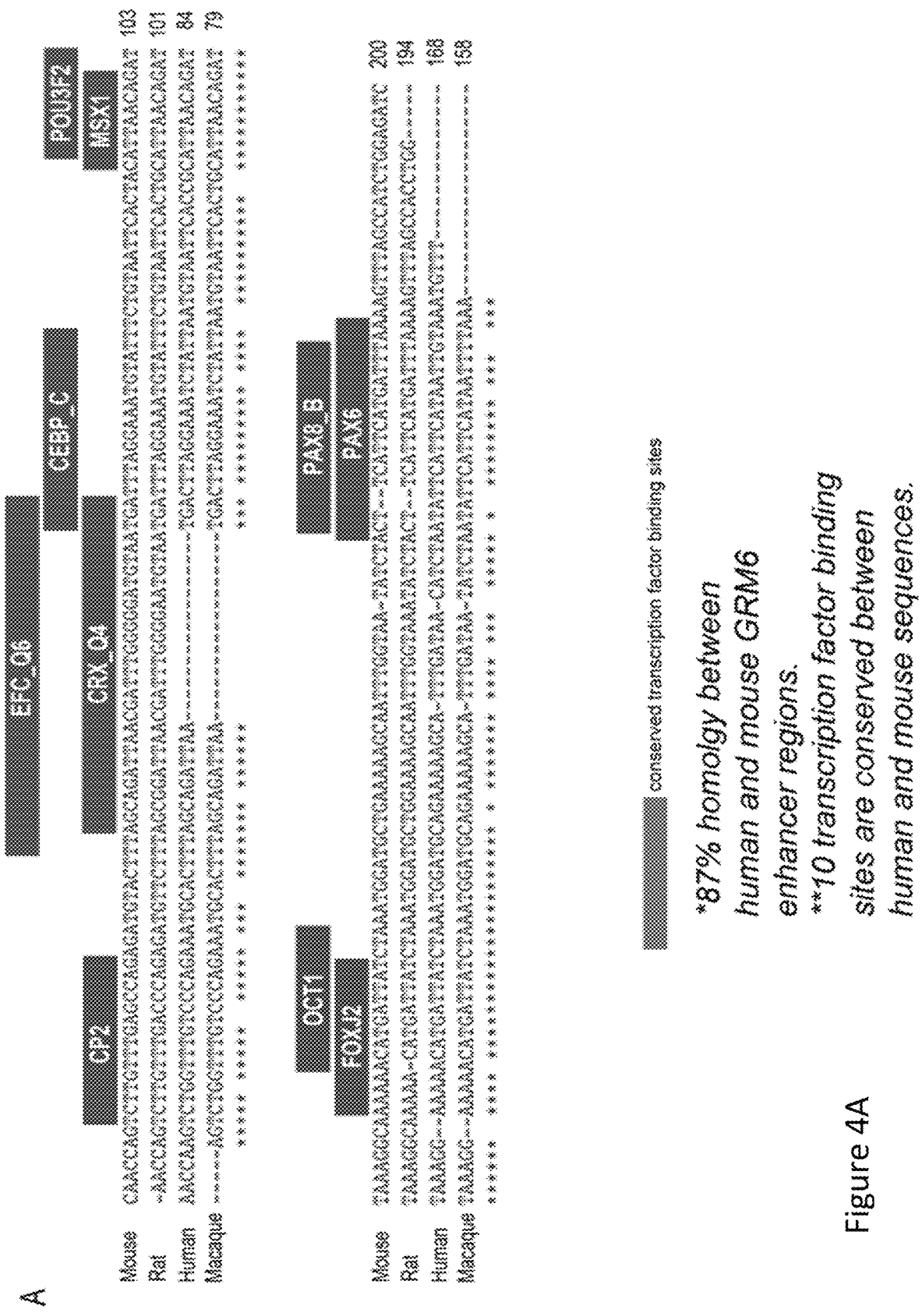
FIG. 4A and FIG. 4B show the conserved sequences of the GRM6 enhance across species. (A) shows that a 200 bp GRM6 enhancer is highly conserved (87%) between mouse and human sequences with 10 identified transcription factor binding sites.
Figure 4B:
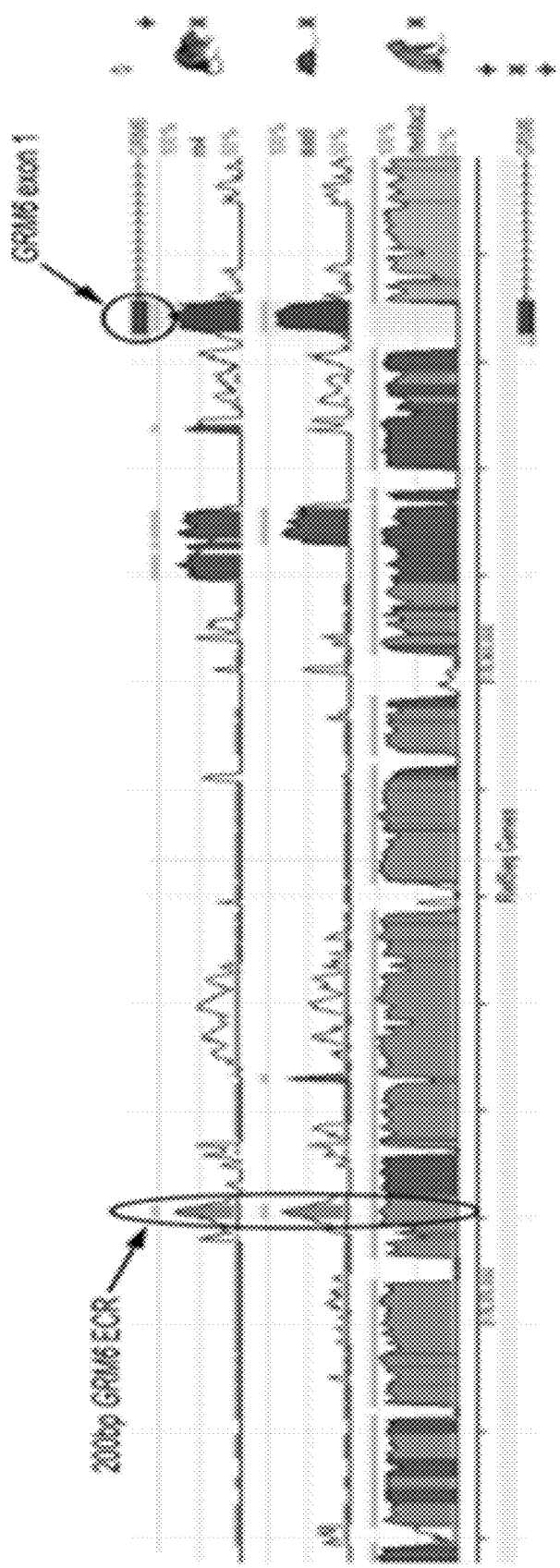
Figure 5:
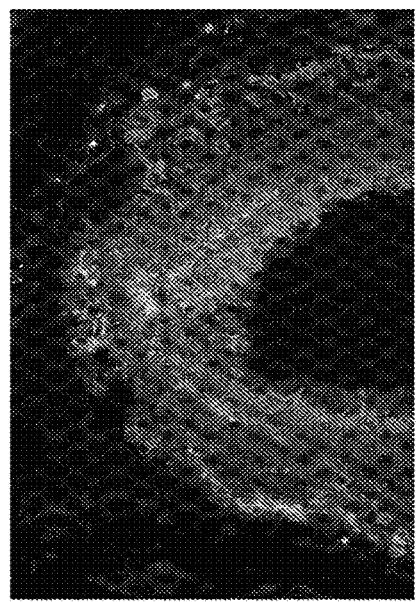
FIGS. 5-9 are confocal images that show the expression of eGFP & PKCa in the retina of rd10 mice 6 weeks after subretinal injection of an AAV vector comprising eGFP under the control of the hGRM6 regulatory element (SEQ ID NO:1).
Figure 5:
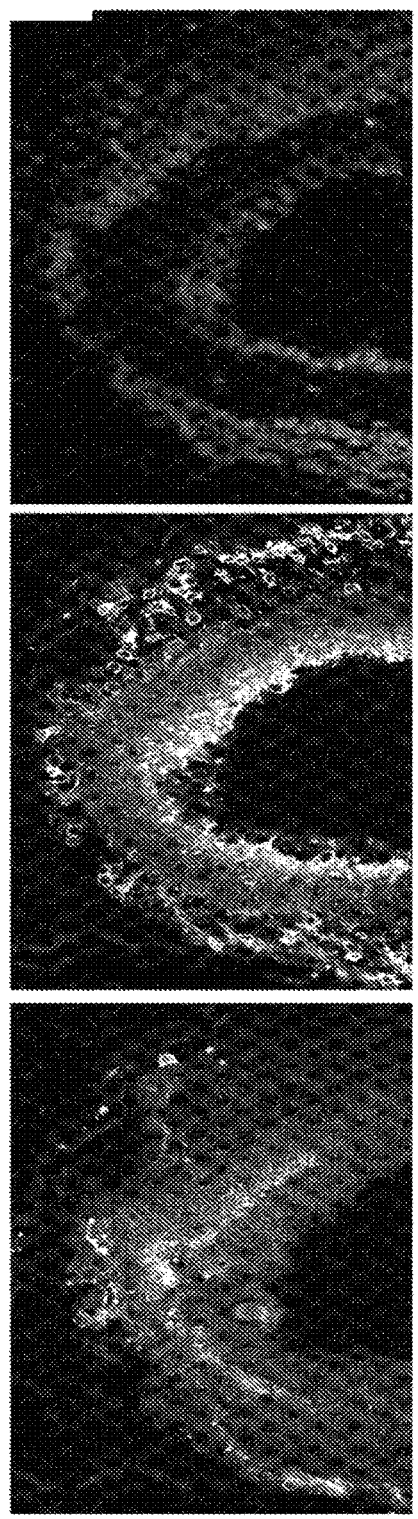
Figure 6:
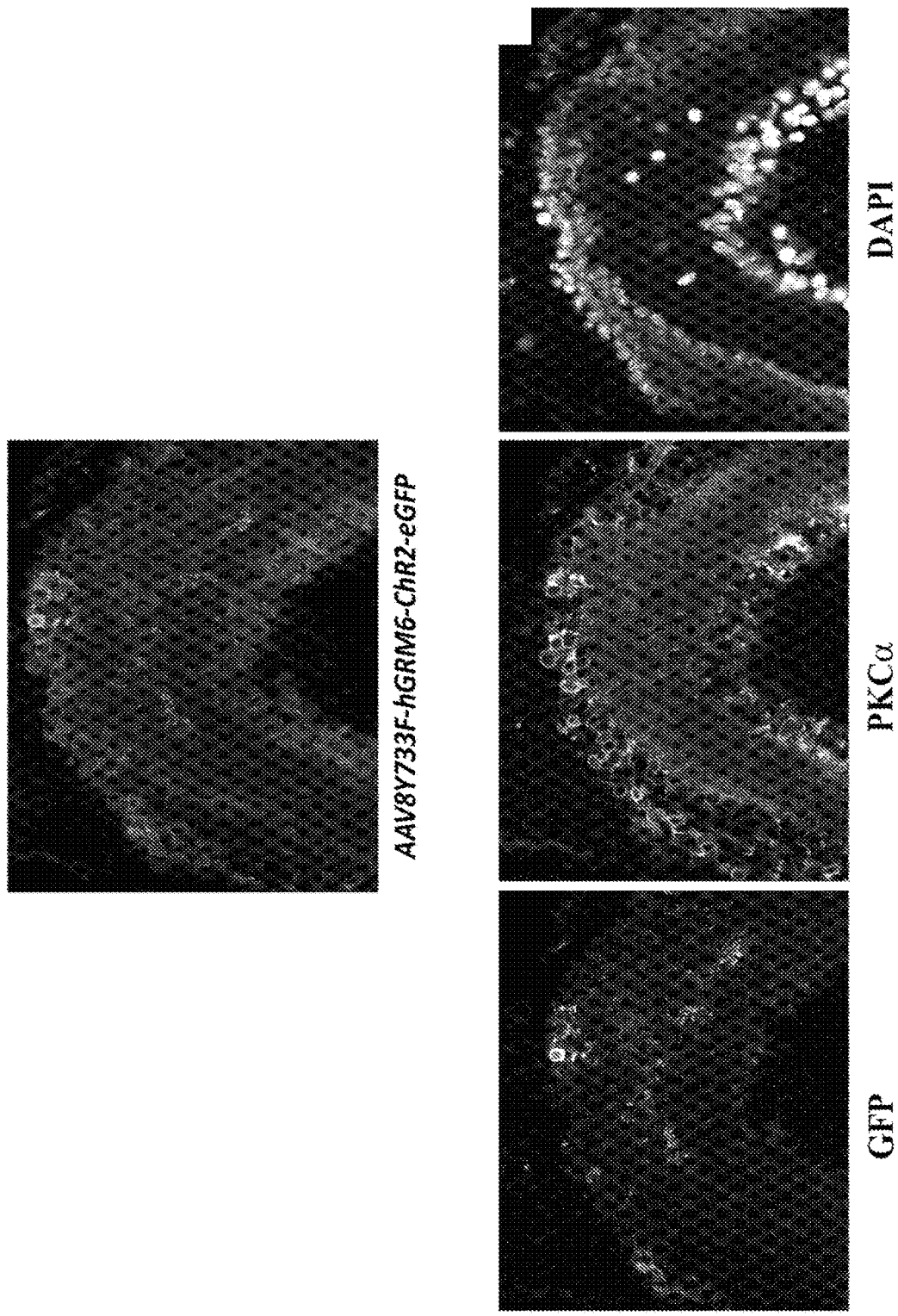
Figure 7:
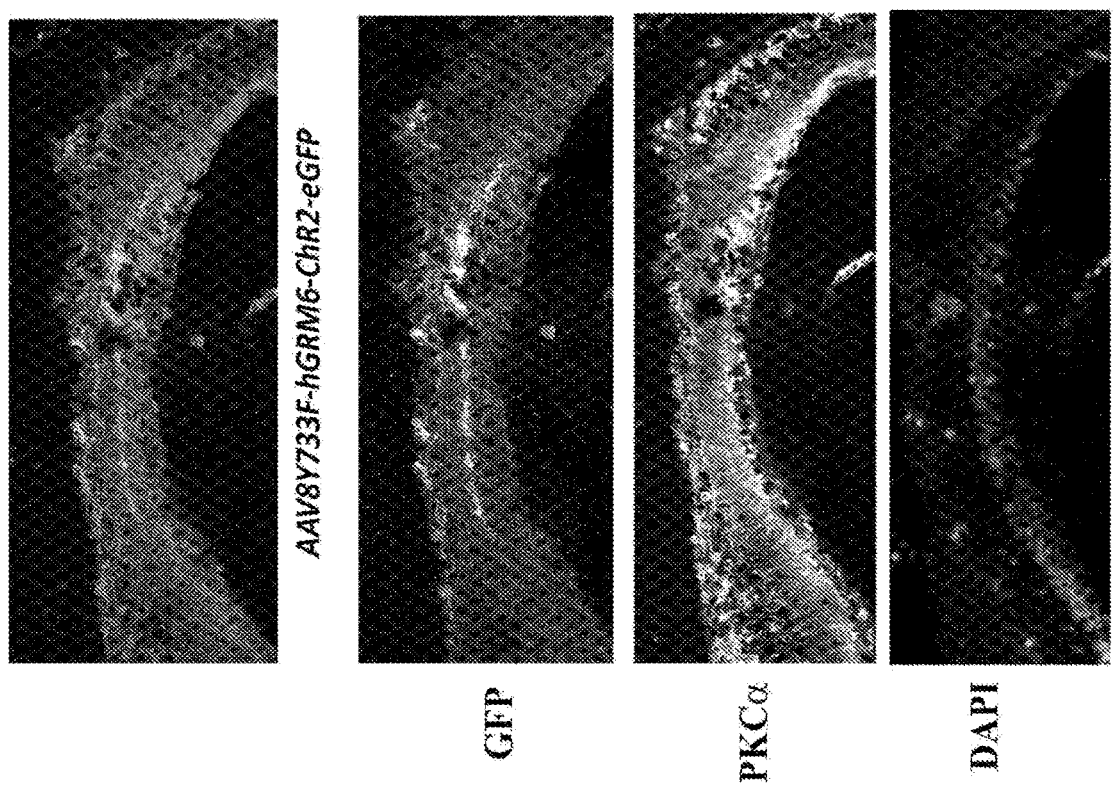
Figure 8:
Figure 8:
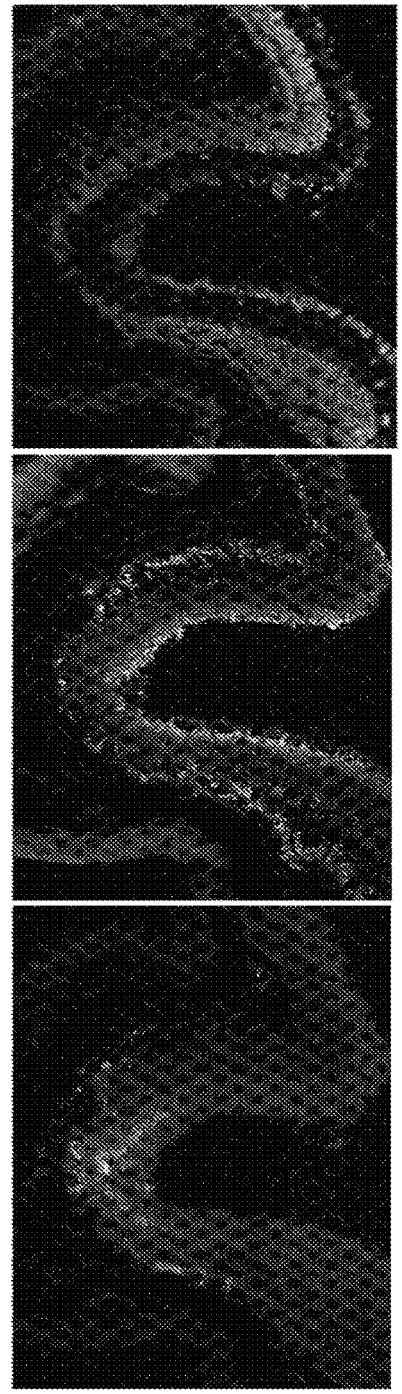
Figure 9:
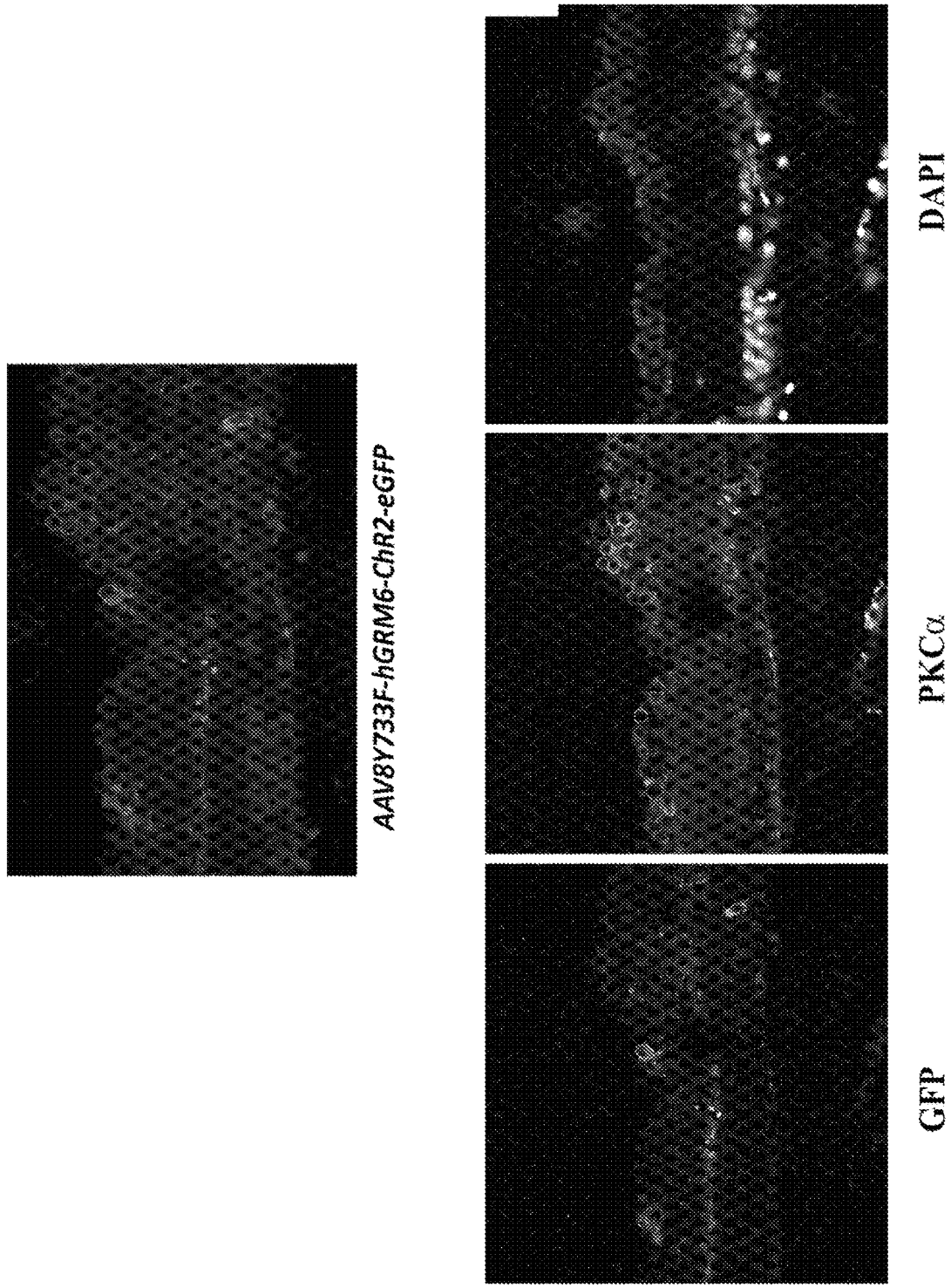

The hGRM6 regulatory element may comprise a sequence that is at least 50%, 60%, 70%, 75%, 80%, 85%, 87%, 88%, 89%, 90%, 91%, 92%, 93%, 94%, 95%, 96%, 97%, 98%, or 99% identical to a regulatory sequence for mGluR 6 in another organism. (See, e.g., FIG. 4).

The hGRM6 regulatory element may be capable of binding a specific transcription factor. Examples of transcription factors that may bind to the hGRM6 regulatory element include but are not limited to: CP2, EFC_Q6, CRX_Q4, CEBP_C, MSX1, POU3F2, FOXJ2, OCT1, PAX6, or PAX8_B. The hGRM6 regulatory element may bind combinations of transcription factors. For example, the hGRM6 regulatory element may bind at least 2, 3, 4, 5, 6, 7, 8, 9, 10 or more transcription factors. For another example, hGRM6 regulatory element may bind PAX8_B and FOXJ2; PAX8_B and OCT1; PAX6, FOXJ2 and MSX1; PAX6, FOXJ2, POU3F2 and EPC_Q6; PAX6, FOXJ2 and EPC_Q6; EFC_Q6 and CEBP_C; PAX6 and CP2 or any other suitable combination. In some cases, the hGRM6 regulatory element may be capable of binding multiple transcription factors at overlapping portions of the hGRM6 regulatory element. In some cases, a hGRM6 regulatory element may be capable of binding multiple transcription factors at non-overlapping/disparate portions of the hGRM6 regulatory element.

```
5'-TCTGGTTTGTCCCAG-3'        (SEQ. ID NO: 2)

5'-TTAGCAGATTAATGA-3'        (SEQ. ID NO: 3)

5'-AGCAGATTAATGA-3'          (SEQ. ID NO: 4)

5'-TGACTTAGGAAATCTATT-3'     (SEQ. ID NO: 5)

5'-CATTAACAG-3'              (SEQ. ID NO: 6)

5'-ATTAACAGAT-3'             (SEQ. ID NO: 7)

5'-AAAAACATGATTAT-3'         (SEQ. ID NO: 8)

5'-ACATGATTATCTA-3'          (SEQ. ID NO: 9)

5'-AATATTCATTCATAATTGTA-3'   (SEQ. ID NO: 10)

5'-ATATTCATTCATAATTG-3'      (SEQ. ID NO: 11)
```

In some embodiments, the hGRM6 regulatory element activates gene expression in a specific cell type. For example, the hGRM6 regulatory element may activate gene expression in retinal bipolar cells. In some cases, the hGRM6 regulatory element activates gene expression in retinal cone bipolar cells. In some cases, the hGRM6 regulatory element activates gene expression in retinal ON cone bipolar cells. In some embodiments, the hGRM6 regulatory element activates gene expression in retinal ON cone bipolar cells but not retinal OFF cone bipolar cells. In some embodiments, the hGRM6 regulatory element activates gene expression in retinal ON cone bipolar cells but not retinal rod bipolar cells.

In some embodiments, the hGRM6 regulatory element (acting alone or in association with other regulatory elements) activates gene expression in a certain cell type at a level that is at least 2-fold, 3-fold, 4-fold, 5-fold, 10-fold, 20-fold, 30-fold, 40-fold, 50-fold, 100-fold, 200-fold, 500-fold, 1000-fold, 5000-fold, or 10000-fold greater than it activates gene expression in a different cell type. For example, the hGRM6 regulatory element activates gene expression in retinal ON cone bipolar cells at a level that is at least 2-fold, 3-fold, 4-fold, 5-fold, 10-fold, 20-fold, 30-fold, 40-fold, 50-fold, 100-fold, 200-fold, 500-fold, 1000-fold, 5000-fold, or 10000-fold greater than it activates gene expression in a different cell type (e.g., retinal OFF cone bipolar cells, retinal rod bipolar cells, photoreceptor cells, etc.).

Light Sensitive Proteins

In specific embodiments, the therapeutic gene of choice encodes an opsin or a light sensitive protein. This disclosure provides vectors comprising a nucleic acid encoding a light-sensitive protein and further carrying a synthetic regulatory region as described herein. In some embodiments, the light-sensitive protein is selected from the group consisting of ChR1, ChR2, ChIEF, NpHR, eNpHR, VChR1, and melanopsin. In some cases, the light-sensitive protein can be selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, Cheta, ChR65, C1V1, and variants thereof. In a related embodiment the light-sensitive protein is ChR2 or a light-sensitive protein that is at least about 70%, at least about 80%, at least about 90% or at least about 95% identical to ChR2. In some embodiments, the light-sensitive protein is at least 70%, 80%, 90%, or 95% identical to a light sensitive protein described herein (e.g., ChR1, ChR2, ChIEF, NpHR, melanonopsin, etc.)

A light-sensitive protein often refers to a protein that is responsive to light. Membrane light-sensitive proteins can be activated with light, which leads to either a cation or anion exchange across the membrane that leads to either a hyperpolarization or depolarization of the membrane. In other words, depending on which protein is introduced and expressed, neural tissue can be either excited or depressed with light stimulation. Light-sensitive proteins include but are not limited to any membrane bound light-sensitive ion channel or proton pump that leads to a hyperpolarization or depolarization of the cell as a function of light stimulation.

Light-sensitive proteins include, but are not limited to, opsins such as rhodopsin, blue opsin, red opsin, halorhodopsin (NpHR), channelrhodopsin-2 (Chr2), enhanced halorhodopsin (eNpHR), archaerhodopsin-3 (Arch), leptosphaeria maculans (Mac) and functional fragments or variants thereof. Light-sensitive opsins of the present invention also include light-sensitive ion channels and ion pumps. In some cases, a combination of two or more light-sensitive proteins are used in the same method.

Light-sensitive proteins may also include proteins that are at least about 60%, at least about 70%, at least about 80%, at least about 90%, at least about 95%, or at least about 99% identical to the light-sensitive proteins such as rhodopsin, blue opsin, red opsin, melanopsin, halorhodopsin (NpHR), enhanced halorhopopsin (eNpHR), archaerhodopsin-3 (Arch), leptosphaeria maculans (Mac), ChR1, ChR2, VChR1, ChR2 C128A, ChR2 C128S, ChR2 C128T, ChR1-ChR2 hybrids/chimeras, Cheta, ChR65, C1V1, ChD, ChEF, ChF, or ChIEF. Preferably, these variants retain the function of the parent protein, such the sensitivity to light and the ability to modulate neuronal activities as described herein.

In some embodiments, the opsins is the one disclosed in Chow, B. Y., et al. High-performance genetically targetable optical neural silencing by light-driven proton pumps. *Nature* 463, 98-102

Light-sensitive proteins of the present disclosure can be derived from any organism source including, but not limited to bacteria, viruses, fungi, mycobacteria, protozoa, molds, yeasts, plants, humans, non-humans, multi-cellular parasites, vertebrates, animals, and archeabacteria.

In some embodiments, a light-sensitive protein comprises a light sensitive extracellular domain and an intracellular domain capable of modulating an intracellular signaling pathway. The coupling of these extracellular and intracellular domains allows a light-sensitive GPCR to use light energy to activate G-proteins at the intracellular side of a cell. The intracellular regions of a GPCR determine the G protein specificity and its precisely targeted role in cellular signaling. In embodiments of the present disclosure, a selected intracellular G-protein can be recombinantly fused to the intracellular loops of a selected light-sensitive GPCR (e.g., rhodopsin) that can be activated by different wavelengths of light. In some embodiments, a selected signaling protein is fused to a selected light-sensitive protein to confer light sensitivity on one or more signaling pathways involving the signaling protein A light-sensitive protein may be stimulated by an energy source, such as irradiation, resonance energy transfer, exciton migration, electron injection, or chemical reaction, to an activated energy state that is capable of effecting the predetermined cellular change desired In some embodiments, the light-sensitive protein can be activated by one or more ranges of wavelengths of light. Typically, a light-sensitive protein responds maximally to a specific wavelength of light, with tapering levels of response on either side of the electromagnetic spectrum from the specific wavelength. In some embodiments, a light-sensitive protein is sensitive to a light that is a visible light or invisible light Visible light includes light with a wavelength from about 390 to 750 nm that a typical human eye will respond to, such as 380-450 nm (violet), 450-475 nm (blue), 476-495 nm (cyan), 495-570 nm (green), 570-590 nm (yellow), 590-620 nm (orange), 620-750 nm (red).

In some embodiments, the light-sensitive protein can be absorbed and/or be activated by light that is delivered transdermally. This is accomplished by the use of a transdermal device that transmits high or low frequency light to activate the subdermally-expressed light-sensitive protein In some embodiments, the light is delivered through a light source that is placed (e.g. by implantation) under the skin.

In some embodiments, the light-sensitive protein can be absorb and/or be activated by light with a wavelength of about 650 to about 800 nm, about 400 to about 800 nm, or a partial range (e.g., at a portion in the range) within the wavelength range of about 200 nm to about 800 nm. In some embodiments, the light-sensitive protein may have a measurable absorbance over a range having a width of at least about 50 nm, preferably 100 nm, and more preferably 150 nm within the above-described wavelength range. If these wavelength ranges having the measurable absorbance exceed about 150 nm (e.g., about 400 nm, about 600 nm, etc.), these wavelength ranges may be about 200 nm, about 250 nm, about 300 nm, about 350 nm, about 400 nm, about 450 nm, about 500 nm, about 550 nm, about 600 nm, or the like. In other embodiments, the light-sensitive protein has a measurable absorbance over a certain range at two or more (e.g., 3,4, or the like) different positions within the wavelength range. The certain range can have a width of about 50 nm, about 100 nm, about 200 nm, about 250 nm, about 300 nm, about 350 nm, about 400 nm, or about 500 nm.

When a protein is sensitive to visible light, the light sensitivity of a protein can be described in terms of the color of the light, including red, orange, yellow, green, blue, indigo, and violet light. Thus, an opsin responding to blue light may be referred to as blue opsin, and an opsin responding to red light may be referred to as red opsin.

In some embodiments, variants of light-sensitive protein are genetically engineered to have desired properties, such as can be modulated by a light of particular wavelength of interest In some embodiments, the protein variants described herein rely on mutational strategies such as screening and/or selection to achieve the goals (such as optimization of desired light sensitivity discussed above). Screening involves inspection of a population for a given characteristic (usually a phenotype of interest) but placed no limits on the viability of the organisms that possessed (or more importantly did not possess) the desired characteristic. When selection is used, a predetermined mechanism allows only a certain population to survive.

In some embodiments, the genetic optimization process is performed by creating random mutations and observing the impact of these mutations on the desired properties. This process requires the screening of mutations and determining which mutants are to be used as templates for further exploration. A single random-mutation cycle yields several mutant proteins with improved properties. In other embodiments, several or more cycles are performed to achieve a significant improvement. Random mutations in most cases are more likely to be destructive or neutral than constructive.

For the random mutant studies wherein screening is involved, the process is described by L. You et al. Protein Eng. 9, 719 (1996); L. Wan et al., Proc. Natl. Acad. Sci. U.S.A. 95, 12825-12831 (1998); M. Callahan et al., Methods Mol. Biol. 57, 375-385 (1996). The net result is a population of mutant proteins with no a priori bias of location in the sequence. Alternatively, a combination of methods is used to generate controlled numbers of randomly distributed mutations.

In some embodiments, semi-random mutagenesis is performed wherein site directed and random mutagenesis are combined to achieve high mutagenesis efficiencies over a limited region. See J. U. Bowie et al. Science. 247, 1306-1310, (1990); J. Wen, et al., Nat. Struct. Biol. 3, 141-148, (1996); M. P. Krebs et al., J. Mol. Biol. 267, 172-183, (1997); M. P. Krebs et al., Proc. Natl. Acad. Sci. U.S.A. 90, 1987-1991, (1993); and S. R. Whaley et al., Nature. 405, 665-668, (2000).

In some embodiments, directed evolution and combinatorial methods are used. In these embodiments, one begins with wild-type protein that has become efficient for its intended purpose through evolution. A key challenge in using directed evolution for materials optimization is establishing a selection method that focuses on the desired properties of the material generated by the host. The use of directed evolution may not guarantee the creation of the ultimate material because the number of possible mutations and the time it takes to explore all the possibilities is years if not decades long. But directed evolution does provide a method of exploring a large number of possible mutations in a systematic way which yields the highest probability of improving the properties of a biological material.

The extent to which the variation in a population increases is dictated by the choice of the mutagenesis method. Site-directed mutagenesis can be used to explore small changes by changing one residue, and in the absence of structural information about the protein, can be used to fine-tune a particular mutant. However, there are instances wherein the modification of one amino acid provides greatly superior advantages to the un-mutated construct.

In some embodiments, other techniques can be used that may be designed to explore a greater area of the mutational landscape for a given protein. For example, the semi-random mutagenesis technique samples a mutational space that is greater compared to site-directed mutagenesis. The sampling of this space means that a new optimum might be reached instead of continuing to improve an original optimization (as in site directed mutagenesis). In this regard, random mutagenesis presents simultaneous advantages and disadvantages: it can be used to find new regions in the protein for optimization, but at the cost of neglecting the original optimization unless randomized libraries incorporating the desired mutation are used. The strategies for optimizing photochemical properties generally should take into account the localized nature of the mutational landscape. However, once key regions for mutagenesis are discovered, semi-random mutagenesis or site directed mutagenesis provides the most productive approach.

Gene Therapeutics

Gene therapy, as a form of molecular medicine, has the potential to significantly impact human health. It promises to provide treatments for a large number of acquired and inherited diseases and disorders. Gene therapy comprises introducing a therapeutic DNA into target cells resulting in a gain of function, silencing of function, or a replacement of a dysfunctional gene, such that the disease is either cured or the progression is significantly slowed.

In addition to the therapeutic transgene, any gene therapy requires the ability to deliver and regulate the expression of the transgene. For example viral vectors can be used for this purpose, for example such vectors can include but are not limited to recombinant adeno-associated viral (AAV) vectors, recombinant retroviral vectors, recombinant lentiviral vectors, recombinant poxviral vectors, herpes viral vectors, hybrid viral vectors, or the like. The choice of vector is partly determined by the desired site of delivery, requirements for expression, and other consideration.

Adeno-associated viruses (AAV) can be used to deliver the constructs described herein (e.g., DNA or RNA encoding light-sensitive protein, operably linked to a regulatory element described herein). Additionally, new mutant forms of AAV may be engineered that result in improved cell tropism and transduction.

Although AAV vectors and other types of viruses are useful for gene therapy, the regulation (or cell specificity) of gene expression is not well controlled through viruses alone. Provided herein are methods and compositions to design and use synthetic regulatory regions to develop strategies to achieve controlled gene expression in cell types of interest which can be used in combination any vector provided herein.

Adeno-Associated Viral Vectors

Adeno-associated viruses are small, single-stranded DNA viruses which require helper virus to facilitate efficient replication. The 4.7 kb genome of AAV is characterized by two inverted terminal repeats (ITR) and two open reading frames which encode the Rep proteins and Cap proteins, respectively. The Rep reading frame encodes four proteins of molecular weight 78 kD, 68 kD, 52 kD and 40 kD. These proteins function mainly in regulating AAV replication and rescue and integration of the AAV into a host cell's chromosomes. The Cap reading frame encodes three structural proteins of molecular weight 85 kD (VP 1), 72 kD (VP2) and 61 kD (VP3) (Berns, cited above) which form the virion capsid. More than 80% of total proteins in AAV virion comprise VP3.

Flanking the rep and cap open reading frames at the 5' and 3' ends are 145 bp inverted terminal repeats (ITRs), the first 125 bp of which are capable of forming Y- or T-shaped duplex structures. The two ITRs are the only cis elements essential for AAV replication, rescue, packaging and integration of the AAV genome. There are two conformations of AAV ITRs called "flip" and "flop". These differences in conformation originated from the replication model of adeno-associated virus which uses the ITR to initiate and reinitiate the replication. The entire rep and cap domains can be excised and replaced with a therapeutic or reporter transgene.

In some embodiments self-complementary AAV vectors are used. Self-complementary vectors have been developed to circumvent rate-limiting second-strand synthesis in single-stranded AAV vector genomes and to facilitate robust transgene expression at a minimal dose In another embodiment, the vector comprises a recombinant adeno-associated virus (AAV). In a related embodiment the vector comprises a recombinant virus selected from the group consisting of recombinant adeno-associated virus (AAV), recombinant retrovirus, recombinant lentivirus, recombinant baculovirus, and recombinant poxvirus. In a specific embodiment the AAV is of a serotype selected from the group consisting of AAV1, AAV2, AAV3, AAV4, AAV5, AAV6, AAV7, AAV8, AAV9, AAV10, AAV11, AAV12, and hybrids thereof. In a related embodiment the AAV comprises mutated capsid protein. In one specific embodiment the capsid protein comprises a mutated tyrosine residue. The mutated tyrosine residue can be selected from the group consisting of Y252F, Y272F, Y444F, Y500F, Y700F, Y704F, Y730F, Y275F, Y281F, Y508F, Y576F, Y612G, Y673F and Y720F. In a specific embodiment, the mutated capsid protein comprises a tyrosine residue mutated to a phenylalanine.

A light sensitive protein may be encoded by a virus (e.g., a recombinant adeno-associated virus (AAV)). In certain embodiments, the recombinant adeno-associated virus is of a serotype selected from the group consisting of AAV1, AAV2, AAV3, AAV4, AAV5, AAV6, AAV7, AAV8, AAV9, AAV10, AAV11, AAV12, and hybrids thereof. In a related embodiment, the nucleic acid is encapsidated within a recombinant virus selected from the group consisting of recombinant adeno-associated virus (AAV), recombinant retrovirus, recombinant lentivirus, and recombinant poxvirus.

In some cases, a self-complementary AAV vector is used. Exemplary vectors include sc-rAAV1 or sc-rAAV8.

Self-complementary AAV vectors bypass the requirement for viral second-strand DNA synthesis and lead to greater rate of expression of the transgene protein, Wu, Hum Gene Ther. 2007, 18(2):171-82

Adeno-Associated Viral Serotypes

Viral serotypes are strains of microorganisms having a set of recognizable antigens in common. There are several known serotypes of AAV, and the efficacy of transfection within the retina varies as a function of the specific serotype and the target cells. In certain embodiments the AAV vector are of any serotype including but not limited to AAV1, AAV2, AAV3, AAV4, AAV5, AAV6, AAV7, AAV8, AAV9, AAV10, AAV11, AAV12 or mutants or hybrids thereof. In some cases, the AAV vector can transduce retinal cells, retinal bipolar cells, or other cell type.

In some embodiments, several AAV vectors are generated to enable selection of the most optimal serotype, promoter, and transgene. In some embodiments, AAV vectors are packaged with both the naturally occurring serotype-8 capsid, as well as a novel tyrosine mutant AAV8 (Y733F), that have been demonstrated to give higher neuronal transduction levels.

The AAV ITR sequences and other AAV sequences employed in generating the minigenes, vectors, and capsids, and other constructs used in certain embodiments may be obtained from a variety of sources. For example, the sequences may be provided by presently identified human AAV types and AAV serotypes yet to be identified. Similarly, AAVs known to infect other animals may also provide these ITRs employed in the molecules or constructs of this invention. Similarly, the capsids from a variety of serotypes of AAV may be "mixed and matched" with the other vector components. See, e.g., International Patent Publication No. WO01/83692, published Nov. 8, 2001, and incorporated herein by reference. A variety of these viral serotypes and strains are available from the American Type Culture Collection, Manassas, Va., or are available from a variety of academic or commercial sources. Alternatively, it may be desirable to synthesize sequences used in preparing the vectors and viruses of the invention using known techniques, which may utilize AAV sequences which are published and/or available from a variety of databases. The selection of the species and serotype of AAV that provides these sequences is within the skill of the artisan.

Adeno-Associated Viruses and Point Mutations of Surface-Exposed Tyrosines

Recombinant adeno-associated virus vectors are in use in several clinical trials, but relatively large vector doses are needed to achieve therapeutic benefits. Large vector doses also trigger an immune response as a significant fraction of the vectors fails to traffic efficiently to the nucleus and is targeted for degradation by the host cell proteasome machinery. It has been reported that epidermal growth factor receptor protein tyrosine kinase (EGFR-PTK) signaling negatively affects transduction by AAV Serotype 2 vectors by impairing nuclear transport of the vectors. Tyrosine-phosphorylated AAV2 vectors enter but fail to transduce effectively, in part because of the ubiquitination of AAV capsids followed by proteasome-mediated degradation. It was recently shown that point mutations in tyrosines in AAV2 lead to high-efficiency transduction at lower virus titers. Additionally, tyrosine-mutated AAVs can work in the retina. In one embodiment of the present invention, mutations of the surface-exposed tyrosine residues allow the vectors to evade phosphorylation and subsequent ubiquitination and, thus, prevent proteasome-mediated degradation, leading to greater transduction and subsequent gene expression of light sensitive elements.

Recombinant Viruses/Vectors

In some cases, the light-sensitive proteins are expressed in the cells using gene therapy. The gene therapy uses a vector including a nucleotide encoding the light-sensitive protein. A vector (sometimes also referred to as gene delivery or gene transfer vehicle) refers to a macromolecule or complex of molecules comprising a polynucleotide to be delivered to the cell. The polynucleotide to be delivered may comprise a coding sequence of interest in gene therapy. Vectors include, for example, viral vectors such as adenoviruses, adeno-associated viruses (AAV) (described herein), and retroviruses, liposomes and other lipid-containing complexes, and other macromolecular complexes capable of mediating delivery of a polynucleotide to a target cell. Some embodiments of the present disclosure involve a vector comprising a recombinant nucleic acid.

In some embodiments, the present invention provides a recombinant virus comprising a recombinant nucleic acid of the invention. A recombinant virus can be an adeno-associated virus (AAV), recombinant retrovirus, recombinant lentivirus, or recombinant poxvirus.

In some embodiments, a self-complementary vector (sc) is used.

Vectors can comprise components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use in the present invention include viral vectors, lipid based vectors and other non-viral vectors that are capable of delivering a nucleotide according to the present invention to the target cells. The vector can be a targeted vector, especially a targeted vector that preferentially binds to neoplastic cells, such as cancer cells or tumor cells. Viral vectors for use in the invention can include those that exhibit low toxicity to a target cell and induce production of therapeutically useful quantities of the light-sensitive transmembrane protein in a cell specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the light-sensitive transmembrane protein and is replication-defective in humans.

Other viral vectors that can be use in accordance with the present invention include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the invention. For example, retroviral vectors may be based on murine leukemia virus (MLV). See, e.g., Hu and Pathak, Pharmacol. Rev. 52:493511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a light-sensitive transmembrane protein nucleic acid. In methods of delivery to neoplastic cells, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells. They are also highly efficient at transducing human epithelial cells.

Lentiviral vectors for use in the invention may be derived from human and non-human (including SIV) lentiviruses. Examples of lentiviral vectors include nucleic acid sequences required for vector propagation as well as a tissue-specific promoter operably linked to a light-sensitive trans-membrane protein gene. These former may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudo-typing". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), may also be used in the invention. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the invention, more than one promoter can be included in the vector to allow more than one heterologous gene to be expressed by the vector. Further, the vector can comprise a sequence which encodes a signal peptide or other moiety which facilitates expression of the light-sensitive transmembrane protein from the target cell.

To combine advantageous properties of two viral vector systems, hybrid viral vectors may be used to deliver a nucleic acid encoding a light-sensitive transmembrane protein to a target tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000.

Retroviral genomes contained within an adenovirus may integrate within the target cell genome and effect stable gene expression.

Other nucleotide sequence elements, which facilitate expression of the light-sensitive protein gene and cloning of the vector are further contemplated. For example, the presence of enhancers upstream of the promoter or terminators downstream of the coding region, for example, can facilitate expression.

Other embodiments of the disclosure provide for a host cell derived from a cell transfected with a recombinant virus. Still other embodiments involve a host cell comprising a recombinant nucleic acid.

In some embodiments, the DNA that is packaged is self-complementary. In some embodiments, the DNA that is packaged is single-stranded DNA.

Conditions Amenable to Treatment

In some embodiments, the present invention provides methods of treating a subject suffering from a disease or disorder. The compositions and methods described herein can be utilized to treat central and peripheral nervous system diseases and disorders.

In one aspect, the compositions and methods of this invention are utilized to treat photoreceptor diseases. Photoreceptor diseases such as retinitis pigmentosa (RP) and age-related macular degeneration (ARMD) cause blindness in 15 million people worldwide, a number that is increasing with the age of the population. There have been attempts to restore basic visual function through gene replacement therapy or cellular transplantation. However, current approaches are fundamentally limited in scope and extent of potential impact, as they attempt to correct mechanistically distinct genetic pathways on a one-at-a-time basis. Photoreceptor diseases are genetically diverse, with over 160 different mutations leading to degeneration. There have also been efforts in utilizing electrical stimulation with implanted acute, semi-acute, and long-term retinal prostheses in human subjects. They have shown elementary progress but are gene-nonspecific; electrical stimulation offers only gross specificity and indiscriminately drives visual information channels mediated by unique cell types. Activating retinal neurons requires large disc electrodes (at least 20 times the diameter of a retinal ganglion cell), leading to stimulation of broad areas of retina in a nonselective fashion, greatly limiting the achievable visual resolution. In this aspect, the compositions and methods of this invention consist of introducing a gene encoding a light-sensitive protein (e.g., ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, Cheta, ChR65, C1V1, melanopsin, and variants thereof) to induce light sensitivity in $2^{nd}$ order neurons (e.g., bipolar cells) delivered using a viral vector such as an AAV8 with a single tyrosine to phenylalanine mutation, under the control of a regulatory element (e.g., GRM6). The activation of these light-sensitive proteins could be controlled by ambient light or through a light-delivery device such as the goggles described in PCT Publication No. WO2010/011404, filed May 20, 2009, "Vector for Delivery of Light-Sensitive Proteins and Methods of Use."

The methods of the invention can be used to treat (e. g., prior to or after the onset of symptoms) in a susceptible subject or subject diagnosed with a variety of eye diseases. The eye disease may be a result of environmental (e. g., chemical insult, thermal insult, and the like), mechanical insult (e. g., injury due to accident or surgery), or genetic factors. The subject having the condition may have one or both eyes affected, and therapy may be administered according to the invention to the affected eye or to an eye at risk of photoreceptor degeneration due to the presence of such a condition in the subject's other, affected eye.

The present invention provides methods which generally comprise the step of intraocularly administering (e. g., by subretinal injection or by intravitreal injection) a gene delivery vector which directs the expression of a light-sensitive protein to the eye to treat, prevent, or inhibit the onset or progression of an eye diseaser.

Another condition amenable to treatment according to the invention is Age-related Macular Degeneration (AMD). The macula is a structure near the center of the retina that contains the fovea. This specialized portion of the retina is responsible for the high-resolution vision that permits activities such as reading. The loss of central vision in AMD is devastating. Degenerative changes to the macula (maculopathy) can occur at almost any time in life but are much more prevalent with advancing age. Conventional treatments are short-lived, due to recurrent choroidal neovascularization. AMD has two primary pathologic processes, choroidal neovascularization (CNV) and macular photoreceptor cell death.

Exemplary conditions of particular interest which are amenable to treatment according to the methods of the invention include, but are not necessarily limited to, retinitis pigmentosa (RP), diabetic retinopathy, and glaucoma, including open-angle glaucoma (e. g., primary open-angle glaucoma), angle-closure glaucoma, and secondary glaucomas (e. g., pigmentary glaucoma, pseudoexfoliative glaucoma, and glaucomas resulting from trauma and inflammatory diseases).

Further exemplary conditions amenable to treatment according to the invention include, but are not necessarily limited to, retinal detachment, age-related or other maculopathies, photic retinopathies, surgery-induced retinopathies, toxic retinopathies, retinopathy of prematurity, retinopathies due to trauma or penetrating lesions of the eye, inherited retinal degenerations, surgery-induced retinopathies, toxic retinopathies, retinopathies due to trauma or penetrating lesions of the eye.

Specific exemplary inherited conditions of interest for treatment according to the invention include, but are not necessarily limited to, Bardet-Biedl syndrome (autosomal recessive); Congenital amaurosis (autosomal recessive); Cone or cone-rod dystrophy (autosomal dominant and X-linked forms); Congenital stationary night blindness (autosomal dominant, autosomal recessive and X-linked forms); Macular degeneration (autosomal dominant and autosomal recessive forms); Optic atrophy, autosomal dominant and X-linked forms); Retinitis pigmentosa (autosomal dominant, autosomal recessive and X-linked forms); Syndromic or systemic retinopathy (autosomal dominant, autosomal recessive and X-linked forms); and Usher syndrome (autosomal recessive).

In another aspect, the compositions and methods of this invention are utilized to treat peripheral injury, nociception, or chronic pain. Nociception (pain) for prolonged periods of time can give rise to chronic pain and may arise from injury or disease to visceral, somatic and neural structures in the body. Although the range of pharmacological treatments for neuropathic pain has improved over the past decade, many patients do not get effective analgesia, and even effective medications often produce undesirable side effects. Substance P (SP) is involved in nociception, transmitting information about tissue damage from peripheral receptors to the central nervous system to be converted to the sensation of pain. It has been theorized that it plays a part in fibromyalgia A role of substance P in nociception is suggested by the reduction in response thresholds to noxious stimuli by central administration of NK1 and NK2 agonists. Pain behaviors induced by mechanical, thermal and chemical stimulation of somatic and visceral tissues were reduced in the mutant mice lacking SP/NKA. In one embodiment light-sensitive proteins can silence the activity of over-active neurons (i.e., substance P expressing peripheral neurons) due to peripheral injury or chronic pain using NpHR or eNpHR. NpHR/eNpHR can be genetically targeted to substance P expressing cells using the substance P promoter sequence. In another embodiment light-sensitive proteins enhance the activity of neurons that are inactive due to peripheral injury or chronic pain.

The methods and compositions provided herein can be used to target neurons, (e.g., mGluR6-expressing neurons, motor neurons, sensory neurons, etc.) within the eye, or outside of the eye.

In another aspect, the compositions and methods of this invention are utilized to treat spinal cord injury and/or motor neuron diseases. Spinal cord injury can cause myelopathy or damage to white matter and myelinated fiber tracts that carry sensation and motor signals to and from the brain. It can also damage gray matter in the central part of the spine, causing segmental losses of interneurons and motor neurons. Spinal cord injury can occur from many causes, including but not limited to trauma, tumors, ischemia, abnormal development, neurodevelopmental, neurodegenerative disorders or vascular malformations. In one embodiment light-sensitive proteins activate damaged neural circuits to restore motor or sensory function. In one specific embodiment the elements act to allow control of autonomic and visceral functions. In other embodiments the elements act to allow control of somatic skeletal function. The neural control of storage and voiding of urine is complex and dysfunction can be difficult to treat. One treatment for people with refractory symptoms is continuous electrical nerve stimulation of the sacral nerve roots using implanted electrodes and an implanted pulse generator. However, stimulation of this nerve root can result in a number of different complications or side effects. Being able to directly control the sacral nerve through genetically-targeted tools would be highly beneficial. In one embodiment, both ChR2 and NpHR could be expressed in this nerve to control storage and voiding of the bladder.

In another aspect, the compositions and methods of this invention are utilized to treat Parkinson's disease. Parkinson's disease belongs to a group of conditions called movement disorders. They are characterized by muscle rigidity, tremor, a slowing of physical movement (bradykinesia) and, in extreme cases, a loss of physical movement (akinesia). The primary symptoms are the results of decreased stimulation of the motor cortex by the basal ganglia, normally caused by the insufficient formation and action of dopamine, which is produced in the dopaminergic neurons of the brain. Parkinson's disease is both chronic and progressive. Deep brain stimulation (DBS) is an effective surgical treatment for advanced Parkinson's disease (PD), with significant advantages in morbidity-mortality and quality of life when compared to lesion techniques such as thalamotomy and/or pallidotomy. The procedure is indicated in patients with severe resting tremor, unresponsive to conventional medical treatment or with motor complications. The most commonly reported complications in the intra- and post-surgical period are aborted procedure, misplaced leads, intracranial hemorrhage, seizures and hardware complications, whereas in the long-term period, symptoms may include high level cognitive dysfunction, psychiatric, and subtle language problems. Indeed, this method of therapy would be improved by being able to target specific cell types within a given region to avoid these side effects. In one embodiment light-sensitive proteins specifically activate dopaminergic circuits.

In another specific aspect, the compositions and methods of this invention are utilized to treat epilepsy and seizures. Epilepsy is a neurological disorder that is often characterized by seizures. These seizures are transient signs and/or symptoms due to abnormal, excessive or asynchronous neuronal activity in the brain. Over 30% of people with epilepsy do not have seizure control even with the best available medications. Epilepsy is not a single disorder, but rather as a group of syndromes with vastly divergent symptoms but all involving episodic abnormal electrical activity in the brain. Acute deep brain stimulation (DBS) in various thalamic nuclei and medial temporal lobe structures has recently been shown to be efficacious in small pilot studies. There is little evidence-based information on rational targets and stimulation parameters. Amygdalohippocampal DBS has yielded a significant decrease of seizure counts and interictal EEG abnormalities during long-term follow-up. Data from pilot studies suggest that chronic DBS for epilepsy may be a feasible, effective, and safe procedure. Again, being able to genetically-target activation to specific subsets of cells would improve the quality of the therapy as well as minimize overall side effects. In specific embodiments, the light-sensitive proteins are utilized to alter the asynchronous electrical activity leading to seizures in these deep brain areas.

In another aspect the compositions and methods of this invention are utilized to effect the light-stimulated release of implanted drug or vaccine stores for the prevention, treatment, and amelioration of diseases.

In another aspect the compositions and methods of this invention are utilized to treat neurodegenerative disease selected from but not limited to alcoholism, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), chronic pain, Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, and Tables dorsalis.

In another aspect the compositions and methods of this invention are utilized to treat a neurodevelopmental disease selected from but not limited to attention deficit hyperactivity disorder (ADHD), attention deficit disorder (ADD), schizophrenia, obsessive-compulsive disorder (OCD), mental retardation, autistic spectrum disorders (ASD), cerebral palsy, Fragile-X Syndrome, Downs Syndrome, Rett's Syndrome, Asperger's syndrome, Williams-Beuren Syndrome, childhood disintegrative disorder, articulation disorder, learning disabilities (i.e., reading or arithmetic), dyslexia, expressive language disorder and mixed receptive-expressive language disorder, verbal or performance aptitude. Diseases that can result from aberrant neurodevelopmental processes can also include, but are not limited to bi-polar disorders, anorexia, general depression, seizures, obsessive compulsive disorder (OCD), anxiety, bruxism, Angleman's syndrome, aggression, explosive outburst, self injury, post traumatic stress, conduct disorders, Tourette's disorder, stereotypic movement disorder, mood disorder, sleep apnea, restless legs syndrome, dysomnias, paranoid personality disorder, schizoid personality disorder, schizotypal personality disorder, antisocial personality disorder, borderline personality disorder, histrionic personality disorder, narcissistic personality disorder, avoidant personality disorder, dependent personality disorder, reactive attachment disorder; separation anxiety disorder; oppositional defiant disorder; dyspareunia, pyromania, kleptomania, trichotillomania, gambling, pica, neurotic disorders, alcohol-related disorders, amphetamine-related disorders, cocaine-related disorders, marijuana abuse, opioid-related disorders, phencyclidine abuse, tobacco use disorder, bulimia nervosa, delusional disorder, sexual disorders, phobias, somatization disorder, enuresis, encopresis, disorder of written expression, expressive language disorder, mental retardation, mathematics disorder, transient tic disorder, stuttering, selective mutism, Crohn's disease, ulcerative colitis, bacterial overgrowth syndrome, carbohydrate intolerance, celiac sprue, infection and infestation, intestinal lymphangiectasia, short bowel syndrome, tropical sprue, Whipple's disease, Alzheimer's disease, Parkinson's Disease, ALS, spinal muscular atrophies, and Huntington's Disease. Further examples, discussion, and information on neurodevelopmental disorders can be found, for example, through the Neurodevelopmental Disorders Branch of the National Institute of Mental Health (worldwide website address at nihm-.nih.gov/dptr/b2-nd.cfm). Additional information on neurodevelopmental disorders can also be found, for example, in Developmental Disabilities in Infancy and Childhood: Neurodevelopmental Diagnosis and Treatment, Capute and Accardo, eds. 1996, Paul H Brookes Pub Co.; Hagerman, Neurodevelopmental Disorders: Diagnosis and Treatment, 1999, Oxford Univ Press; Handbook of Neurodevelopmental and Genetic Disorders in Children, Goldstein and Reynolds, eds., 1999, Guilford Press; Handbook of Neurodevelopmental and Genetic Disorders in Adults, Reynolds and Goldstein, eds., 2005, Guilford Press; and Neurodevelopmental Disorders, Tager-Flusberg, ed., 1999, MIT Press.

Assessment of Therapy

The effects of a therapy provided herein can be assessed in a variety of ways, using methods known in the art. For example, the subject's vision can be tested according to conventional methods. Such conventional methods include, but are not necessarily limited to, electroretinogram (ERG), focal ERG, tests for visual fields, tests for visual acuity, ocular coherence tomography (OCT), Fundus photography, Visual Evoked Potentials (VEP) and Pupillometry. In other embodiments, the subject can be assessed behaviorally. In general, the invention provides for maintenance of a subject's vision (e. g., prevention or inhibition of vision loss of further vision loss due to photoreceptor degeneration), slows onset or progression of vision loss, or in some embodiments, provides for improved vision relative to the subject's vision prior to therapy.

Optical Control

Technological advances in neuroscience have enabled the ability to optically control neural activity precisely with visible light. Central to this technology is the expression of microbial opsin genes that encode photosensitive ion channels and pumps. Boyden, E. S. et al., Nat Neurosci 8, 1263-1268 (2005); Han, X. & Boyden, E. S. PLoS ONE 2, e299 (2007); Han, X., et al., Neuron 62, 191-198 (2009); Lagali, P. S., et al., Nat. Neurosci. (2008). When expressed in mammalian neurons, these optical neuromodulators enable the complete control of neural activity with extremely high spatial and temporal precision. Furthermore, these opsins can be genetically targeted and stably expressed in desired cell populations using non-pathogenic adeno-associated viral (AAV) vectors containing select genetic regulatory sequences. Lagali, P. S., et al., Nat Neurosci (2008); Flannery, J. G. & Greenberg, Neuron 50, 1-3 (2006); Greenberg, K. P., et al., Association of Research in Vision and Ophthalmology (2007); Horsager, A., et al. Association of Research in Vision and Ophthalmology (2009).

In some embodiments, this disclosure provides a method of optically controlling neural activity in a cell, comprising expressing in the cell a recombinant nucleic acid comprising the coding region for a light-sensitive protein, and controlling the neural activity of the cell with a light beam to modulate the expression of the light-sensitive protein.

High spatial and temporal precision can be controlled through the employment of precise activation of the LED array. This would include the stimulation pulse duration (i.e., duration the LED stimulus would be activated), inter-pulse duration (i.e., frequency or pulse train rate), space constant of activation (i.e., how far apart the LED stimuli should be to be effective), and amplitude of light stimulus.

In some embodiments, the extent of silencing is dynamically controlled via a variable intensity optical source. In some embodiments, the optical source comprises an implantable 1- or 2- or 3-dimensional fiber optic device. The stimulation patterns presented by the device can be controlled in both the time and space dimensions. For example, stimulation patterns from a specific location on the optical fiber of LED can be modulated in terms of pulse duration and frequency. In the space dimension, the activation of different LEDs can be controlled both in terms of location (i.e., which LEDs or optical fiber locations are active at each point in time) and amplitude (i.e., intensity).

In some embodiments, the controlling is carried out with high spatial and temporal precision using a specifically positioned device where the light emission is controlled over time. Some embodiments employ a 1 or 2-dimensional array of light stimulation, with the temporal pattern of activation controlled through modulation of the pulse train from each LED. See, e.g., US Application Publications Nos. US20080125832A1 and US20090312818A1 for more details.

Pharmaceutical Compositions

This disclosure provides compositions, often comprising a recombinant nucleic acid and a pharmaceutically acceptable carrier. In some cases, the pharmaceutical composition comprises a viral vector and a pharmaceutically acceptable carrier.

A pharmaceutical composition of the disclosure is formulated to be compatible with its intended route of administration. Examples of routes of administration include intravitreal, subretinal, parenteral, e.g., intravenous, intradermal, subcutaneous, oral (e.g., inhalation), transdermal (topical), transmucosal, rectal administration, and direct injection into the affected area, such as direct injection into a tumor, intravitreal injection, or subretinal injection. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for internal use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Methods of administering agents according to the present invention are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection. Such transfected cells may be inserted or otherwise targeted at the site where diseased cells are located. In this embodiment, the initiation energy source may be a biochemical source as such ATP, in which case the initiation energy source is considered to be directly implanted in the transfected cell. Alternatively, a conventional micro-emitter device capable of acting as an initiation energy source may be transplanted at the site of the diseased cells.

Nucleic acid vector transfection (e.g., transient transfection) methods may be used to introduce the SRE or other vectors described herein into cells, including human cells. Methods for preparation of transfection-grade nucleic acid expression vectors and transfection methods are well established. See, e.g., Sambrook and Russell (2001), "Molecular Cloning: A Laboratory Manual," 3rd ed, (CSHL Press); and Current Protocols in Molecular Biology, John Wiley & Sons, N.Y. (2005), 9.1-9.14. Examples of high efficiency transfection efficiency methods include "nucleofection," as described in, e.g., Trompeter (2003), J Immunol. Methods, 274(1-2):245-256, and in international patent application publications WO2002086134, WO200200871, and WO2002086129, transfection with lipid-based transfection reagents such as Fugene® 6 and Fugene® HD(Roche), DOTAP, and lipofectamine™ LTX in combination with the PLUS™ (Invitrogen, Carlsbad, CA), Dreamfect™ (OZ Biosciences, Marseille, France), GeneJuice™ (Novagen, Madison, WI), polyethylenimine (see, e.g., Lungwitz et al., (2005), Eur. J Pharm. Biopharm., 60(2):247-266), and GeneJammer™ (Stratagene, La Jolla, CA), and nanoparticle transfection reagents as described in, e.g., U.S. patent application Ser. No. 11/195,066.

Kits

Compositions and reagents useful for the present invention may be packaged in kits to facilitate application of the present invention. In some embodiments, the present method provides for a kit comprising a recombinant nucleic acid of the invention. In some embodiments, the present method provides for a kit comprising a recombinant virus of the invention. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of a light source.

EXAMPLES

Example 1

Targeted Transgene Expression in Retinal Bipolar Cells

Both wildtype viral serotypes and a set of proprietary AAV vectors available with tyrosine mutations to their capsid sequences can alter tropism. These vectors have been tested in the retina and have found them to be highly efficient at transducing most if not all retinal cells under the control of the ubiquitous CBA promoter. An intravitreal injection led to transduction of bipolar cells (FIG. 2A).

Furthermore, that transgene expression can be targeted to the ON bipolar cells under the control of the cell-specific GRM6 promoter sequence in the rd1 mouse has been established (FIG. 1B-D) when using these mutant serotypes with at least 50% efficiency. These findings provide evidence that cell-specific synthetic promoters can be used to target expression of transgenes to specific subsets of retinal bipolar cells.

Figure 2:
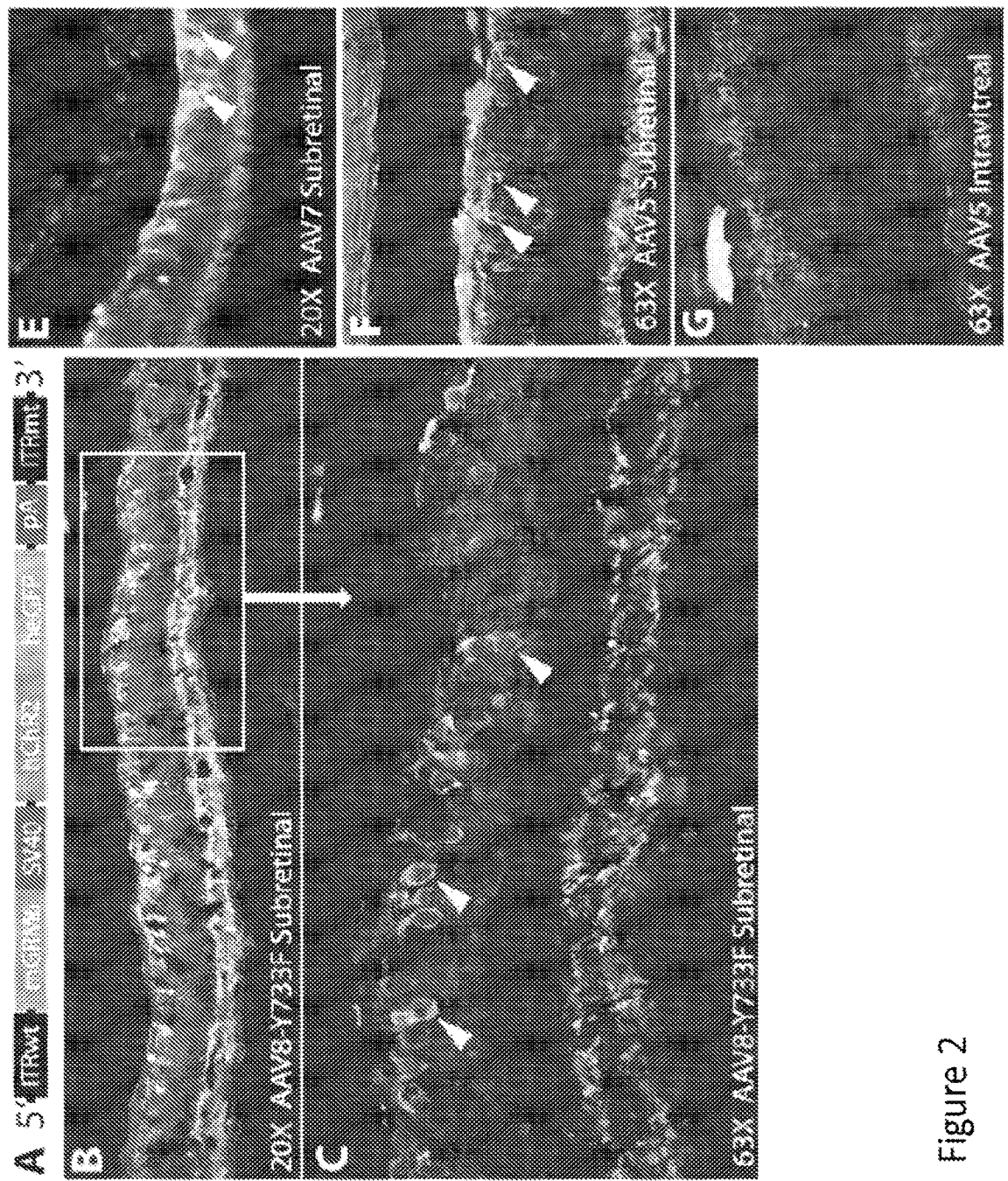
FIG. 2 shows: (A) A brief schematic of the construct. Here, in this example, the self-complementary vector construct contained one wild-type AAV2 terminal resolution site (ITRwt) and one mutant TR (ITRmt), which was packaged in either a capsid tyrosine-mutated rAAV2-Y444F or rAAV8-Y733F. The regulatory region consisted of a 200 bp enhancer region from the murine GRM6 gene fused to a 203 bp SV40 core promoter. The transgene consisted of a mammalian optimized channelrhodopsin-2 (hChR2, 930 bp) fused to a humanized and enhanced green fluorescent protein (heGFP), 700 bp). A polyadenylation signal sequence (β-globin pA, 210 bp) was included. hChR2-heGFP is selectively targeted and expressed in ON bipolar cells in rd10 (B-C) and rd1 (E-G), delivered subretinally or intravitreally with AAV vectors.

FIG. 2 shows (A) GFP expression under the control of the CBA promoter using an AAV8 vector, with a single tyrosine point mutation. Panels B, C, E, and F were conducted with a subretinal injection, panel G, with an intravitreal injection. Substantial expression was seen through both injection types. (B) When using a GRM6 promoter sequence, expression of GFP (green) was localized to the inner nuclear layer and outer plexiform layer in the rd1 mouse. (C) shows that expression is targeted to retinal ON bipolar cell bodies, axons, and dendrites. Images B-C are from treated rd1 mice.

Example 2

Behavioral Testing

Using the water maze task (FIG. 3A), the perceptual threshold (minimum light level) necessary to allow wild-type mice (C57B6) to use visual guidance to find the target platform was measured. At lower light levels, mice were still eventually able to find the platform via tactile sensation, but it took longer, approximately 15 seconds, FIG. 3C)

Figure 3:
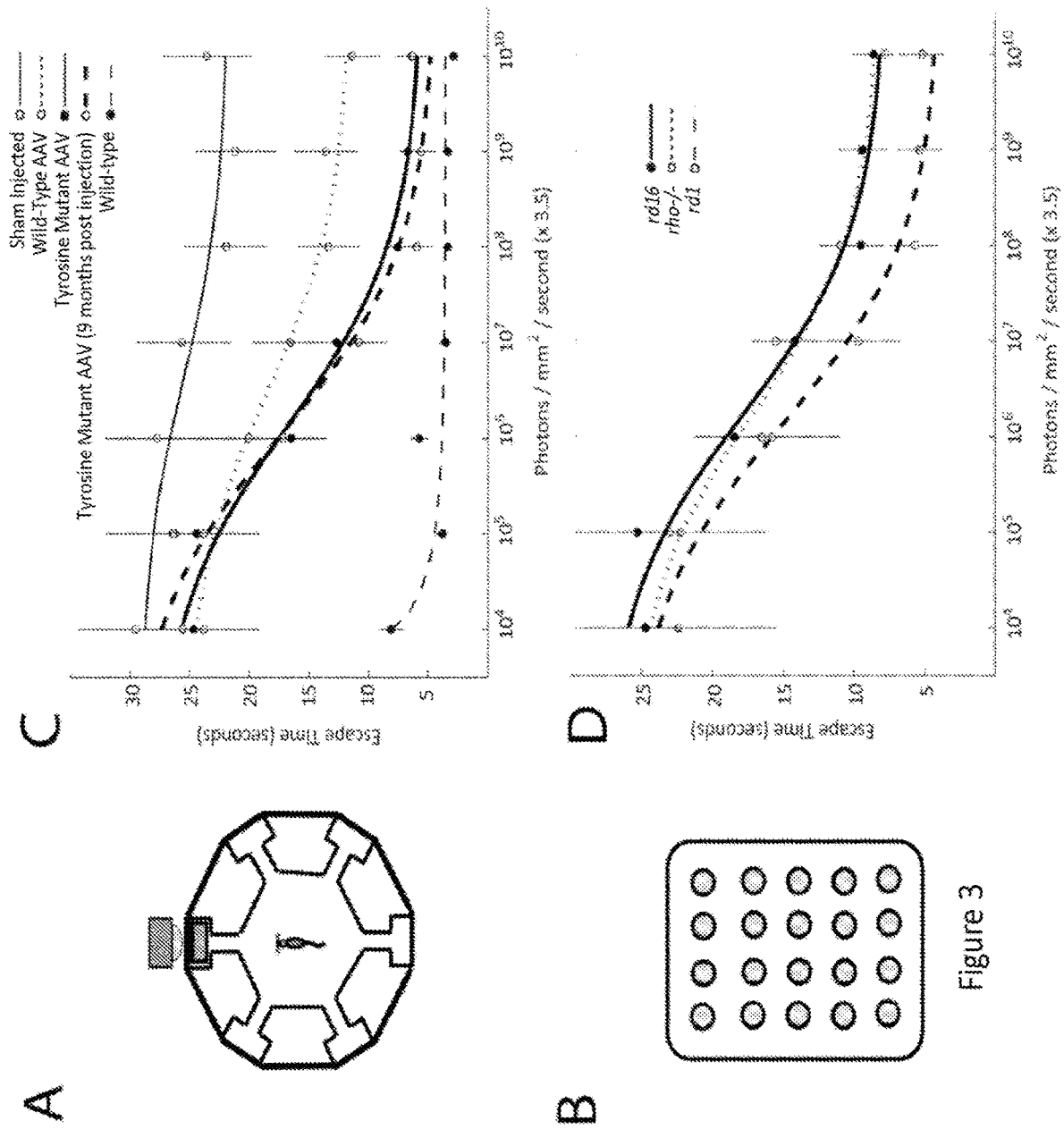
FIG. 3 shows a behavioral response to light stimulation in wild-type, untreated rd1, rd16, and rho −/− mice, and rd1, rd16, and rho −/− mice treated with ChR2. Behavioral response to light stimulation in mice treated with our therapeutic vector. (A) A schematic example of the Morris water maze (B) Schematic of the light source used (6×4 LED array) The light was varied to determine the minimum light necessary for the animal to find the platform and "escape" the maze for (C) wild-type and tyrosine mutant capsid vectors and (D) the 3 different animal types (i.e., rd1, rd16, and rho −/− mice). There were either 3 or 4 mice per group.

As described above, transducing and targeting ChR2 (and GFP) expression to retinal ON bipolar cells in rd1 mice was successful. In these same mice, the expression of ChR2 was tested and in these specific retinal cells such expression led to behavioral improvement in a visually-guided water maze task. 4 different rd1 mouse groups treated with different ChR2 vectors were tested: 1) AAV5-GRM6-ChR2-GFP, 2) AAV5-CBA-ChR2-GFP, 3) AAV8m-GRM6-ChR2-GFP, and 4) AAV9m-CBA-ChR2-GFP. The last two treatment groups (AAV8m and AAV9m) used two different capsid tyrosine mutants of the wild-type serotypes AAV8 and AAV9, respectively. As controls, wild-type C57B6 and untreated rd1 mice were additionally tested on the same task (FIG. 3C). The target was illuminated with approximately $1.5 \times 10^4$ uW/mm$^2$ of light at 470 nm. Wild-type, C57B6 mice were capable of learning the task after 10 sessions of training. The untreated rd1 mice, on the other hand, were unable to learn the task. Of the 4 different ChR2 treatment groups, 3 of them were able to learn the task nearly as well as the wild-type C57B6 mice. This example demonstrates that the therapy is capable of restoring visually-guided behavior in the photoreceptor-less rd1 mouse.

Example 3

Modeling Tissue-Specific Differential Regulation (Prophetic Example)

The DME method is leveraged to discover motifs whose occurrences are likely to provide specificity when included in synthetic promoters.

Proximal promoters of human and mouse transcripts that showed differential expression across 20 terminally differentiated tissues is studied. Among the tissues included are retinal tissue, central nervous system (CNS) tissue, and peripheral nervous system (PNS) tissue. For each tissue, 500 transcripts with the greatest tissue-specific over-expression, and the 500 transcripts with the greatest tissue-specific under-expression are selected. Tissue-specific over-expression (and under-expression) is defined for the experiment as the number of standard deviations by which a transcript exceeds (or falls below) its mean intensity across all tissues. The promoters are taken as the −1000 to +100 regions relative to the TSS. Once applied uniformly to all 20 tissues, predictions about whether a promoter regulates activation or repression in a given tissue, e.g., retinal tissue, CNS tissue, PNS tissue, are made.

Promoter features for this experiment were defined based on experimentally-derived motifs and novel motifs identified using the DME algorithm. Promoter sequences are scanned for elements that matched each (novel or known) motif, and the degree of match was also retained. Among features based on single motifs are the max-score (score of the best matching element to a motif in each promoter) and the match-count (number of matches above a specified score cutoff). Individual features are combined algorithmically to model requirements for the presence of multiple motifs simultaneously (without considering relative order or orientation of the respective sites). Using a large number of such features, a custom implementation of the MARS algorithm (Multivariate Adaptive Regression Splines) is applied. 10-fold cross-validation and a binomial test of the misclassification rates are used to obtain p-values for the predictive accuracy of the models.

The predictive models are able to distinguish tissue-specific elevated from inhibited expression, with statistical significance in 80% of the tissues (45 of 56). These predictors revealed several important aspects of regulatory specificity. For example, for some tissues the optimal predictive models included both positive elements (i.e. present in up-regulating promoters) and negative elements (present in down-regulating promoters). For certain tissues the expression was accurately modeled using simple features, di- and tri-nucleotide composition of promoters, while other tissues required complex models describing synergy between several motifs. The study demonstrates that proximal promoter elements can be used to predict mammalian tissue-specific expression in retinal tissue, CNS tissue, and PNS tissue. Therefore, sequence features can accurately predict tissue-specific expression in mammals.

Example 4

Expression Profiling of the Transcription Start Sites (TSS) and their Associated Promoters in Different Targeted Retinal Cell Types Using Cap Analysis of Gene Expression (CAGE) (Prophetic)

Understanding the gene expression profiles of the target cells, as well as the neighboring cells surrounding the target facilitates developing a functional synthetic promoter. The gene expression of five (5) different subpopulations of retinal cells are evaluated using deep CAGE. Using these data, the differences in gene profiles are calculated within these different cells. The five different populations are: (i) retinal ganglion cells, (ii) rod and ON bipolar cells, (iii) Types 1 and 2 OFF bipolar cells, (iv) Type 3 bipolar cells, and (v) Type 4 bipolar cells. This example is conducted in the rd10 mouse model devoid of photoreceptors at the time of evaluation, an animal model of blindness. Table 1 describes these different retinal cell groups and the associated molecular markers.

For the ganglion, rod and ON bipolar, Type 1 and 2 OFF bipolar, and Type 3 bipolar cell groups, isolated fluorescent cell populations are obtained by using transgenic mice that express Green Fluorescent Protein (GFP) (for example an enhanced GFP, eGFP) coincidentally with Thy1, Gγ13, NK3R, and HCN4, respectively. These mice can be obtained through either the researchers who created the transgenic strain (in the case the Thy1 mouse{Hayworth, 2008 #3978; Unezaki, 2009 #3993}) or through the Gensat Project (in the case of the Gγ13, NK3R, and HCN4 mice). Type 4 OFF bipolar cells are fluorescently labeled through immunohistochemistry, as further described below. For the ganglion, rod and ON bipolar, Type 1 and 2 OFF bipolar, and Type 3 bipolar cell groups, isolated fluorescent cell populations can be obtained by using transgenic mice that express Green Fluorescent Protein (GFP) coincidentally with Thy1, Gγ13, NK3R, and HCN4, respectively. For the Type 4 OFF bipolar cell group, cell fluorescence is established using antibody labeling as no BAC transgenic mouse for this protein exists.

TABLE 1

The table shows five different populations of retinal cells that are targeted for gene profiling using the deep CAGE system. Three of the cell types (ganglion, rod and ON bipolar, and Type 1 and 2 OFF bipolar) are collected in transgenic mice expressing eGFP coincidentally with Thy1, Gγ13 and NK3R, respectively. The other 2 populations of cells (Type 3 and 4 OFF bipolar) are marked and isolated using antibodies specific to those cell types.

| Cell Type | Antibody/ Transgenic | Molecular Marker | References |
|---|---|---|---|
| Ganglion | Transgenic | Thy1 | {Hayworth, 2008 #3978; Unezaki, 2009 #3993} |
| Rod and ON Bipolar | Transgenic | Gγ13 | {Dhingra, 2002 #3621; Huang, 2003 #2525} |
| Type 1 and 2 OFF Bipola | Transgenic | NK3R | {Haverkamp, 2003 #3980; Ghosh, 2004 #2520} |
| Type 3 OFF Bipolar | Transgenic | HCN4 | {Mataruga, 2007 #3981; Wassle, 2009 #3982} |
| Type 4 OFF Bipolar | Antibody | calsenilin | {Haverkamp, 2008 #3983; Wassle, 2009 #3982} |

Immunocytochemistry

All procedures adhere to the Association for Research in Vision and Ophthalmology guidelines for the Use of Animals in Ophthalmic and Vision Research. Immuncytochemistry for this example is conducted in rd10 mice. Mice are sacrificed by terminal isoflurane anesthesia, followed by decapitation and the eyes removed into room-temperature Ames solution, hemisected, and the cornea and lens removed. The eye cups are immediately embedded directly in a cryopreservative solution and frozen immediately, or snap frozen in liquid nitrogen as soon as the eye cup is removed. Prompt preservation of the sample can limit protein and RNA degradation. At a fixed time later, the eye cup is immersed in about 4% paraformaldehyde (PAF) in about 0.1 M phosphate buffer, at about pH 7.4 for about 24 hours. The eye cups are then be transferred to about a 30% sucrose solution and stored for about another 24 hours. The tissue is then imbedded in a 1 part OCT, 2 part sucrose solution and frozen to about −20° C. Retina is then cryosectioned radially at 10-20 micrometers and immunostained with primary and secondary antibodies so that cells can be isolated using the fluorescence-activated cell sorting technique described below.

Cell Isolation and Fluorescent-Activated Cell Sorting (FACS)

FACS sorting is employed for the harvested fluorescent cells from both the transgenic animals and immunohistochemistry-treated tissue. FACS is a type of flow cytometry which allows sorting of a heterogeneous population of cells to help isolate a specific subtype based upon fluorescence.

In this experiment, both 1) BAC-EGFP transgenic mice that have GFP expression isolated to a specific cell subtype (available through the GENSAT project) and 2) retinal tissue treated with antibodies that are known to mark specific retinal cell types (see above) are used. In either case, to dissociate the cells, retinas are isolated and incubated in $Ca^{2+}$ and $Mg^{2+}$-free HBSS with about 20 mM HEPES, about 3 mg/ml BSA, about 3 mg/ml glucose, about 1.5 mM $MgSO_4$, and about 0.0025% trypsin at about 37° C. for about 25 minutes, with gentle shaking. The enzymatic reaction is stopped by adding about 0.25 mg/ml trypsin inhibitor and about 40 ug/ml DNaseI. Tissue is then triturated with a 1 ul pipette tip, followed by a 100 μl pipette tip until the suspension is homogenous. Cell viability and quality of dissociation is checked with EthD-1. The dissociated cells are then sorted by fluorescence-activated cell sorting (FACS) using FACSVantage. Debris and aggregates are gated out by forward and side scatter. The cells are then sorted based on size and fluorescence intensity.

RNA and cDNA Preparation

The total RNA is pooled from each of the different FACS isolated retinal cell population, as described in the preceding section. The RNA is then subjected to about two rounds of hybridization to oligo(dT) beads (Dynal). About 100 nanograms of the resulting mRNA is then fragmented by the addition of about 5× fragmentation buffer (about 200 mM Tris acetate, about pH 8.2, about 500 mM potassium acetate and about 150 mM magnesium acetate) and heating at about 94° C. for about 2 minutes 30 seconds in a theremocycler and is then transferred to ice and run over a Sephadex G50 column to remove the fragmentation ions. About 3 mg of random hexamers is added to prime first-strand reverse transcription according to the manufacturer's protocol (Invitrogen cDNA synthesis kit). After the first strand is synthesized, a custom second strand synthesis buffer (Illumina) is added, and dNTPs, RNase H and *Eshcherichia coli* polymerase I are added to nick translate the second strand synthesis for about 2.5 h at about 16° C. The reaction is then cleaned up on a QiaQuick PCR column and eluted in about 30 ul EB buffer.

Samples are sequenced using Solexa/Illumina GAIT technology.

Data Analysis

Reads are mapped with an updated version of the RMAP read-mapping or any equivalent program. Transcription start sites are identified as peaks in the profiles of mapped reads along the reference genome (mouse assembly mm9) using an existing Hidden Markov Model algorithm. Intensity of expression is measured by normalizing the read counts for each gene within a cell type (i.e. so the intensities sum to 1 for each RNA-seq experiment). Specificity is measured using a Z-score, which accounts for variance across samples; other options for measuring specificity may also be used. For each target cell type, the analysis is expected to produce two sets of specific genes: those specifically up-regulated and those specifically down-regulated in the target cell-type.

Example 5

Computational Development and Synthetic Promoter Optimization (Prophetic)

An integrated experimental and computational method is developed for designing synthetic promoters with regulatory specificity for some selected set of cell types. It is then applied to retinal cell types, for the purpose of expressing a light-sensitive transmembrane protein in OFF bipolar cells, and optionally other retinal cells. Which information best contributes to the design of regulatory specificity, and how best to measure and extract that information using analytic methods applied to the available data is determined herein.

Three strategies for promoter design are used. The first two are expected to provide a controlled evaluation of how specific sources of information can be used. The third strategy is expected to develop a flexible algorithmic framework that builds upon the first two strategies. The third strategy incorporates existing and novel analytic methods, and is expected to become the computational basis of the integrated molecular/computational synthetic promoter design methodology.

Strategy 1: Rational Modifications to Template Promoters

This strategy is based on a template natural promoter with some positive properties of specificity for positive target cells (PTCs) and intensity of regulated expression. The strategy is to modify the template promoter in a way that improves both specificity and intensity, through rationally determined incremental changes. Information to guide the set of changes may come from comparison with homologous sequences. This approach depends on the availability of individual template promoters with the desired properties. The template promoters are taken from regulatory sequences associated with the marker genes The regulatory sequence include the promoter (2000 bp, overlapping the TSS) and enhancer regions, identified computationally, proximal to the relevant genes. Evaluating promoters designed using this strategy is expected to indicate how best to use information from cross-species comparisons, and to what degree this information is important.

In this example the following promoter classes for each PTC are identified:
1. Exact template. Profiling expression in target cells using the template itself is carried out. This is expected to provide the baseline level of expression, both in terms of specificity and intensity.
2. Conserved template. Profiling expression driven by the template with all non-conserved bases replaced at random with bases that appear at low frequency in the corresponding position of the alignment (and that do not appear in the reference species) is carried out.
3. Putative regulatory template. TFBS identification is performed within the promoter, and all sites not included within putative TFBS is modified (as for the conserved template). The definition of putative TFBS for this task is based on PWM search using binding characterizations from TRANSFAC{Matys, 2006 #4015} and JASPAR{Sandelin, 2004 #4030}, and TFBS-specific measures of conservation.
4. Non-reference species template. A homologous primate and a homologous non-primate, non-rodent mammal, are selected, assuming some minimum level of conservation (e.g. at least 33% identity) is present. This is expected to provide information about translating from the model organism.
5. Template with inclusion of elements from Strategy 2. This includes the exact template, with elements identified above included by either replacing parts of the template promoter or by pre-pending the elements 5' to the template.

Use of Cross-Species Conservation

Cross-species conservation is a method for identifying functional non-coding genomic elements{Kellis, 2003 #4010}{Kellis, 2003 #4010}. The template promoter generally provides specificity, and any functional elements in the template is specific to the associated PTC. Information about cross-species conservation from pre-computed full-genome alignments, available from the Genome Bioinformatics Group at UCSC, are identified and computed using the MULTIZ alignment algorithm{Blanchette, 2004 #4006}. Currently, the alignments referenced on the mm9 mouse genome assembly include 30 vertebrate species, and those referenced on the hg18 human assembly include 44 species (both of which can be used to examine mouse conservation). Several measures of conservation can be used, including percent identity, conservation relative to regional average, and binding site-specific conservation.

Promoter Evaluation Plan

For each of the 3 PTCs, approximately 10 promoters are evaluated: 5-6 corresponding to each of 2 templates (i.e. from the marker and from the expression profiles). This is a total of about 30 promoters. The first round of promoter evaluations include those from classes 1-4, as these can be generated with minimal sequence analysis. The class 5 promoters are evaluated following evaluation of promoters from Strategy #2 (herein).

Strategy 2: Designed Regulation by Specific Transcription Factors

This strategy is based on designing a sequence that contains elements selected to bind a specific set of TFs. This method begins with gene expression profiles and the measurement of specificity for each gene in each target cell. To execute this strategy, a useful set of TFs are identified. Once these TFs are identified, promoters are constructed by arranging the corresponding elements in random order immediately adjacent to a basal promoter. Both positive regulators specific to PTCs and negative regulators absent in NTCs are considered. Evaluating promoters designed using this strategy is expected to indicate how best to use information about expression profiles of TFs, including both positive and negative regulators.

To select a useful set of TFs, certain criteria are considered. The criteria are that the TFs be activating and highly specific to the PTCs. Annotations are used to indicate which genes are transcription factors, including Gene Ontology (The Gene Ontology Consortium, 2004), and databases like TRANSFAC{Matys, 2006 #4015}. Annotation can be used to determine whether the TFs appear to be activating. Additional information, primarily from sequence analysis, can be used to support TFs as activating in a particular cell type.

In addition, the following issues are considered:
1. Information about positive vs. negative regulation. Annotations indicating transcriptional regulatory function or presence of DNA binding domains may not be accompanied by information about whether TFs are positive or negative regulators.
2. Reliable binding affinity characterization. The subset for which known binding site information exists is identified. This information may be from databases like TRANSFAC or it may come from genome-wide studies such as ChIP-chip or ChIP-seq.
3. Homologs expressed in NTCs. Any TFs for which some homologs (with respect to binding domain and similar binding specificity) are expressed in the NTCs can be eliminated.

Promoter Evaluation Plan

This strategy requires starting with a basal promoter verified as having no specificity for any of the target cells. Promoters are generated by arranging the binding sites randomly upstream of a basal promoter. For each target cell type 3 random arrangements of selected sites are generated. The use of activator and repressor elements separately and together can be evaluated. This is expected to result in a total of approximately 30 promoters (3 PTCs X 3 arrangements X 3 activator/repressor inclusions).

Strategy 3: Algorithmic Promoter Design

The algorithmic design strategy is the framework for computational aspects of the molecular/computational method. This strategy leverages information from sequence analysis to identify the appropriate elements for inclusion in the synthetic promoter, and, importantly, organization of those elements (i.e. relative order, spacing and orientation). Promoters can be generated once expression data has been obtained.

Promoter Sets for Sequence Analysis

Once expression data and TSS locations have been obtained for the target cell types, sets of training promoters are constructed. For each target cell type, four sets of genes and corresponding promoters are identified: (1) up-regulated positive target promoters (up-PTPs); (2) down-regulated positive target promoters (down-PTPs); (3) up-regulated negative target promoters (up-NTPs); and (4) down-regulated negative target promoters (down-NTPs). Regulatory elements enriched in the up-PTPs relative to (a) down-PTPs and (b) promoters of genes expressed in NTCs (represented by up-NTPs) are candidate activation elements. Conversely, regulatory elements enriched in down-NTPs relative to (a) up-NTPs and (b) down-PTPs are candidate repressive elements. The promoter evaluation strategy tests activating and repressing elements both separately and together.

Identifying Candidate Promoter Elements

Synthetic promoters are constructed by concatenating candidate regulatory elements, and the algorithmic tasks involve identifying appropriate elements and the order in which they should be positioned. To identify sets of candidate elements three approaches are taken. First, the STORM program{Schones, 2007 #4019} is used{Schones, 2007 #4019}, which predicts binding site locations, along with the MULTISTORM to add confidence to predictions by phylogenetic footprinting. Second, the MOTIFCLASS program (also part of CREAD) is used to evaluate enrichment of known motifs (e.g. from TRANSFAC or JASPAR). For motifs identified as enriched in the appropriate promoter sets, strongly matching sites in each promoter are considered candidate elements. Third, the DME algorithm for agnostic discovery of enriched motifs is used, possibly corresponding to TFs not present in any database. Motifs discovered in this way are used in a manner similar to the enriched known motifs. Generally such procedures are expected to predict a large number of elements, and from these elements those with the best enrichment properties are selected and also those with strong organizational properties (see below).

Elucidating Organizational Features of Regulatory Elements

Regulatory elements frequently exist as cis-regulatory modules, placing organizational restrictions that sets of elements must satisfy if they are to have proper regulatory function. Organization refers to relative order, orientation (i.e. strand) and spacing of elements. In some cases, algorithms for elucidating organizational features of regulatory elements are designed by analyzing how the elements appear in natural promoters. In other embodiments, statistical measures of consistency are also designed for these organizational features. In the analysis, if some set of elements has constrained organization (in addition to enrichment of individual elements), then those elements are preferred in synthetic promoters, and design of synthetic promoters take into account any identified organizational constraints.

To elucidate element organization the approach of treating each promoter as the sequence of elements it comprises is taken, represented by element identities and distance between consecutive elements (this is called the TF-map representation).

Allowing Inversions to Model Degree of Order Preservation

Although modeling the organization for individual cis-regulatory modules is intended, the sequences of candidate elements to be aligned also likely correspond to multiple distinct cis-regulatory modules. Changes to the order of elements are allowed so that varying degrees of order preservation can be modeled, for example, to allow broken order between two modules. This is modeled by allowing alignments to reflect inversions of consecutive sets of promoter elements, with penalties for sizes and numbers of inversions included in the alignment objective functions. Existing algorithmic techniques are incorporated to model non-intersecting inversions{Schoniger, 1992 #4020} into the TF-map alignment.

Multiple Alignments

To measure organizational constraints of elements in sets of promoters, multiple TF-maps simultaneously need to usually be aligned. This is analogous to global multiple sequence alignment, two approaches can be used. The progressive alignment approach is based on the current paradigm for global multiple sequence alignment. Progressive alignment begins with pair-wise alignment and then merges pairs of alignments (i.e. aligns) following a guide tree until only a single alignment remains. An algorithm for progressive alignment of TF-maps are designed, including inversions. The second approach is based on the combinatorial problem called multidimensional matching{Downey, 1999 #4031}, which identifies optimal associations of objects from multiple categories. Here, the categories are natural promoters and the objects are the elements in TF-maps. This framework is adapted so that matching is done hierarchically, and higher levels of the hierarchy aggregate elements of lower levels; the structure of associations across promoters can then account for proximity of elements within TF-maps.

Promoter Evaluation Plan

In this stage promoter generation can proceed iteratively. On possible scheme is as follows: about four (4) rounds of promoter evaluation are carried out. Each round evaluates 6-7 promoters per PTC (a total of ~20). First, promoters designed with only activating elements are evaluated. In the next round, repressive elements are tested (possibly with some additional activating promoters). In the third round, promoters that include both activating and repressing elements are evaluated. In the fourth round, promoters that integrate aspects of the best promoters from strategies 1 and 2 with those already observed from the current strategy are tested.

Example 6

Evaluation of Expression Efficacy and Specificity Using Multiple Cell Lines (Prophetic)

In this example, the effectiveness of each of the different synthetic promoters for targeting expression of GFP to the different OFF bipolar cells is evaluated. This is carried out with the following steps: 1) DNA vectors that includes each of the synthetic promoters in Example 5 are created, 2) DNA vectors are electroporated into organotypic retinal cell cultures from rd10 mice, 3) sections are sliced and immunostained for confocal imaging, and 4) expression specificity and breadth is determined by evaluating GFP co-localization with specific antibody staining, and whole mount cell counting. The 3 different OFF bipolar cell populations that are targeted using the synthetic promoters are: 1) Type 1 and 2 OFF bipolar, 2) Type 3 OFF bipolar, and 3) the entire population of OFF bipolar cells, including Type 4. Co-localization of GFP with the NK3R antibody is used to determine targeting of the Type 1 and 2 OFF bipolar populations, the HCN4 antibody for Type 3 OFF bipolar cells, and a triple immuno-stain with NK3R, HCN4, and calsenilin to determine the targeting of the entire OFF bipolar cell population. Only tissues that show any GFP expression within the whole mount prep are immuno-stained and imaged.

Plasmid and Cloning Preparation.

Synthetic promoter sequences are utilized for plasmid creation. The EGFP (vector DNA) and the synthetic promoter (insert DNA) are cloned together. On Day 1, about 1-2 ug of vector DNA and the insert DNA is incubated with the appropriate restriction enzymes in a final volume of about 20 ul, for about 1-2 hours at about 37° C. Shrimp alkaline phosphatase is added to the vector DNA only and then incubated for an additional 1-2 hours at about 37° C. Both the vector and insert DNA is then purified by running it on an agarose gel. The bands of DNA are then cut out using a long wavelength ultraviolet (UV) light. The DNA is further purified using a Qiaquick Extraction column (Qiagen), and then eluted with 20-30 Gel 1 elution buffer (EB). The cohesive 5' and 3' ends are ligated using a T4 DNA ligase (New England Biolabs), and run with a parallel control ligation without the DNA fragment. On Day 2, 1 ul of ligated DNA mix are added to prethawed GC-5 competent cells, incubated on ice for about 30 minutes, heat shocked at about 42° C. for about 45 seconds, 450-900 ul of SOC media are added, and then shaken for about 1 hour at about 37° C. The medium is then distributed to LB plates with the appropriate antibiotics. The plates are incubated overnight at about 37° C. On Day 3, the cell colonies are checked to make sure that the ratio of ligation colonies is about 2× higher than the control colonies. If so, about 2 ml of ligation media are then added to GC-5 cells and incubated at about 37° C. overnight. The vector is then cut with the appropriate restriction enzymes to ensure that the insert DNA is appropriately cloned into vector DNA. In some cases, the entire vector is sequenced.

Organotypic Retinal Culture and Electroporation

All experiments are conducted in accordance with local and national guidelines for animal care. About 12 week old male and female rd10 mice are sacrificed by an overdose (about 5.0 ml/kg) of a mixture of about 42.9 mg/ml ketamine, about 8.57 mg/ml xylazine, and about 1.43 mg/ml acepromazine. The eyes are removed and placed into room-temperature Ames solution. The cornea and lens are removed. The retina are isolated by gently teasing it from the pigment epithelium using forceps. Each retina is sectioned in quarters so that there are about 8 whole mount sections that can be used for culture. DNA prepared in the preceding section are delivered using electroporation. The electroporator (Ingenio) is programmed with the following exemplary parameters: 25 Volts, five pulses, 950 ms off, 50 ms on. A remote foot switch and Petri dish electrode are used. Each retinal section is transferred to the Petri dish electrode, one at a time, using a sterile disposable transfer pipette. Extra solution is removed. About 100 ul of the DNA vector is added. This tissue is oriented to maximize the surface area in the electric field, being careful not to touch the metal sides with the retina. Tissue is then electroporated with the pulsing sequence described above. Then, electroporated retinal sections are mounted, photoreceptor side down, on a 3.0 um FCF filter (1 retinal section per filter paper) in a 12 mm culture plate insert, covered with about 1 drop of synthetic matrix (Matrigel; BD Biosciences), and kept at room temperature for about 10 minutes to allow for coagulation of the matrix. Each culture plate insert and retina are placed into one well of a 24 well plate containing about 550 ul/well of Dulbecco's MEM-F12 (supplemented with 10% horse serum and 5 mM glutamine and buffered with about 20 mM HEPES (about pH 7.4), and incubated at about 37° C. Culture medium is changed after about 1 day and about twice weekly thereafter.

Imaging and Immunohistochemistry

All procedures adhere to the Association for Research in Vision and Ophthalmology guidelines for the Use of Animals in Ophthalmic and Vision Research. After about 3 days of culturing, the electroporated retinal sections are immersed in about 4% paraformaldehyde (PAF) in about 0.1 M phosphate buffer, at about pH 7.4 for about 24 hours. The retinae are then transferred to about a 30% sucrose solution and stored for about another 24 hours. The tissue is then imbedded in a 1 part OCT, 2 part sucrose solution and frozen to − about 20° C. Retina is then cryosectioned radially at about 10-20 micrometers and immunostained with primary and secondary antibodies. GFP expression is evaluated visually. Bipolar cells are marked with a NK3R antibody to determine the localization of GFP expression. The intensity and specificity of GFP expression are evaluated.

Data Analysis, Cell Counting, and Specificity

The specificity of expression can be for example determined by the co-localization of GFP expression and the NK3R antibody marker. If the GFP and NK3R antibody are co-localized, it suggests that the synthetic promoter restricts the expression of the transgene to the retinal OFF bipolar cells. Also, as a negative check, a subset of tissue is labeled with the mGluR6 antibody that marks rod and ON bipolar cells. Co-localization of the mGluR6 antibody and GFP expression would suggest that expression is spreading to ON bipolar cells as well. For breadth of expression, a cell counting technique can be used. For example, using a whole mount retina, cells that are expressing GFP are counted at about a 40× magnification using a grid pattern in 2 mm intervals throughout the retinal section. A total of about 10 retinal sections are evaluated this way.

Example 8

Engineered Sequences

In this example, sequences are determined through evaluation of sequence homology across different genomes from different species. Here, the murine GRM6 enhancer sequence was used to determine the human GRM6 enhancer sequence by way of comparative genomics. Comparative genomics is the study of the relationship a genome sequence or structure, and the function across different biological species. This method takes advantage of the idea that functionally meaningful sequences are conserved across species whereas regions that are unimportant or have little impact on evolutionary success of the organism are usually not conserved. A growing body of knowledge regarding transcriptional regulation of gene expression and consensus sequences for transcription factor binding, combined with annotated genome sequences, makes it possible to carry out a directed search for binding sites of specific activity-regulated transcription factors at the scale of an entire genome. Methods for locating transcription factor binding sites often rely upon relatively simple comparisons of a single sequences or consensus binding sites with individual promoter regions.

Provided herein are engineered GRM6 sequences, by way of example:

```
Engineered murine GRM6 enhancer sequence (mGRM6)
                                       (SEQ. ID NO: 12)
5'-GATCTCCAGATGGCTAAACTTTTAAATCATGAATGAAGTAGATATTA

CCAAATTGCTTTTTCAGCATCCATTTAGATAATCATGTTTTTTGCCTTTA

ATCTGTTAATGTAGTGAATTACAGAAATACATTTCCTAAATCATTACATC

CCCCAAATCGTTAATCTGCTAAAGTACATCTCTGGCTCAAACAAGACTGG

TTG-3,

Engineered Human GRM6 enhancer sequence (hGRM6)
                                       (SEQ. ID NO: 1)
5'-CCGGGTACCATCCTTAGATTATGAAACATTTACAATTATGAATGAAT

ATTAGATGTTATCAAATGCTTTTTCTGCATCCATTTAGATAATCATGTTT

TTCCTTTAATCTGTTAATGCGGTGAATTACATTAATAGATTTCCTAAGTC

ATTAATCTGCTAAAGTGCATTTCTGGGACAAACAGACTTGGTTATGACAT

TGTATGTATAAGCTTACCGGTGCC-3,
```

Also provided is the human sequence with genomic coordinates. All letters are in lower case except for 3 separate pairs of upper case letters separated by a '/'. The first uppercase letter is the human base, and the second is the base most frequently appearing in nonhuman primates.

```
>chr5:178368129-178368328
                                       (SEQ. ID NO: 13)
atacataC/Aaatgtcataaccaagtaggtttgtcccagaaatgcacttt agcagattaatgacttaggaaatctattaatgtaattcacC/Tgcattaa cagattaaaggaaaaacatgattatctaaatggatgcagaaaaagcattt gataacatctaatattcattcataattG/Ttaaatgtttcataatctaag gat
```

Also provided, are the alignments of various nonhuman primate sequences (relative to the human GRM6 sequence), including genomic coordinates.

```
a score = 1023379.000000
+ s hg18.chr5 178368129 98 + 180857866
                                       (SEQ ID NO: 14)
ataca-ta-caatg--
Tcataaccaagtctggtttgtcccagaaatgcactttagcagattaatgacttaggaaatctattaatgtaattcaccgcattaac + s tarSyr1.scaffold 612017 531 99 + 806
                                       (SEQ ID NO: 15)
atatgtta-aaaag--
gcataaccaagtctggtttgtcccagaaatgcactttagcagattaatgacttaggaaacctattaatgtaattcattgcattaac + s calJac1.Contig1543 366102 97 + 443815
                                       (SEQ ID NO: 16)
ataca-ta--aatg--
tcataaccaagtctggtttgtcccagaaatgcactttagcagattaatgacttaggaaatctattaatgtaattcactgcattaac + s rheMac2.chr6 175631705 98 + 178205221
                                       (SEQ ID NO: 17)
ataca-ta-aaatg--
tcatcaccaagtctggtttgtcccagaaatgcactttagcagattaatgacttaggaaatctattaatgtaattcactgcattaac + s ponAbe2.chr5 181601512 98 + 183952662
                                       (SEQ ID NO: 18)
atata-ta-aaatg--
tcataaccaagtctggtttgtcccagaaatgcactttagcagattaatgacttaggaaatctattaatgtaattcactgcattaac + s gorGor1.Supercontig 0097930 528 98 - 2040
                                       (SEQ ID NO: 19)
ataca-ta-caatg--
tcataaccaagtctggtttgtcccagaaattcactttagcagattaatgacttaggaaatctattaatgtaattcactncattaac + s panTro2.chr5 181458562 90 + 183994906
                                       (SEQ ID NO: 20)
ataca-ta-caatg--
tcataaccaagtctggtttgtcccagaaatgcactttagcagattaatgacttaggaaatc--------taattcaccgcattaac a score = 976555.000000
+ s hg18.chr5 178368227 100 + 180857866
                                       (SEQ ID NO: 21)
agattaaag----g-
aaaaacatgattatctaaatggatgcag-aaaaagcatttgataacatctaatattcattcataattgtaaatgtttcataatctaaggat + s tarSyr1.scaffold 612017 630 99 + 806
                                       (SEQ ID NO: 22)
agattaaag----gaaaaaacatgattatctaaatggatgccc-
cagaagcatttgataataccta atattttattcatgattttaa--gttttgcaacctaagaat
```

+ s calJac1.Contig1543 366199 100 + 443815

(SEQ ID NO: 23)

agattaaag----g-
aaaaacatgatcatctaaatggatgcag-aaaaagcatttgataacatctaatattcattcataattttaagtgtttcataatctaaggat + s rheMac2.chr6 175631803 100 + 178205221

(SEQ ID NO: 24)

agattaaag----g-
aaaaacatgattatctaaatggatgcag-aaaaagcatttgataatatctaatattcattcataattttaaatggttcataatctaaggat + s ponAbe2.chr5 181601610 100 + 183952662

(SEQ ID NO: 25)

agattaaag----g-
aaaaacatgattatctaaatggatgcag-aaaaagcatttgataacatctaatattcattcataattttaaatgtttcataatctaaggat + s gorGor1.Supercontig 0097930 626 100 - 2040

(SEQ ID NO: 26)

anattaaag----g-
aaaaacatgattatctaaatggatgcag-aaaaagcatttgataacatctaatatttattcataattttaaatgtttcataatctaaggat + s panTro2.chr5 181458652 100 + 183994906

(SEQ ID NO: 27)

agattaaag----g-
aaaaacatgattatctaaatggatgcag-aaaaagcatttgataacatctaatattcattcataattttaaatgtttcataatctaaggat Example 9

Selective Regulation by the hGRM6 Enhancer Element

Expression of GFP and PKCa proteins in retina of treated animals were evaluated using immunohistochemistry combined with confocal imaging 6 weeks following subretinal injection of a AAV8Y733F-hGRM6-ChR2-eGFP vector.

After the eye cup was dissected, the retina and eye cup was immersed in 4% paraformaldehyde in 0.1 M phosphate buffer at pH 7.4. Tissues were sucrose-infiltrated overnight, and they were frozen in optimal cutting temperature compound on dry ice the next day. Ten micron serial sections of tissues were prepared on a Leica CM 3050 S cryostat.

These tissue slices were indirectly stained with primary antibodies against rabbit anti-green fluorescent, (GFP) IgG (Invitrogen, dilution 1:500) and mouse anti-protein kinase a (PKC) IgG (Santa Cruz Biotechnology, dilution 1:100) diluted in the blocking solution containing 3% BSA+5% goat serum, followed by secondary antibodies against rabbit immunoglobulin G (Invitrogen; Alexa Fluor 488, dilution, 1:1000) and mouse immunoglobulin G (Invitrogen; Alexa Fluor 555, dilution, 1:200). Prolong gold antifade mounting media (Invitrogen) containing DAPI was used to mount the sections and to stain cell nuclei.

Antibody distribution was visualized using a TCS-SP5 Broadband Spectra laser confocal microscope equipped with a 20× and 63× (NA=1.2) objective.

As shown in FIGS. 5-9, the hGRM6 drove expression of the eGFP gene in the retinal ON cone bipolar cells, as indicated by the band of GFP staining in a region associated with retinal ON cone bipolar cells. Less GFP staining was observed in other tissues. The red PKC stain identifies the retinal rod bipolar cells. The lack of overlap between the GFP with the PKC stain supports that the hGRM6 enhancer is selectively driving expression in the retinal cone bipolar cells, as opposed to the retinal rod bipolar cells.

While some embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition, comprising
a cell-transfection vector, wherein the cell-transfection vector comprises a polynucleotide and the polynucleotide comprises a regulatory sequence operationally linked to an encoding sequence,
the regulatory sequence comprises a human GRM6 regulatory sequence, and the encoding sequence encodes a protein, wherein the protein is not human GRM6 protein.

2. The pharmaceutical composition of claim 1, wherein said human GRM6 regulatory sequence is at least 80% identical to SEQ ID NO: 1.

3. The pharmaceutical composition of claim 1, wherein said protein comprises a light-sensitive protein.

4. The pharmaceutical composition of claim 1, wherein said regulatory sequence comprises at least 2 sequences selected from sequences that are at least 80% identical to SEQ ID NOs:2-11.

5. The pharmaceutical composition of claim 1, wherein said regulatory sequence comprises at least 2 copies of one or more sequence selected from sequences that are each independently at least 80% identical to SEQ ID NOs:2-11.

6. The pharmaceutical composition of claim 1, wherein said protein comprises a light-sensitive protein and the light-sensitive protein is selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, Cheta, ChR65, C1 VI, Arch, ArchT, Mac, halorhodopsin, melanopsin, and variants thereof.

7. The pharmaceutical composition of claim 1, wherein said protein comprises a light-sensitive protein and the light-sensitive protein is selected from rhodopsin, blue opsin, red opsin, and variants thereof.

8. The pharmaceutical composition of claim 1, wherein the cell-transfection vector is selected from an adenovirus vector, an adeno-associated virus vector (AAV), a C-type retrovirus vector, a lentivirus vector, a poxvirus vector, a herpes virus vector, an alphavirus vector, and a liposome vector.

9. The pharmaceutical composition of claim 8, wherein the adeno-associated viral vector comprises capsid protein and the capsid protein comprises a mutation.

10. The pharmaceutical composition of claim 9, wherein the mutation comprises an amino acid substituted for a tyrosine.

11. The pharmaceutical composition of claim 1, wherein the human GRM6 regulatory sequence comprises less than 500 base pairs.

12. The pharmaceutical composition of claim 1, wherein said regulatory sequence further comprises an additional regulatory element selected from one or more of an enhancer, a silencer, a locus control region, a proximal promoter, and a core promoter.

13. A method of transfecting retinal cells, comprising contacting a retina with a pharmaceutical composition of claim 1, wherein transfected retinal cells express the protein and greater than 80% of the transfected retinal cells that express the protein are retinal ON bipolar cells.

14. A method of transfecting retinal cells, comprising contacting a retina with a pharmaceutical composition of claim 1, wherein transfected retinal cells express the protein and greater than 80% of the transfected retinal cells that express the protein are retinal ON cone bipolar cells.

15. A method of transfecting retinal cells, comprising contacting a retina with a pharmaceutical composition of claim 1, wherein transfected retinal cells express the protein and less than 20% of the transfected retinal cells that express the protein are retinal OFF rod bipolar cells.

16. A method of transfecting retinal cells, comprising contacting a retina with a pharmaceutical composition of claim 1, wherein said protein comprises a light-sensitive protein and the light-sensitive protein is selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, Cheta, ChR65, C1 VI, melanopsin, and variants thereof.

17. A method of transfecting retinal cells, comprising contacting a retina with a pharmaceutical composition of claim 1, wherein said protein comprises a light-sensitive protein and the light-sensitive protein is selected from rhodopsin, blue opsin, red opsin, and variants thereof.

18. A method of transfecting retinal cells, comprising contacting a retina with a pharmaceutical composition of claim 1, wherein the cell-transfection vector is selected from an adenovirus vector, an adeno-associated virus vector (AAV), a C-type retrovirus vector, a lentivirus vector, a poxvirus vector, a herpes virus vector, an alphavirus vector, and a liposome vector.

19. A method of transfecting cells, comprising
contacting the cells with a cell-transfection vector, wherein the cell-transfection vector comprises a polynucleotide and the polynucleotide comprises a regulatory sequence operationally linked to an encoding sequence, and
the regulatory sequence comprises a human GRM6 regulatory sequence, and the encoding sequence encodes a protein, wherein the protein is not a human GRM6 protein.

20. The method of claim 19, wherein the cell is a retinal cell or a neuron.

* * * * *